(12) United States Patent
Neyts et al.

(10) Patent No.: US 7,737,162 B2
(45) Date of Patent: Jun. 15, 2010

(54) VIRAL INHIBITORS

(75) Inventors: Johan Neyts, Kessel-Lo (BE); Gerhard Pürstinger, Innsbruck (AT); Erik De Clercq, Lovenjoel (BE)

(73) Assignee: Gilead Sciences, Inc., Foster City, CA (US)

( * ) Notice: Subject to any disclaimer, the term of this patent is extended or adjusted under 35 U.S.C. 154(b) by 1503 days.

(21) Appl. No.: 10/519,756

(22) PCT Filed: Jul. 3, 2003

(86) PCT No.: PCT/BE03/00117

§ 371 (c)(1),
(2), (4) Date: Dec. 30, 2004

(87) PCT Pub. No.: WO2004/005286

PCT Pub. Date: Jan. 15, 2004

(65) Prior Publication Data

US 2005/0239821 A1 Oct. 27, 2005

(30) Foreign Application Priority Data

Jul. 3, 2002 (GB) .................................. 0215293.2
Jun. 10, 2003 (GB) .................................. 0313251.1

(51) Int. Cl.
*A61K 31/44* (2006.01)
(52) U.S. Cl. ...................................................... 514/303
(58) Field of Classification Search .................. 514/303
See application file for complete search history.

(56) References Cited

U.S. PATENT DOCUMENTS

| 2,191,978 | A | 2/1940 | Balle et al. |
|---|---|---|---|
| 2,411,662 | A | 11/1946 | Martin et al. |
| 2,516,674 | A | 7/1950 | Havertown et al. |
| 2,548,863 | A | 4/1951 | Havertown et al. |
| 3,985,891 | A | 10/1976 | Kutter et al. |
| 4,358,387 | A | 11/1982 | Zoleski et al. |
| 4,565,816 | A | 1/1986 | Neumann |
| 4,692,443 | A | 9/1987 | Katner |
| 4,804,658 | A | 2/1989 | Manley et al. |
| 4,914,108 | A | 4/1990 | Khanna et al. |
| 4,988,707 | A | 1/1991 | Stealey et al. |
| 4,990,518 | A | 2/1991 | Khanna et al. |
| 5,011,832 | A | 4/1991 | Dininno et al. |
| 5,019,581 | A | 5/1991 | Khanna et al. |
| 5,057,517 | A | 10/1991 | Johnston et al. |
| 5,137,896 | A | 8/1992 | Van Daele |
| 5,208,242 | A | 5/1993 | Khanna et al. |
| 5,227,384 | A | 7/1993 | Khanna et al. |
| 5,302,601 | A | 4/1994 | Khannal et al. |
| 5,332,744 | A | 7/1994 | Chakravarty et al. |
| 5,374,638 | A | 12/1994 | Dhanoa et al. |
| 5,405,964 | A | 4/1995 | Mederski et al. |
| 5,438,063 | A | 8/1995 | Osswald et al. |
| 5,446,032 | A | 8/1995 | Whittaker et al. |
| 5,486,525 | A | 1/1996 | Summers, Jr. et al. |
| 5,585,492 | A | 12/1996 | Chandrakumar et al. |
| 5,587,372 | A | 12/1996 | Aszodi et al. |
| 5,607,944 | A | 3/1997 | Linz et al. |
| 5,719,306 | A | 2/1998 | Chandrakumar et al. |
| 5,723,492 | A | 3/1998 | Chandrakumar et al. |
| 5,854,265 | A | 12/1998 | Anthony |
| 5,859,035 | A | 1/1999 | Anthony et al. |
| 5,872,136 | A | 2/1999 | Anthony et al. |
| 5,874,452 | A | 2/1999 | Anthony |
| 5,880,140 | A | 3/1999 | Anthony |
| 5,883,105 | A | 3/1999 | Anthony |
| 5,939,557 | A | 8/1999 | Anthony et al. |
| 6,051,574 | A | 4/2000 | Anthony |
| 6,063,930 | A | 5/2000 | Dinsmore et al. |
| 6,080,870 | A | 6/2000 | Anthony et al. |
| 6,329,381 | B1 | 12/2001 | Kurimoto et al. |
| 6,376,515 | B2 | 4/2002 | Zhu et al. |
| 6,479,508 | B1 | 11/2002 | Beaulieu et al. |
| 6,492,384 | B1 | 12/2002 | Mederski et al. |
| 6,627,651 | B1 | 9/2003 | Shiraishi et al. |
| 6,767,654 | B2 | 7/2004 | Tamao et al. |
| 6,770,666 | B2 | 8/2004 | Hashimoto et al. |
| 6,803,374 | B2 | 10/2004 | Priestley et al. |

(Continued)

FOREIGN PATENT DOCUMENTS

AU 643289 12/1991

(Continued)

OTHER PUBLICATIONS

West, Solid State Chemistry and its Applications, 1986. p. 365.*

(Continued)

*Primary Examiner*—Shengjun Wang
(74) *Attorney, Agent, or Firm*—Clark & Elbing LLP

(57) ABSTRACT

The present invention relates to a pharmaceutical composition for the treatment or prevention of viral infections comprising as an active principle at least one imidazo[4,5-c]pyridine derivative having the general formula (Z): (formula). The invention also relates to processes for the preparation of compounds according to the invention having above mentioned general formula and their use as a medicine or to treat or prevent viral infections.

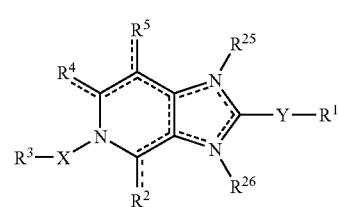

(Z)

9 Claims, No Drawings

U.S. PATENT DOCUMENTS

| | | | |
|---|---|---|---|
| 6,835,739 | B2 | 12/2004 | Zhu et al. |
| 6,844,367 | B1 | 1/2005 | Zhu et al. |
| 7,026,051 | B2 | 4/2006 | Schauer et al. |
| 7,098,231 | B2 | 8/2006 | Poupart et al. |
| 7,112,600 | B1 | 9/2006 | Hashimoto et al. |
| 7,223,785 | B2 | 5/2007 | Beaulieu et al. |
| 7,285,551 | B2 | 10/2007 | Hashimoto et al. |
| 7,294,457 | B2 | 11/2007 | Kukolj et al. |
| 2003/0073836 | A1 | 4/2003 | Priepke et al. |
| 2003/0108862 | A1 | 6/2003 | Kukolj et al. |
| 2004/0082635 | A1 | 4/2004 | Hashimoto et al. |
| 2004/0097438 | A1 | 5/2004 | Hashimoto et al. |
| 2004/0097574 | A1 | 5/2004 | Marshall |
| 2004/0171626 | A1 | 9/2004 | Beaulieu et al. |
| 2004/0186125 | A1 | 9/2004 | Poupart et al. |
| 2005/0026921 | A1 | 2/2005 | Eckhardt et al. |
| 2005/0096337 | A1 | 5/2005 | Ackermann et al. |
| 2005/0222198 | A1 | 10/2005 | Bondy et al. |
| 2006/0052602 | A1 | 3/2006 | Kim et al. |
| 2006/0229336 | A1 | 10/2006 | Kazmierski et al. |
| 2006/0252791 | A1 | 11/2006 | Bondy et al. |
| 2007/0021472 | A1 | 1/2007 | Zhu et al. |
| 2007/0032497 | A1 | 2/2007 | Hashimoto et al. |
| 2007/0244148 | A1 | 10/2007 | Bondy et al. |
| 2008/0188516 | A1 | 8/2008 | Bondy et al. |
| 2008/0199427 | A1 | 8/2008 | Bondy et al. |
| 2009/0036460 | A1 | 2/2009 | Dowdy et al. |

FOREIGN PATENT DOCUMENTS

| | | |
|---|---|---|
| CA | 2093290 | 7/1993 |
| CA | 2158996 | 3/1994 |
| CA | 2 357 771 | 7/2000 |
| CA | 2471566 | 1/2003 |
| CA | 2423800 | 3/2003 |
| CA | 2496249 | 8/2003 |
| DE | 42 11 474 A1 | 10/1993 |
| DE | 42 30 464 A1 | 3/1994 |
| DE | 4230464 | 3/1994 |
| DE | 42 36 026 A1 | 4/1994 |
| DE | 43 09 969 A1 | 9/1994 |
| DE | 43 18 813 A1 | 12/1994 |
| EP | 0 076 530 B1 | 4/1983 |
| EP | 0 138 552 A2 | 4/1985 |
| EP | 0228845 | 7/1987 |
| EP | 0 232 937 A2 | 8/1987 |
| EP | 0 300 726 A1 | 1/1989 |
| EP | 0 300 726 B1 | 1/1989 |
| EP | 0 344 414 A1 | 12/1989 |
| EP | 0 344 414 B1 | 12/1989 |
| EP | 0417745 | 3/1991 |
| EP | 0 462 009 B1 | 12/1991 |
| EP | 0 510 260 A2 | 10/1992 |
| EP | 0 605 836 A1 | 7/1994 |
| EP | 0 706 795 A2 | 4/1996 |
| EP | 1 132 381 A1 | 9/2001 |
| EP | 1 162 196 A1 | 12/2001 |
| EP | 1386923 | 2/2004 |
| EP | 1 400 241 A1 | 3/2004 |
| GB | 2 158 440 A | 11/1985 |
| GB | 2 264 115 A | 8/1993 |
| HU | 78019 | 5/1995 |
| HU | 78019 | 5/1999 |
| IL | 89588 | 10/1993 |
| RU | 860463 | 5/1998 |
| RU | 860463 A1 | 5/1998 |
| SU | 813921 | 12/1986 |
| SU | 813921 A | 12/1986 |
| SU | 1048742 | 12/1986 |
| SU | 1048742 A | 12/1986 |
| SU | 851940 | 4/1988 |
| SU | 851940 A | 4/1988 |
| WO | WO 92/22556 A1 | 12/1992 |
| WO | WO 93/02080 A1 | 2/1993 |
| WO | WO 93/14072 A1 | 7/1993 |
| WO | WO 93/16075 A1 | 8/1993 |
| WO | WO 94/12461 A1 | 6/1994 |
| WO | WO 94/29321 A1 | 12/1994 |
| WO | WO 95/02597 A1 | 1/1995 |
| WO | WO 95/16687 A1 | 6/1995 |
| WO | WO 96/11192 A1 | 4/1996 |
| WO | WO 96/12703 A1 | 5/1996 |
| WO | WO-96/15111 | 5/1996 |
| WO | WO 99/27929 A1 | 6/1999 |
| WO | WO-00/20400 | 4/2000 |
| WO | WO 00/20416 A1 | 4/2000 |
| WO | WO-00/20425 | 4/2000 |
| WO | WO-00/20445 | 4/2000 |
| WO | WO 00/39127 A1 | 7/2000 |
| WO | WO 00/40583 A2 | 7/2000 |
| WO | WO 00/40586 A1 | 7/2000 |
| WO | WO-00/73307 | 12/2000 |
| WO | WO 01/60315 A2 | 8/2001 |
| WO | WO-01/66526 | 9/2001 |
| WO | WO 01/85172 A1 | 11/2001 |
| WO | WO-01/95910 | 12/2001 |
| WO | WO 02/04425 A2 | 1/2002 |
| WO | WO 02/057425 A2 | 7/2002 |
| WO | WO-02/067942 | 9/2002 |
| WO | WO-03/000254 | 1/2003 |
| WO | WO-03/004020 | 1/2003 |
| WO | WO 03/007945 A1 | 1/2003 |
| WO | WO 03/010140 A2 | 2/2003 |
| WO | WO 03/010141 A2 | 2/2003 |
| WO | WO-03/014229 | 2/2003 |
| WO | WO 03/026587 A2 | 4/2003 |
| WO | WO-03/057205 | 7/2003 |
| WO | WO 2004/005286 A2 | 1/2004 |
| WO | WO 2004/005286 A3 | 1/2004 |
| WO | WO-2004/018468 | 3/2004 |
| WO | WO 2004/019935 A1 | 3/2004 |
| WO | WO-2004/033455 | 4/2004 |
| WO | WO-2004/043913 | 5/2004 |
| WO | WO-2004/054974 | 7/2004 |
| WO | WO-2004/067516 | 8/2004 |
| WO | WO-2004/072243 | 8/2004 |
| WO | WO-2005/063744 | 7/2005 |
| WO | WO-2006/029966 | 3/2006 |
| WO | WO-2006/033703 | 3/2006 |
| WO | WO-2006/069193 | 6/2006 |
| WO | WO-2008/005519 | 1/2008 |
| WO | WO-2009/009001 | 1/2009 |

OTHER PUBLICATIONS

Vippagunta et al. Advanced Drug Delivery Reviews, 2001, vol. 48, pp. 3-26.*

Kirk_Othmer Encyclopedia of Chemical Technology, 2002, 4. Crystal Characteristics.*

Akamatsu et al., "New Efficient Route for Solid-Phase Synthesis of Benzimidazole Derivatives," *J. Comb. Chem.* 4:475-483 (2002).

Baginski et al., "Mechanism of Action of a Pestivirus Antiviral Compound," *Proc. Natl. Acad. Sci. U.S.A.* 97:7981-7986 (2000).

Barlin, "Ionisation Constants of Heterocyclic Substances. Part VIII. 1,3,5-Triazaindenes," *J. Chem. Soc. B: Phys. Org.* 4:285-291 (1966).

Barlin and Fenn, "A Carbon-13 Nuclear Magnetic Resonance Study of Protonation in Imidazo[4,5-c]pyridines," *Aust. J. Chem.* 34:1341-1344 (1981).

Barlin and Fenn, "The Preparation and 1H NMR Spectra of Some N-Methylpurines and Related Compounds," *Aust. J. Chem.* 36:633-638 (1983).

Barraclough et al., "An Adventitious Synthesis of a 5-Methylimidazo[4,5-c]pyridine Derivative," *Tet. Lett.* 27:5997-6000 (1986).

Barraclough et al., "Inotropic "A" Ring Substituted Sulmazole and Isomazole Analogues," *J. Med. Chem.* 33:2231-2239 (1990).
Brown et al., "Purine Analogues as Amplifiers of Phleomycin. V. Thioethers of Several Heterocyclic Systems with One or Two Rings," *Aust. J. Chem.* 32:2713-2726 (1979).
Cleve et al., "Derivate des Imidazo[4,5-*b*]- and Imidazo[4,5-*c*]pyridins," *Liebigs Ann. Chem.* 747:158-171 (1971).
Curtin et al., "Discovery and Evaluation of a Series of 3-Acylindole Imidazopyridine Platelet-Activating Factor Anatagonists," *J. Med. Chem.* 41:74-95 (1998).
Kiyama et al., "Synthesis and Evaluation of Novel Nonpeptide Angiotesin II Receptor Antagonists: Imidazo[4,5-*c*]pyridine Derivatives with an Aromatic Substituent," *Chem. Pharm. Bull.* 43:450-460 (1995).
Mederski and Pachler, "Synthesis and Structural Assignment of Some N-Substituted Imidazopyridine Derivatives," *Tetrahedron* 48:10549-10558 (1992).
Robertson et al., "Structure-Activity Relationships of Arylimidazopyridine Cardiotonics: Discovery and Inotropic Activity of 2-[2-Methoxy-4-(methylsulfinyl)phenyl]-1*H*-imidazo[4,5-*c*]pyridine," *J. Med. Chem.* 28:717-727 (1985).
Savarino et al., "Spectral Behaviour of Linked Heterocyclic Systems and Related Dyes," *Spectrochim. Acta A: Mol. Biomol. Spectrosc.* 49A:1379-1393 (1993).
Stanovnik et al., "Methylation of Heterocyclic Compounds Containing NH, SH, and/or OH Groups by Means of N,N-Dimethylformamide Dimethyl Acetal," *Aust. J. Chem.* 34:1729-1738 (1981).
Vassilev et al., "Authentic and Chimeric Full-Length Genomic cDNA Clones of Bovine Viral Diarrhea Virus That Yield Infectious Transcripts," *J. Virol.* 71:471-478 (1997).
Wang et al., "Non-Nucleoside Analogue Inhibitors Bind to an Allosteric Site on HCV NS5B Polymerase. Crystal Structures and Mechanism of Inhibition," *J. Biol. Chem.* 278:9489-9495 (2003).
Yutilov et al., "Synthesis and Antiviral Activity of Spinaceamine," *Khim. Farm. Zh.* 23:56-59 (1989).
Zhang, "Inhibitors of Hepatitis C—A Review of the Recent Patent Literature," *IDrugs* 5:154-158 (2002).
International Preliminary Examination Report (PCT/BE03/00117) (mailed Sep. 3, 2004).
Greenfield N et al., "Increase in the Stability and Helical Content of Estrogen Receptor Alpha in the Presence of the Estrogen Response Element: Analysis by Circular Dichroism Spectroscopy", Biochemistry (2001) vol. 40, pp. 6646-6652.
Kariv et al., "Improvement of 'Hit-to-Lead' Optimization by Integration of in vitro HTS Experimental Models for Early Determination of Pharmacokinetic Properties", *Combinatorial Chemistry and High Throughput Screening* (2002), vol. 5, pp. 459-472.
U.S. Appl. No. 11/658,625, filed Jul. 26, 2005, Kim et al.
U.S. Appl. No. 12/303,207, filed Dec. 2, 2008, Bondy et al.
Baba et al., "Synergistic Antiviral Effects of Antiherpes Compounds and Human Leukocyte Interferon on Varicella-Zoster Virus in Vitro," *Antimicrobial Agents Chemother.* 25:515-517, 1984.
Chou et al., "Quantitative Analysis of Dose-Effect Relationships: The Combined Effects of Multiple Drugs or Enzyme Inhibitors," *Adv. Enzyme Reg.* 22:27-55, 1984.
Elion et al., "Antagonists of Nucleic Acid Derivatives. VIII. Synergism in Combinations of Biochemically Related Antimetabolites," *J. Biol. Chem.* 208:477-488, 1954.
Final Rejection, Dec. 16, 2008, U.S. Appl. No. 11/019,830.
Final Rejection, Mar. 19, 2007, U.S. Appl. No. 11/316,050.
Fletcher et al., "Heterocyclic Systems," *Nomenclature of Organic Adv. Ser.* pp. 49-64, 1974.
Guillory (in Britain ed.) "Polymorphism etc." NY:marcel Dekker Inc. 1999, 1-2, 183-226.
Grazul et al. Natural Product Letters (1994) 5(3): 187-195.
Greenfield et al., "Increase in the Stability and Helical Content of Estrogen Receptor Alpha in the Presence of the Estrogen Response Element: Analysis by Circular Dichroism Spectroscopy," *Biochemistry* 40:6646-6652, 2001.
Griesser, Chapter 8, The Importance of Solvates (pp. 211-230), In the text, Polymorphism: In the Pharmaceutical Industry, Hilfiker, 2006.
International Preliminary Report on Patentability for PCT/US2004/043112 dated Apr. 25, 2006.
International Preliminary Report on Patentability for PCT/US2005/026606 dated Feb. 20, 2007.
International Preliminary Report on Patentability for PCT/US2005/046477 dated Mar. 16, 2007.
International Preliminary Report on Patentability for PCT/US2007/015553 dated Jan. 13, 2009.
International Search Report for PCT/BE2003/000117 dated Dec. 16, 2003.
International Search Report for PCT/US2004/043112 dated Jun. 27, 2005.
International Search Report for PCT/US2004/043112) dated Jul. 5, 2005.
International Search Report for PCT/US2005/026606 dated Feb. 13, 2006.
International Search Report for PCT/US2005/046477 dated Jun. 2, 2006.
International Search Report for PCT/US2007/015553 dated Mar. 6, 2008.
International Search Report for PCT/US2008/008259 dated Oct. 14, 2008.
Jacob III, P., "Resolution of (+/−) 5-Bromonornicotine. Synthesis of (R)- and (S)- Nornicotine of High Enantiomeric Purity," *J. Org. Chem.* 47:4165-4167, 1982.
Johnson, A.W. Invitation to Organic Chemistry 1999 Jones and Bartlett: Missisauga, Canada p. 24.
Jones, Maitland Organic Chemistry Norton: New York, 1997, p. 84-99.
Kariv et al., "Improvement of 'Hit-to-Lead' Optimization by Integration of in Vitro HTS Experimental Models for Early Determination of Pharmacokinetic Properties," *Comb. Chem. High Throughput Screen.* 5:459-472, 2002.
Kuno et al (1993) "Studies on Cerebral Protective Agents, IV. Synthesis of Novel 4-Arylpyridine and 4- arylpyridazine Derivatives with Anti-Anoxic Activity," Chem Phar. Bull. 41(1):136-162.
Lindenbach et al. (2005) "Unraveling Hepatitis C Virus Replication from Genome to Function," Nature 436-:933-938.
Lochmüller et al., "Chromatographic Resolution of Enantiomers Selective Review," *J. Chromatography* 113:283-302, 1975.
Montgomery et al., "1-B-D-Arabinofuranosyl, etc.," J. Med. Chem., 1982,25,96-98.
Non-Final Rejection, Feb. 11, 2009, U.S. Appl. No. 10/583,814.
Non-Final Rejection, Mar. 12, 2008, U.S. Appl. No. 11/019,830.
Non-Final Rejection, Mar. 25, 2009, U.S. Appl. No. 12/022,557.
Non-Final Rejection, Oct. 29, 2008, U.S. Appl. No. 11/825,598.
Non-Final Rejection, Sep. 27, 2006, U.S. Appl. No. 11/316,050.
Okamoto et al., "Optical Resolution of Dihydropyridine Enantiomers by High-Performance Liquid Chromatography Using PhenylCarbamates of Polysaccharides as a Chiral Stationary Phase," *J. Chromatography* 513:375-378, 1990.
Paeshuyse et al., "A Novel, Highly Selective, etc.," J of Virology, Jan. 2006, 80(1), 149-160.
Penning et al., "Synthesis of Imidazopyridines as Potent Inhibitors of Leukotriene A4 Hydrolase," *Bioorg. Med. Chem. Lett.* 13:1137-1139, 2003.
Puerstinger et al. "Substituted 5-benzyl-2-phenyl-5H-imidazo[4,5-c]pyridines: A new class of pestivirus inhibitors" Bioorganic & Medicinal Chemistry Letters 2006, 16:5345-5349.
Puerstinger et al. "Antiviral 2,5-disubstituted imidazo[4,5-c]pyridines: From anti-pestivirus to anti-hepatitis C virus activity" Bioorganic & Medicinal Chemistry Letters 2007, 17:391-393.
Rigaudy et al., "Fundamental Heterocyclic Systems," *Nomenclature of Organic Adv. Ser.* pp. 53-76, 1979.
Self et al. (1991) "Romazarit: A Potential Disease-Modifying Antirheumatic Drug," J. Med. Chem. 34:772-777.
Siddiqui et al., "3-Deaza- and, etc.," J. Med. Chem., 1995, 38, 1035-1038.
Vippagunta et al. "Crystalline Solid" Advanced Drug Delivery Reviews 48:3-26 (2001).
Written Opinion for PCT/US2004/043112 dated Oct. 18, 2005.
Written Opinion for PCT/US2005/046477 dated Jun. 2, 2006.
Written Opinion for PCT/US2007/015553 dated Jan. 7, 2009.
Written Opinion for PCT/US2005/026606 dated Feb. 13, 2006.
Zhang, "Studies on the Synthesis and Single Crystal Structure of 3-methyl-6-(p-methylphenyl) Pyridazine," 2001 Journal of Sichuan Normal University (Natural Science) 24(4):384-386.

* cited by examiner

VIRAL INHIBITORS

CROSS REFERENCE TO RELATED APPLICATIONS

This application is the U.S. National Stage of International Application No. PCT/BE2003/000117, filed Jul. 3, 2003, which, in turn, claims the benefit of British patent applications 0215293.2 and 0313251.1, filed Jul. 3, 2002 and Jun. 10, 2003, respectively.

FIELD OF THE INVENTION

The present invention relates to a series of novel imidazo[4,5-c]pyridine derivatives, processes for their preparation, their use to treat or prevent viral infections and their use to manufacture a medicine to treat or prevent viral infections, particularly infections with viruses belonging to the family of the Flaviviridae and Picornaviridae and more preferably infections with hepatitis-C-virus (HCV). The present invention also relates to the use of novel imidazo[4,5-c]pyridine derivatives to treat viral infections and their use to manufacture a medicine to treat viral infections, preferably infections with viruses belonging to the family of the Flaviviridae or Picornaviridae and more particularly infections with BVDV, HCV or Coxsackie viruses.

BACKGROUND OF THE INVENTION

The family of the Flaviviridae consists of 3 genera, the pestiviruses, the flaviviruses and the hepaciviruses and also contains the hepatitis G virus (HGV/GBV-C) that has not yet been assigned to a genus. Pestiviruses such as the Classical Swine Fever Virus (CSFV), the Bovine Viral Diarrhea Virus (BVDV) and the Border Disease Virus (BDV) cause infections of domestic livestock (respectively pigs, cattle and sheep) and are responsible for significant economic losses world-wide. BVDV, the prototypic representative of the pestivirus genus is ubiquitous and causes a range of clinical manifestations, including abortion, teratogenesis, respiratory problems, chronic wasting disease, immune system dysfunction, and predisposition to secondary viral and bacterial infections and may also cause acute fatal diseases. Foetuses of cattle can be infected persistently with BVDV, these animals remain viremic throughout life and serve as a continuous sources for virus spread in herds.

Vaccines are used in some countries with varying degrees of success to control pestivirus disease. In other countries, animal culling and slaughter are used to contain pestivirus disease outbreaks.

The World Health Organization estimates that world-wide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1 to 5% of whom may develop liver cancer during the next then years. The only treatment option available today is the use of interferon α-2 (or its pegylated from) either alone or combined with ribavirin. However, sustained response is only observed in about 40% of the patients and treatment is associated with serious adverse effects. There is thus an urgent need for potent and selective inhibitors of the replication of the HCV in order to treat infections with HCV. Furthermore, the study of specific inhibitors of HCV replication has been hampered by the fact that it is not possible to propagate HCV (efficiently) in cell culture. Since HCV and pestiviruses belong to the same virus family and share many similarities (organisation of the genome, analogous gene products and replication cycle), pestiviruses have been adopted as a model and surrogate for HCV. For example BVDV is closely related to hepatitis C virus (HCV) and used as a surrogate virus in drug development for HCV infection.

The compound 3-[((2-dipropylamino)ethyl)thio]-5H-1,2,4-triazino[5,6-b]indole has been reported to selectively inhibit the replication of BVDV and other pestiviruses (Baginski S G et al., Proc. Natl. Acad. Sci. U.S.A. 2000 Jul. 5; 97(14):7981-6). Currently, there is no treatment strategy available for controlling infections caused by pestiviruses.

Coxsackie viruses belong to the group of the enteroviruses, family of the Picornaviridae. They cause a heterogeneous group of infections including herpangina, aseptic meningitis, a common-cold-like syndrome, a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis.

Currently only pleconaril (3-13,5-dimethyl-4-[[3-methyl-5-isoxazolyl)propyl]phenyl]-5-(trifluoromethyl-1,2,4-oxadiazole)) and enviroxime (2-amino-1-(isopropylsulfonyl)-6-benzimidazole phenyl ketone oxime) have been studied clinically for the treatment of infections with enteroviruses. Pleconaril is a so called "capsid function-inhibitor"; enviroxime prevents the formation of the RNA replicative intermediate. Enviroxime resulted in only modest clinical and virological benefit in some studies and no benefits in others. Clinical response with pleconaril has been observed in some studies, but the compound has not been approved by the Food and Drug Administration (hearing of Mar. 18$^{th}$, 2002).

U.S. Pat. Nos. 4,914,108, 4,990,518, 4,988,707, 5,227,384, 5,302,601 and 5,486,525 describe 5-substituted [4,5-c]imidazopyridine derivatives useful in the treatment of diseases or disorders mediated by platelet-activating factor. The compounds were found to inhibit $^3$H-PAF binding to human platelets.

EP 1132381 describes esters of 2,2-dimethylpropionic acid comprising a benzmidazole structure having an inhibitory activity of elastase.

WO 96/1192 describes compounds of the general formula Ar1-Q-Ar2-YR-Z, wherein Z is optionally a [4,5-c]imidazopyridine which are proposed as LTA4 hydrolase inhibitors useful for the treatment of inflammatory diseases mediated by LTB$_4$ production WO 96/12703 describes heteroarylthioalkyl thiophenolic compounds having 5-lipoxygenase inhibitory activity which are suggested to be useful in the treatment of 5-lipoxygenase mediated conditions.

Chemical Abstracts acc no. 1987:18435 and Chemical Abstracts acc no. 1983:594812 describe the synthesis of two imidazo[4,5-b] and of imidazo[4,5c]pyridine derivatives substituted with piperazinyl and furanyl groups.

EP 1162196 describes fused ring compounds for the use as therapeutic agents for hepatitis C. The fused 5 and 6 membered ring is made up of optionally substituted carbon atoms or nitrogen atoms and optionally one oxygen, sulfur atom or substituted nitrogen atom on the 5 membered ring. WO 95/02597 describes imidazo[4,5c]pyridine derivatives not substituted at the N5 with antiviral activity GB2158440 describes 4,5,6,7-tetrahydroimidazo[4,5-c]pyridine derivatives with antiviral activities.

STN database accession 110:165603 & Khimiko-Farmatsevtichsskii Zurnal, 23:1, (1989), 26-59, describe spinaceamine derivatives such as 5H-imidazo [4,5-c]pyridine-5-ethanol, 1,4,6,7-tetrahydro-alpha-(4-methoxyphenyl)-1,2-dimethyl compounds with antiviral activity (small pox virus).

STN database accession 132:222537 and HU73019 describe N-alkylated azoles with antibacterial activity.

WO9927929 describes [4.3.0] nitrogen containing ring systems and homologous compounds which are proposed as farnesyl-protein transferase inhibitors applicable in the treatment of cancer.

WO9611192 describes 5-substituted imidazo(4,5)pyridine compounds and related molecules for use as anti-inflammatory compounds by inhibiting leukotriene A4 hydrolase.

EP344414 describes 5-Substituted imidazo[4,5-c]pyridines for the treatment of diseases such as inflammation, cardiovascular disorders and asthma.

WO9516687 describes imidazopyridine indoles which act as platelet activating factor antagonists:

J. Comb. Chem. (2000) 4:5, 475-483 describes the synthesis of benzimidazole compound for use in small organic libraries.

In view of their important pharmacological value, there is a need for drugs having antiviral activity, optionally selective activity against viruses belonging to the family of Flaviviridae including hepatitis C virus, and against viruses belong to the family of Picornaviridae.

SUMMARY OF THE INVENTION

In the present invention, new selective anti-viral compounds are being provided. The compounds are imidazo[4,5-c]pyridine derivatives and it has been shown that they possess a broad anti-viral activity. Members of the Flaviviridae and of the Picornaviridae families are being inhibited. The present invention demons that the compounds inhibit the replication of BVDV, HCV and Coxsackie virus. Furthermore, the anti-BVDV activity of the compounds is based on the inhibition of the viral polymerase enzyme of BVDV. Therefore, these imidazo[4,5-c]pyridine derivatives constitute a new potent class of anti-viral compounds that can be used in the treatment and prevention of viral infections in animals, mammals and humans, more specifically for the treatment and prevention of BVDV, HCV and Coxsackie virus infections.

The present invention relates to imidazo[4,5-c]pyridine derivatives. The invention further relates to compounds having anti-viral activity, more specifically to imidazo[4,5-c] pyridine derivatives that inhibit the replication of viruses. Most particularly, the invention relates to imidazo[4,5-c]pyridine derivatives which inhibit the replication of viruses of the family of the Flaviviridae and the Picornaviridae and yet more specifically to compounds that inhibit the replication of BVDV (Bovine Viral Diarrhea Virus), HCV (Hepatitis C Virus) and Coxsackie virus. Present invention furthermore relates to the use of the compounds as a medicine and more specifically to use the compounds as an anti-viral. The invention also relates to methods for preparation of all such compounds and pharmaceutical compositions comprising them. The invention further relates to the use of said compounds in the manufacture of a medicament useful for the treatment of BVDV, HCV or Coxsackie virus infections, as well as for treatment of other viral, retroviral or lentiviral infections such as HIV. The present invention also relates to a method of treatment of viral infections, by using said compounds.

One aspect of the present invention is the provision of imidazo[4,5-c]pyridine derivatives, compounds of formula (A) which effectively show antiviral properties, in particular against members of the Flaviviridae and the Picornaviridae and more in particular against BVDV, HCV and Coxsackie virus, and consequently may be useful for the treatment of subjects infected with BVDV, HCV or Coxsackie virus.

According to a first aspect the invention relates to the use of imidazo[4,5-c]pyridine compounds as antiviral compounds, more particularly as compounds active against BVDV, HCV and Coxsackivirus, which correspond to the general formula (Z),

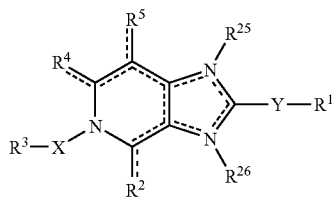

wherein:
the dotted lines represent an optional double bond, provided that no two double bonds are adjacent to one another, and that the dotted lines represent at least 3, optionally 4 double bonds;

$R^1$ is selected from hydrogen; aryl unsubstituted or substituted with one or more $R^6$, heterocyclic ring unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, O; $S(O)_m$; $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, —O(CH$_2$)$_{1-5}$—, —(CH$_2$)$_{1-4}$—O—(CH$_2$)$_{1-4}$—, —S—(CH$_2$)$_{1-5}$—, —(CH$_2$)$_{1-4}$—S—(CH$_2$)$_{1-4}$—, —NR$^{11}$—(CH$_2$)$_{1-5}$—, —(CH$_2$)$_{1-4}$—NR$^{11}$—(CH$_2$)$_{1-4}$— and $C_{3-10}$ cycloalkylidene;

Each $R^2$ and $R^4$ is independently selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; NO$_2$; NR$^7$R$^8$; OCF$_3$; haloalkyl; C(=O)R$^9$; C(=S) R$^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_310$ cycloalkylthio; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring; or, when one of R$^{25}$ or R$^{26}$ is different from hydrogen, either $R^2$ or $R^4$ is selected from (=O), (=S), and (=NR$^{27}$);

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —CH$_2$—, —CH(CH$_3$)—, —CH$_2$—CH$_2$—, —CH$_2$—CH$_2$—CH$_2$—, —CH$_2$—CH$_2$—CH$_2$—CH$_2$), —(CH$_2$)$_{2-4}$—O—(CH$_2$)$_{2-4}$—, —(CH$_2$)$_{2-4}$—S—(CH$_2$)$_{2-4}$—, —(CH$_2$)$_{2-4}$—NR$^{10}$—(CH$_2$)$_{2-4}$—, $C_{3-10}$ cycloalkylidene, $C_{2-6}$ alkenylene (such as —CH=CH—CH$_2$—), $C_{2-6}$ alkynylene;

m is any integer from 0 to 2;

$R^3$ is selected from the group consisting of aryl; aryloxy; arylthio; aryl-NR$^{10}$—; 5 or 6 membered heterocyclic, oxyheterocyclic or thioheterocyclic ring;; and each of said aryl, aryloxy, arylthio, aryl-NR$^{10}$—5 or 6 membered heterocyclic, oxyheterocyclic or thioheterocyclic ring is optionally substituted with one or more R$^{17}$; C$_{3-10}$ cycloalkyl, oxycycloalkyl or thiocycloalkyl; C$_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

R$^5$ is independently selected from the group consisting of hydrogen; C$_{1-8}$ alkyl; C$_{2-18}$ alkenyl; C$_{2-18}$ alkynyl; C$_{1-18}$ alkoxy; C$_{1-18}$ alkylthio; halogen; OH; CN; NO$_2$; NR$^7$R$^8$; OCF$_3$; haloalkyl; C(=O)R$^9$; C(=S)R$^9$; SH; aryl; aryloxy; arylthio; arylalkyl; C$_{1-18}$ hydroxyalkyl; C$_{3-10}$ cycloalkyl; C$_{3-10}$ cycloalkyloxy; C$_{3-10}$ cycloalkylthio C$_{3-10}$ cycloalkenyl; C$_{3-10}$ cycloalkynyl; 5 or 6 membered heterocyclic, oxyheterocyclic or thioheterocyclic ring;

Each R$^6$ and R$^{17}$ is independently selected from the group consisting of hydrogen; C$_{1-18}$ alkyl; C$_{2-18}$ alkenyl; C$_{2-18}$ alkynyl; C$_{1-18}$ alkoxy; C$_{1-18}$ alkylthio; C$_{3-10}$ cycloalkyl, C$_{3-10}$ cycloalkenyl or C$_{3-10}$ cycloalkynyl; halogen; OH; CN; NO$_2$; NR$^7$R$^8$; OCF$_3$; haloalkyl; C(=O)R$^{18}$; C(=S)R$^{18}$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; C$_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, C$_{1-18}$ hydroxyalkyl is optionally substituted with 1 or more R$^{19}$;

Each R$^7$ and R$^8$ is independently selected from the group consisting of H; C$_{1-18}$ alkyl; C$_{1-18}$ alkenyl; aryl; C$_{3-10}$ cycloalkyl; C$_{4-10}$ cycloalkenyl; 5-6 membered heterocyclic ring; C(=O)R$^{12}$; C(=S)R$^{12}$; an amino acid residue linked through a carboxyl group thereof; alternatively, R$^7$ and R$^8$, together with the nitrogen to which they are attached, combine to form a 5-6 membered heterocyclic ring;

Each R$^9$ and R$^{18}$ is independently selected from the group consisting of H; OH; C$_{1-18}$ alkyl; C$_{2-18}$ alkenyl; C$_{3-10}$ cycloalkyl; C$_{4-10}$ cycloalkenyl; C$_{1-18}$ alkoxy; NR$^{15}$R$^{16}$; aryl an amino acid residue linked through an amino group thereof;

Each R$^{10}$ and R$^{11}$ is independently selected from the group the group consisting of H; C$_{1-18}$ alkyl; C$_{1-18}$ alkenyl; C$_{3-10}$ cycloalkyl; C$_{4-10}$ cycloalkenyl; aryl; C(=O)R$^{12}$; 5-6 membered heterocyclin ring; an amino acid residue linked through a carboxyl group thereof;

R$^{12}$ is independently selected from the group consisting of H; C$_{1-18}$ alkyl; C$_{2-18}$ alkenyl; aryl; C$_{3-10}$ cycloalkyl; C$_{4-10}$ cycloalkenyl; an amino acid residue linked through an amino group thereof;

Each R$^{13}$ and R$^{14}$ is independently selected from the group consisting of H; C$_{1-18}$ alkyl; C$_{2-18}$ alkenyl; aryl; C$_{3-10}$ cycloalkyl; C$_{4-10}$ cycloalkenyl; C(=O)R$^{12}$; C(=S)R$^{12}$; an amino acid residue linked through a carboxyl group thereof;

Each R$^{15}$ and R$^{16}$ is independently selected from the group consisting of H; C$_{1-8}$ alkyl; C$_{2-18}$ alkenyl; C$_{2-18}$ alkynyl; aryl; C$_{3-10}$ cycloalkyl; C$_{4-10}$ cycloalkenyl; an amino acid residue linked through a carboxyl group thereof;

R$^{19}$ is independently selected from the group consisting of H; C$_{1-18}$ alkyl, preferably C$_{1-6}$ alkyl; C$_{2-18}$ alkenyl; C$_{2-18}$ alkynyl; C$_{1-18}$ alkoxy, preferably C$_{1-6}$ alkoxy; C$_{1-8}$ alkylthio; C$_{3-10}$ cycloalkyl; C$_{4-10}$ cycloalkynyl; halogen; OH; CN; NO$_2$; NR$^{20}$R$^{21}$; OCF$_3$; haloalkyl; C(=O)R$^{22}$; C(=S)R$^{22}$; SH; C(=O)N(C$_{1-6}$ alkyl), N(H)S(O)(O)(C$_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocyclic, oxyheterocyclic or thioheterocyclic ring each unsubstituted or substituted with 1 or more halogens;

Each R$^{20}$ and R$^{21}$ is independently selected from the group consisting of H; C$_{1-18}$ alkyl, preferably C$_{1-6}$ alkyl; C$_{2-18}$ alkenyl; C$_{2-18}$ alkynyl; aryl; C$_{3-10}$ cycloalkyl; C$_{4-10}$ cycloalkenyl; C(=O)R$^{12}$, C(=S)R$^{12}$;

R$^{22}$ is independently selected from H; OH; C$_{1-18}$ alkyl; C$_{2-18}$ alkenyl; C$_{1-18}$ alkoxy; NR$^{23}$R$^{24}$; aryl; C$_{3-10}$ cycloalkyl,; C$_{4-10}$ cycloalkenyl;

Each R$^{23}$ and R$^{24}$ is independently selected from the group the group consisting of H; C$_{1-18}$ alkyl, preferably C$_{2-3}$ alkyl, wherein C$_{2-3}$ alkyl taken together with N of R$^{22}$ can form a saturated heterocycle, which heterocycle is optionally substituted with OH or aryl or an amino acid residue;

Each R$^{25}$ or R$^{26}$, selected from the group consisting of of H, C$_{1-18}$ alkyl, preferably C$_{1-4}$ alkyl; C$_{3-10}$ cycloalkyl, such as C$_{5-10}$ bicycloalkyl; C$_{3-10}$ cycloalkenyl; (C$_{3-8}$ cycloalkyl)-C$_{1-3}$ alkyl; aryl, such as phenyl; 5 or 6 membered heterocyclic ring, such as pyridyl; alkylaryl, such as benzyl; and each of said C$_{1-18}$ alkyl, preferably C$_{1-4}$ alkyl, C$_{3-10}$ cycloalkyl, C$_{3-10}$ cycloalkenyl, (C$_{3-8}$ cycloalkyl)-C$_{1-3}$ alkyl, C$_{5-10}$ bicycloalkyl, adamantyl, phenyl, pyridyl and benzyl is optionally substituted with 1-4 of each of C$_{1-6}$ alkyl, C$_{1-6}$ alkoxy, halo, CH$_2$OH, oxybenzyl, and OH; and heterocyclic ring having 3 to 7 carbon atoms, preferably a saturated heterocyclic ring wherein the heteroatoms are S, S(O), or S(O)$_2$ separated from the imidazopyridyl ring nitrogen atom by at least 2 heterocyclic ring carbon atoms. Provided that either R$^{25}$ or R$^{26}$ is hydrogen. Typically R$^{25}$ or R$^{26}$ is cyclopentyl or cyclohexyl; provided that if the compound is substituted at R$^{25}$ or R$^{26}$, either R$^2$ or R$^4$ is selected from (=O), (=S), and (=NR$^{27}$); and R$^{27}$ is selected from the group consisting of H, C$_{1-18}$ alkyl, C$_{3-10}$ cycloalkyl, (C$_{3-10}$ cycloalkyl)-C$_{1-6}$ alkyl; aryl; arylalkyl, such as benzyl.

According to a second aspect, the invention relates to imidazo[4,5-c]pyridine compounds, which according to the general embodiment of the invention correspond to compounds according to the general formula (A), pharmaceutically acceptable salts, solvates, tautomers, isomers thereof,

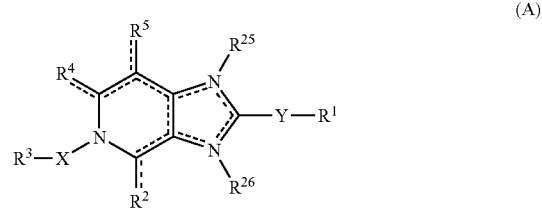

(A)

wherein:
the dotted lines represent an optional double bond, provided that no two double bonds are adjacent to one another, and that the dotted lines represent at least 3, optionally 4 double bonds;

R$^1$ is selected from hydrogen; aryl unsubstituted or substituted with one or more R$^6$, heterocyclic ring unsubstituted or substituted with one or more R$^6$, C$_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, O; $S(O)_m$; $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, $-O(CH_2)_{1-5}-$, $-(CH_2)_{1-4}-O-(CH_2)_{1-4}-$, $-S-(CH_2)_{1-5}-$, $-CH_2)_{1-4}-S-(CH_2)_{1-4}-$, $-NR^{11}-(CH_2)_{1-5}-$, $-(CH_2)_{1-4}-NR^{11}-(CH_2)_{1-4}-$ and $C_{3-10}$ cycloalkylidene;

Each $R^2$ and $R^4$ is independently selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring; or, when one of $R^{25}$ or $R^{26}$ is different from hydrogen, either $R^2$ or $R^4$ is selected from (=O), (=S), and (=NR^{27});

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example $-CH_2-$, $-CH(CH_3)-$, $-CH_2-CH_2-$, $-CH_2-CH_2-CH_2-$, $-CH_2-CH_2-CH_2-CH_2$), $-(CH_2)_{2-4}-O-(CH_2)_{2-4}-$, $-(CH_2)_{2-4}-S-(CH_2)_{2-4}-$, $-(CH_2)_{2-4}-NR^{10}-(CH_2)_{2-4}-$, $C_{3-10}$ cycloalkylidene, $C_{2-6}$ alkenylene (such as $-CH=CH-CH_2-$), $C_{2-6}$ alkynylene;

m is any integer from 0 to 2;

$R^3$ is selected from the group consisting of aryl; aryloxy; arylthio; aryl-$NR^{10}-$; 5 or 6 membered heterocyclic, oxyheterocyclic or thioheterocyclic ring; and each of said aryl, aryloxy, arylthio, aryl-$NR^{10}-$, 5 or 6 membered heterocyclic, oxyheterocyclic or thioheterocyclic ring is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^5$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocyclic, oxyheterocyclic or thioheterocyclic ring;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^{18}$; $C(=S)R^{18}$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$;

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocyclic ring; $C(=O)R^{12}$; $C(=S)R^{12}$; an amino acid residue linked through a carboxyl group thereof; alternatively, $R^7$ and $R^8$, together with the nitrogen to which they are attached, combine to form a 5-6 membered heterocyclic ring;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl an amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; $C(=O)R^{12}$; 5-6 membered heterocyclin ring; an amino acid residue linked through a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each $R^{13}$ and $R^{14}$ is independently selected from the group consisting of H; $C_{1-18}$ alkyl; $C_{2-18}$ alkenyl; aryl; $C_{3-10}$ cycloalkyl; $C_{4-10}$ cycloalkenyl; $C(=O)R^{12}$; $C(=S)R^{12}$; an amino acid residue linked through a carboxyl group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$ alkyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocyclic, oxyheterocyclic or thioheterocyclic ring each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ $C(=O)R^{12}$, $C(=S)R^{12}$;

$R^{22}$ is independently selected from H; OH; $C_{1-18}$ alkyl; $C_{2-18}$ alkenyl; $C_{1-18}$ alkoxy; $NR^{23}R^{24}$; aryl; $C_{3-10}$ cycloalkyl,; $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Each $R^{25}$ or $R^{26}$, selected from the group consisting of of H, $C_{1-18}$ alkyl, preferably $C_{1-4}$ alkyl; $C_{3-10}$ cycloalkyl, such as $C_{5-10}$ bicycloalkyl; $C_{3-10}$ cycloalkenyl; ($C_{3-8}$ cycloalkyl)-$C_{1-3}$ alkyl; aryl, such as phenyl; 5 or 6 membered heterocyclic ring, such as pyridyl; alkylaryl, such as benzyl; and each of said $C_{1-18}$ alkyl, preferably $C_{1-4}$ alkyl, $C_{3-10}$ cycloalkyl, $C_{3-10}$ cycloalkenyl, $(C_{3-8}$ cycloalkyl)-$C_{1-3}$ alkyl, $C_{5-10}$ bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocyclic ring having 3 to 7 carbon atoms, preferably a saturated heterocyclic ring wherein the heteroatoms are S, S(O), or S(O)$_2$ separated from the imidazopyridyl ring nitrogen atom by at least 2 heterocyclic ring carbon atoms. Provided that either $R^{25}$ or $R^{26}$ is hydrogen. Typically $R^{25}$ or $R^{26}$ is cyclopentyl or cyclohexyl; provided that if the compound is substituted at $R^{25}$ or $R^{26}$, either $R^2$ or $R^4$ is selected from (=O), (=S), and (=NR$^{27}$); and $R^{27}$ is selected from the group consisting of H, $C_{1-18}$ alkyl, $C_{3-10}$ cycloalkyl, $(C_{3-10}$ cycloalkyl)-$C_{1-6}$ alkyl; aryl; arylalkyl, such as benzyl.

More particularly, the present invention relates to compounds according to the general formula (Z) and/or (A) as defined above, provided that:

the substituents X, Y, $R^1$, $R^2$, $R^3$, $R^4$, $R^5$ are not a cephalosporin or wherein the substituents X, Y, $R^1$, $R^2$, $R^3$, $R^4$, $R^5$ are not an azabicyclo group, more particularly not 5-Thia-1-aza-bicyclo[4.2.0]oct-2-en-8-one;

the compound is not 5-(2-piperidin-1-yl-ethyl)-2-(4-hydroxyphenyl)-1H-imidazo[4,5-c]pyridin-5-ium bromide (X=ethyl, Y=bond, $R^1$=phenyl substituted in para with OH, $R^2$=H, $R^3$=unsubstituted heterocycle wherein heteroatom is N, $R^4$, $R^5$=H) (as disclosed in example 52 of EP 1132381);

the compound is not 4-[5-(2-{4-[Bis-(4-fluorophenyl)-methyl]-piperazin-1-yl}-ethyl)-5H-imidazo[4,5-c]pyridin-2-yl]phenol (X=ethyl, Y=bond, $R^1$=phenyl substituted in para with OH, $R^2$=H, $R^3$=heterocycle with 2 N heteroatoms, wherein one N is substituted with an arylalkyl consisting of CH(Phenyl)$_2$, wherein each phenyl carries an F in para)(as disclosed in example 54 of EP 1132381);

the compound is not 4-[5-{4-[Bis-(4-fluorophenyl)-methyl]-piperazin-1-yl}-propyl)-5H-imidazo[4,5-c]pyridin-2-yl]phenol (X=butyl, Y=bond, $R^1$=phenyl substituted in para with OH, $R^2$=H. $R^3$=heterocycle with 2 N heteroatoms, wherein one N is substituted with an arylalkyl consisting of CH(Phenyl)$_2$, wherein each phenyl carries an F in para)(as disclosed in example 55 of EP 1132381);

The compound is not 5-(phenylmethyl)-5H-imidazo[4,5-c]pyridine wherein phenyl is substituted with CONR$^{15}$R$^{16}$ and $R^{15}$ is a branched C3 alkyl and $R^{16}$ is phenyl (X=—CH$_2$—; Y=bond; $R^1$=hydrogen; $R^2$=H; $R^3$=phenyl substituted with 1 C(=O)R$^{18}$, wherein $R^{18}$ is NR$^{15}$R$^{16}$, with $R^{15}$ and $R^{16}$ a branched $C_6$ alkyl; $R^4$=H) (as disclosed in example 35 of U.S. Pat. No. 5,302,601);

The compound is not 6-(5H-imidazo[4,5-c]pyridin-5-ylmethyl)-N-(1-methylethyl)-N-phenyl-3-pyridinecarboxamide (X=—CH$_2$—; Y=bond; $R^1$=hydrogen; $R^2$=H, $R^3$=pyridine substituted with 1 $R^6$, wherein $R^6$=1 C=0 R$^{18}$, wherein $R^{18}$ is NR$^{15}$R$^{16}$, wherein $R^{15}$=isopropyl and $R^{16}$=phenyl) (as disclosed in example 6 of U.S. Pat. No. 4,990,518);

The compound is not a compound wherein X=—CH$^2$—; Y=bond; $R^1$=hydrogen; $R^2$=H, $R^3$=5-6 membered heterocyclic ring, in particular a pyridinyl or furanyl, substituted with 1 $R^{17}$ wherein $R^{17}$=C(=O)R$^{18}$, and wherein $R^{18}$=NR$^{15}$R$^{16}$ and $R^{15}$ and $R^{16}$ are either a $C_{1-18}$ alkyl, in particular methyl, ethyl or isopropyl, $C_{2-18}$ alkenyl, in particular 2-methyl allyl, or a $C_{3-10}$ cycloalkyl, in particular cyclopentyl or cyclohexyl. (as disclosed in U.S. Pat. No. 4,990,518);

The compound is not a compound wherein X=—CH$^2$—; Y=bond; $R^1$=hydrogen; $R^2$=H, $R^3$=5-6 membered heterocyclic ring, in particular a pyridinyl or furanyl, substituted with 1 $R^{17}$ wherein $R^{17}$=C(=O)R$^{18}$, and wherein $R^{18}$=$C_{3-10}$ cycloalkyl or $C_{4-10}$ cycloalkenyl.

The compound is not 2,6-bis(1,1,-dimethylethyl)-4-[[2-(5H-imidazo-[4,5-c]pyridin-5-yl)ethyl]thio]-phenol hydrate and/or 2,6-bis(1,1,-dimethylethyl)-4-[[2-(5H-imidazo-[4,5-c]pyridin-5-yl)propyl]thio]-phenol hydrate (X=CH$^2$—CH$^2$—; Y=bond; $R^1$=hydrogen, $R^2$=H, $R^3$=thioaryl substituted with 3R$^6$, wherein $R^6$=2 branched $C_4$ alkyl in meta and OH in para)(as disclosed in example 6 of WO96/12703);

The compound is not 5-[2-(Biphenyl-4-yloxy)-ethyl]-5H-imidazo[4,5-c]pyridine (X=CH$_2$CH$_2$, Y=bond, $R^1$=hydrogen, $R^2$=H, $R^3$=phenoxy substituted with 1 $R^{17}$ in para, wherein $R^{17}$=benzyl; R4=H) (as disclosed in WO96/11192);

The compound is not 5-[2-(4-Phenoxy-phenoxy)-ethyl]-5H-imidazo[4,5-c]pyridine (X=CH$_2$CH$_2$, Y=bond, $R^1$=hydrogen, $R^2$=H, $R^3$=phenoxy substituted with 1 $R^{17}$ in para, wherein $R^{17}$=phenoxy; R4=H) (as disclosed in WO96/11192);

the compound is not not 5-(5-benzyl-2,3-dihydro-benzofuran-2-ylmethyl)-5H-imidazo[4,5-c]pyridine (as disclosed in WO96/11192:

the compound is not 5-[2-[4-(phenylmethyl)phenoxy] ethyl]-5H-imidazo[4,5-c]pyridine hydrate (as disclosed in WO96/11192);

the compound is not 5-[2-[(phenylmethoxy)phenoxy] ethyl]-5H-imidazo[4,5-c]pyridine (as disclosed in WO96/11192);

the compound is not 5-[2-[4-phenoxyphenoxy)ethyl]-5H-imidazo4,5-c]pyridine (as disclosed in WO96/11192);

the compound is not 5-[3-[4-(phenoxyphenoxy)propyl]-5H-imidazo[4,5-c]pyridine (as disclosed in WO96/21192):

the compound is not 5-[2-[4-(4-fluorophenoxy)phenoxy) ethyl]-5H-imidazo[4,5-c]-pyridine (as disclosed in WO96/11192);

the compound is not 5-[3-[4(phenylmethyl)phenoxy)propyl]-5H-imidazo[4,5-c]pyridine (as disclosed in WO96/11192).

The compound is not [5-(4-Fluorobenzyl)-5H-imidazo[4,5c]pyridin-2-yl]-methylamine (X=CH$_2$, Y=NR11, wherein R11=methyl, R1=R$^2$=H, $R^3$-phenyl substituted with 1 $R^{17}$ in para, wherein $R^6$ is F, R4=H, R5=H) (as disclosed in EP76530);

The compound is not 2,6-bis(1,1,-dimethylethyl)-4-[[3-(5H-imidazo-[4,5-c]pyridin-5-yl)propyl]thio]-phenol hydrate (X=CH$_2$—CH$_2$—CH$_2$, Y=bond; R1=hydrogen, $R^2$=H, $R^3$-thiophenyl substituted with 3 $R^6$, wherein $R^6$=2 branched C4 yl in meta and OH in para) (as disclosed in WO96/12703);

The compound is not 2,6-bis(1,1,-dimethylethyl)-4-[[2-(5H-imidazo-[4,5-c]pyridin-5-yl)ethyl]thio]-phenol hydrate (X=S—CH$_2$—CH$_2$, Y=bond; R1=hydrogen, $R^2$=H, $R^3$-thiophenyl substituted with 3 $R^6$, wherein $R^6$=2 branched C4 alkyl in meta and OH in para) (as disclosed in WO96/12703);

The compound is not 2,6-bis(1,1,-dimethylethyl)-4-[[4-(5H-imidazo-[4,5-c]pyridin-5-yl)butyl]thio]-phenol hydrate X=S—CH$_2$—CH$_2$—CH$_2$, Y=bond;

R1=hydrogen, $R^2$=H, $R^3$=thiophenyl substituted with 3 $R^6$, wherein $R^6$=2 branched C4 alkyl in meta and OH in para) (as disclosed in WO96/12703);

The compound is not (±) 2,6-bis(1,1,-dimethylethyl)-4-[[2-hydroxy-3-(5H-imidazo-[4,5-c]pyridin-5-yl)butyl] thio]-phenol hydrate (X=S—$CH_2$—CHOH—$CH_2$, Y=bonded; RI1=hydrogen, $R^2$=H, $R^3$-thiophenyl substituted with 3 $R^6$, wherein $R^6$=2 branched C4 alkyl in meta and OH in para) (as disclosed in WO96/12703);

The compound is not 5-[2-(4-Phenylmethyloxy-phenoxy)-ethyl]-5H-imidazo[4,5-c]pyridine (X=$CH_2CH_2$, Y=bond, R1=hydrogen, $R^2$=H, $R^3$=phenoxy substituted with 1 $R^{17}$ in para, wherein $R^{17}$=benzyl oxy) (as disclosed in WO96/11192);

The compound is not 5-[3-(4-Phenoxy-phenoxy)-propyl]-5H-imidazo[4,5c]pyridine (X=$CH_2CH_2CH_2$, Y=bond, R1=hydrogen, $R^2$=H, $R^3$=phenoxy substituted with 1 $R^6$ in para, wherein $R^6$=phenoxy substituted in para with F; R4=H) (as disclosed in WO96/11192);

The compound is not 5-{2-[4-(4-Fluorophenoxy)-phenoxy]-ethyl}-5H-imidazo[4,5-c]pyridine (X=$CH_2CH_2$, Y=bond, R1=hydrogen, $R^2$=H, $R^3$=phenoxy substituted with 1 $R^6$ in para, wherein $R^6$=phenoxy, substituted in para with F; R4=H) (as disclosed in WO96/11192);

The compound is not 5-[3-(4-Phenylmethyl-phenoxy)-propyl]-5H-imidazo[4,5-c]pyridine (X=$CH_2CH_2CH_2$, Y=bond, R1=hydrogen, $R^2$=H, $R^3$=phenoxy substituted with 1 $R^6$ in para, wherein $R^6$=benzyl; R4=H) (as disclosed in WO96/11192);

The compound is not (1H-Indol-3-yl)-[3-(2-methyl-5H-imidazo[4,5-c]pyridine-5-carbonyl)-phenyl]-methanone (X=—(C=O)— or $SO_2$, Y=$CH_2$, R1=H, $R^2$=H, $R^3$=phenyl substituted with 1 $R^6$, wherein $R^6$ is C(=O)$R^{18}$, wherein $R^{18}$ is indole) (as disclosed in U.S. Pat. No. 5,486,525);

the compound is not 4 or 3-[(2-methyl-5H-imidazo[4,5c]pyridine-5-yl)methyl]-benzoic acid alkylester or 5-[4 or 3-(alkoxycarbonyl-phenyl)-methyl]-2-methyl-5H-imidazo[4,5-c]pyridine, in particular 4 or 3-[(2-methyl-5H-imidazo[4,5-c]pyridin-5-yl)methyl]-methyl ester (X=$CH_2$, Y=$CH_2$, R1=H, $R^2$=H, $R^3$=phenyl substituted at the para or meta position with 1$R^{17}$, wherein $R^{17}$ is (C=O)$R^{18}$, wherein $R^{18}$=alkoxy) (as disclosed in U.S. Pat. No. 5,486,525)

the compound is not 5-[(fluorophenyl)methyl]-2-amino-5-H-imidazo[4,5-c]-pyridine (X$R^3$=fluorobenzyl, Y=N$R^{11}$ with $R^{11}$=methyl, $R^1$=H, $R^2$, $R^3$, $R^4$=H) (as disclosed in U.S. Pat. No. 5,137,896);

the compound is not ((5-[4-(Fluorophenyl)methyl]-5-H-imidazo[4,5-c]-pyridine-2-yl) methyl)-carbamaat, methyl ester (X$R^3$=fluorobenzyl, Y=C(=O)R12 with R12=methyl, $R^1$=H, $R^2$, $R^3$, $R^4$=H) (as disclosed in U.S. Pat. No. 5,137,896);

the compound is not 5-(4-Chlorophenylmethyl)-2-(piperidin-1-ylmethyl)-5H-imidazo(4,5-c]pyridine and its dihydrochloride salt (X$R^3$=chlorobenzyl, Y=—$CH_2$—, $R^1$=piperidinyl) (as disclosed in Justus Liebis Annalen der Chemie (1971), 747, 158-171);

the compound is not 5-(4-Chlorophenylmethyl)-2-(4-methyl-piperazin-1-ylmethyl)-5H-imidazo[4,5-c]pyridine (X$R^3$=chlorobenzyl, Y=—$CH_2$—, $R^1$=piperazinyl, $R^6$=methyl) (as disclosed in Journal of the Chemical Society [section B]: Physical Organic (1966), 4, 285-291);

the compound is not 5-[5-(5-azabenzimidazolyl)methyl)-1-(4-cyanobenzyl)imidazole (as disclosed in WO99/27929)

Particularly, the invention relates to a compound according to the general formula (Z) and/or A as described above wherein, if Y is a bond and $R^1$ is an aryl, this aryl is not phenyl para substituted with OH and optionally further substituted with methyl, methoxy, nitro, diethylamino, Cl, Br, or F; or, if Y is a bond and R1 is a aryl para substituted with OH and optionally further substituted with methyl, methoxy, nitro, diethylamino, Cl, Br, or F, and X is an alkylene, $R^3$ is not a heterocyclic ring containing N; and/or if Y is a bond or $(CH_2)_{1-6}$, $R^1$ is H, X is $CH_2$ and $R^3$ is phenyl with 1$R^{17}$, wherein $R^{17}$ is C(=O)$R^{18}$, then $R^{18}$ is selected from H; OH; $C_{1-18}$ alkyl; $C_{2-18}$ alkenyl; $C_{1-18}$ alkoxy; $NR^{15}R^{16}$; aryl an amino acid residue linked through an amino group thereof; i.e. R18 is not a $C_{3-10}$ cycloalkyl or $C_{4-10}$ cycloalkenyl; and/or if Y is a bond or $(CH2)_{1-6}$, then $R^1$ is an aryl unsubstituted or substituted with one or more $R^6$, heterocyclic ring unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$; i.e. YR1 is not H or $C_{1-6}$ alkyl; and/or if Y is a bond or $(CH2)_{1-6}$, $R^1$ is H, and $R^3$ is a 5 membered heterocyclic ring with one $R^{17}$, wherein R17 is C(=O)R18 and R18 is $NR^{15}R^{16}$, then $R^{15}$ and $R^{16}$ are not a $C_{1-18}$ alkyl or a cycloalkyl; or if Y is a bond or $(CH2)_{1-6}$, and $R^1$ is H, and $R^3$ is a 5 membered heterocyclic ring with one $R^{17}$, wherein R17 is C(=O)R18 then R18 is selected from H; OH; $C_{1-18}$ alkyl; $C_{2-18}$ alkenyl; $C_{3-10}$ cycloalkyl; $C_{4-10}$ cycloalkenyl; $C_{1-18}$ alkoxy; aryl an amino acid residue linked through an amino group thereof; i.e. $R^{18}$ is not $NR^{15}R^{16}$; or if Y is a bond or $(CH2)_{1-6}$, $R^1$ is H, X is —CH2- and $R^3$ is phenyl, substituted with one $R^{17}$, then $R^{17}$ is independently selected from the group hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; C(=S)$R^{18}$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$; i.e., then $R^{17}$ is not (C=O)$R^{18}$; and/or if Y is a bond or $(CH2)_{1-6}$, and $R^1$ is H, and $R^3$ is a 5 membered heterocyclic ring with one $R^{17}$, wherein R17 is C(=O)R18 then R18 is selected from H; OH; $C_{1-18}$ alkyl; aryl, $NR^{15}R^{16}$; i.e. wherein $R^{18}$ is not $C_{1-18}$ alkoxy; and/or if Y is a bond or $(CH2)_{1-6}$, and $R^1$ is H, and $R^3$ is a 5 membered heterocyclic ring with one $R^{17}$, wherein $R^{17}$ is C(=O)$R^{18}$ then $R^{18}$ is selected from OH; $C_{1-18}$ alkyl; $C_{1-18}$ alkoxy; aryl, $NR^{15}R^{16}$; i.e. wherein $R^{18}$ is not H;

and/or if Y is a bond, $R^1$ is hydrogen, X is an alkyl and $R^3$ is an aryl thio substituted with 3 $R^{17}$, and 1 $R^{17}$ is OH in para, the remaining $R^{17}$ are independently selected from the group consisting of hydrogen; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$; i.e. the remaining $R^{17}$ are not a $C_{1-8}$ alkyl;

and/or if Y is a bond, $R^1$ is a hydrogen, X is —(CH2-CH2)-, then $R^3$ is selected from aryl; aryloxy; aryl-$NR^{10}$—; 5 or 6 membered heterocyclic, oxyheterocyclic or thioheterocyclic ring; and each of said aryl, aryloxy, aryl-$NR^{10}$—, 5 or 6 membered heterocyclic, oxyheterocyclic or thioheterocyclic ring is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms; i.e. then $R^3$ is not an arylthio or if X is —(CH2CH2)-S, $R^3$ is not an aryl;

and/or if Y is a bond, $R^1$ is H, X is an alkylene and $R^3$ is phenoxy, $R^{17}$ is independently selected from the group hydrogen; $C_{1-18}$, alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)R^9$; SH; aryl; arylthio; arylalkyl (except benzyl); arylalkyloxy (except oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$; i.e. if $R^3$ is phenoxy, $R^{17}$ is not benzyl or phenoxy or oxybenzyl;

and/or if $XR^3$ is fluorobenzyl, $R^2$, $R^3$, $R^4$ are $R^1$=H and Y is $NR^{11}$, $R^{11}$ is selected from H; $C_{1-18}$ alkyl; $C_{1-18}$ alkenyl; $C_{3-10}$ cycloalkyl; $C_{4-10}$ cycloalkenyl; aryl; 5-6 membered heterocyclin ring; an amino acid residue linked through a carboxyl group thereof, i.e. $R^{11}$ is not methyl or $C(=O)R^{12}$;

If X is $CH_2$ and $R^3$ is a phenyl substituted in para with Cl, and Y is $CH_2$, then $R^1$ is not piperazinyl, or If X is $CH_2$ and $R^3$ is a phenyl substituted in para with Cl, and Y is $CH_2$, then $R^1$ heterocyclic ring is aromatic;

and/or

If $R^5$ is an aryl, aryloxy or benzyl group, $R^1$ is not H or $C_{3-10}$ alkyl, or If $R^1$ is H or $C_{3-10}$ alkyl, then $R^5$ is selected from hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; arylthio; arylalkyl (except benzyl); $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocyclic, oxyheterocyclic or thioheterocyclic ring, i.e., $R^5$ is not an aryl, aryloxy or benzyl;

The compounds of the invention optionally exclude those compounds according to the general formula (Z) and/or (A) as described above, wherein $YR^1$ is not hydrogen, an unsubstituted $C_{3-10}$ cycloalkyl, or a $C_{1-6}$ alkyl.

The compounds of the invention optionally exclude those compounds according to the general formula (Z) and/or (A) as described above, wherein Y $R^1$ is not phenyl para substituted with OH.

The compounds of the invention optionally exclude those compounds according to the general formula (Z) and/or (A) as described above, wherein $R^1$ is not H, Y is not $NR^{11}$ with R11 $C_{1-6}$ alkyl or methyl, and/or $YR^1$ is not monomethylamino.

The compounds of the invention optionally exclude those compounds according to the general formula (Z) and/or (A) as described above, wherein $R^1$ is a phenyl substituted with 1R6, R6 is $C(=O)R^{18}$ and $R^{18}$ is t-butoxy.

The compounds of the invention optionally exclude those compounds according to the general formula (Z) and/or (A) as described above, wherein $R^1$ is not piperidinyl and is not piperazinyl substituted with methyl.

The compounds of this invention optionally exclude those in which $XR^3$ is equivalent to the substructure —$(CH_2)$n-Y'—C(O)N($R_1$')($R_2$') set forth on column 1, line 49 to column 2 line 38 of U.S. Pat. No. 5,302,601 wherein $R_1$' and $R_2$' are each independently selected from hydrogen; straight or branched chain alkyl of 1 to 15 carbon atoms: cycloalkyl having 3 to 8 carbon atoms; substituted cycloalkyl which can be substituted one or more by alkyl of 1 to 6 carbon atoms; bicycloalkyl having 3 to 8 carbon atoms in each ring; heterocyclicalkyl having 4 to 8 carbon atoms which can be optionally substituted by alkyl of 1 to 6 carbon atoms; heteroaromatic having 5 or 6 carbon atoms which can be optionally substituted by alkyl having 1 to 6 carbon atoms; phenyl; substituted phenyl which can be substituted one or more by a group independently selected from alkyl having 1 to 6 carbon atoms or halogen; straight or branched alkenyl having 3 to 15 carbon atoms with the proviso that the double bond of the alkenyl group cannot be adjacent to the nitrogen; cycloalkenyl having 5 to 8 carbon atoms with the proviso that the double bond cannot be adjacent to the nitrogen; and $R_1$' and $R_2$' cannot both be hydrogen; Y' is phenyl or phenyl substituted once or more than at one or more of the 2, 3, 5 or 6 positions of the phenyl ring by substituents independently selected from the group consisting of alkoxy having 1 to 6 carbon atoms; halogen wherein the halogen is selected from bromo, fluoro, or chloro; straight or branched chain alkyl having 1 to 6 carbon atoms: substituted straight or branched chain alkyl which can be substituted one or more by halogen; thioalkyl wherein the alkyl has 1 to 6 carbon atoms; alkoxyalkyl wherein the alkyl groups are each 1 to 6 carbon atoms; hydroxyalkyl wherein the alkyl has 1 to 6 carbon atoms; alkylthioalkyl wherein the alkyl groups are each 1 to 6 carbon atoms; cyano; mercaptoalkyl wherein the alkyl has 1 to 6 carbon atoms; hydroxy; amino; alkylamino wherein the alkyl group has 1 to 6 carbon atoms; and dialkylamino wherein the alkyl groups are each 1 to 6 carbon atoms; n is an unit integer 1 to 5 and the comparable disclosure in any member of the patent family of U.S. Pat. No. 5,302,601, which disclosure is herewith expressly incorporated by reference.

The compounds of this invention optionally exclude those in which $R^5$ contains any of the substituents designated as <<Ar>> in WO 00/39127 (incorporated expressly herein by reference), in particular aryl, arylphenoxy, or benzyl.

Typically, the compounds of this invention do not include the compounds of example 35 of U.S. Pat. No. 5,302,601, example 6 of U.S. Pat. No. 4,990,518, examples 1 to 5 of U.S. Pat. No. 4,988,707, examples 3 and/or 11 of WO 96/12703 and/or compounds 340A, 347C, 349C, 351 C, 355C and/or 356 C of WO 96/11192 and/or their methylene homologues, the disclosure of which are herewith expressly incorporated by reference.

Optionally, the compounds of this invention also exclude all methylene homologues of known compounds which are excluded from the scope of this invention.

The compounds of this invention optionally exclude those in which XR3 is equivalent to the substructure —(CH2)n-Het-C(O)—N(R1)(R2) set forth on column 1, line 41 to column 2 line 24 of U.S. Pat. No. 4,990,518 and the comparable disclosure in any member of the patent family of U.S. Pat. No. 4,990,518, which disclosure is herewith expressly incorporated by reference.

Typically, the compounds of this invention do not include the compound expressly disclosed in EP 76530, EP 1 162 196, EP 1132 381, U.S. Pat. No. 5,486,525, U.S. Pat. No. 5,137,896, U.S. Pat. No. 5,227,384, U.S. Pat. No. 4,914,108, U.S. Pat. No. 5,302,601, U.S. Pat. No. 5,208,242, U.S. Pat. No. 4,990,518, U.S. Pat. No. 4,988,707, DE 4211474, DE 4230464, WO 00/39127, WO 00/40586, WO 00/40583, WO 00/39127, WO 00/20416, WO99/27929, GB2158440, WO6111192, EP3444414, WO9516687, Chemical Abstracts acc no. 110:165603, Chemical Abstracts acc no. 132:22537—and any family member thereof in Chemical Abstracts acc no 1987:18435 and Chemical Abstracts acc no. 1983:594812 and overlap with the compounds described in the preset description, the disclosure of which is herewith expressly incorporated by reference.

Typically the compounds of this invention do not include the compounds expressly disclosed in EP 76530, EP 1 162 196, EP 1132 381, U.S. Pat. No. 5,486,525, U.S. Pat. No. 5,137,896, U.S. Pat. No. 5,227,384, U.S. Pat. No. 4,914,108, WO 00/39127, WO 00/40586, WO99/27929, GB2158440, WO6111192, EP3444414, WO9516687, Chemical Abstracts acc no. 1987:18435, Chemical Abstracts acc no. 110:165603, Chemical Abstracts acc no. 132:222537 and Chemical Abstracts acc no. 1983:594812 and over which the claims of this application are not novel or do not posses an inventive step; the disclosure of these compounds is herewith expressly incorporated by reference.

Typically the compounds of this invention do not include the compounds expressly disclosed in Justus Liebigs Annalen der Chemie (1971), 747, 158-171 or in the Journal of the Chemical Society [section B]: Physical Organic (1966), 4, 285-291 and over which the claims of this application are not novel or do not posses an inventive step; the disclosure of these compounds is herewith expressly incorporated by reference.

Optionally, the compounds of this invention include only those compounds wherein YR1 is none of the substituents designated R13 in column 5, lines 22-38 of U.S. Pat. No. 5,486,525 and/or R2 and/or R5 are none of the substituents collectively designated R14 and R15 in column 5, lines 38-53 of U.S. Pat. No. 5,486,525, which is herewith incorporated expressly by reference to the extent that such substituents overlap with those set forth herein.

According to a particular aspect the present invention relates to compounds of the formula (Z) and/or (A), described above wherein $R^1$ is a phenyl optionally substituted with a benzyloxy, and wherein $R^{19}$ at meta is phenyl optionally substituted with a halogen, (particularly chloro) in para, and $R^{19}$ at ortho is H, nitro, amino, mono- or di($C_{1-6}$ alkyl)-substituted amino, NHC(O)($C_{1-6}$ alkyl); methoxysulfonamide or C(O)$R^{22}$, wherein $R^{22}$ is $NR^{23}R^{24}$ as defined above. Optionally $R^{23}$ and $R^{24}$ are $C_{1-6}$ alkyl taken together with to form a hydroxy-substituted 6-membered saturated N-heterocyclic ring.

One embodiment of this second aspect of the present invention relates to compounds according to the general formula (I), pharmaceutically acceptable salts, tautomers, and isomers thereof, wherein:

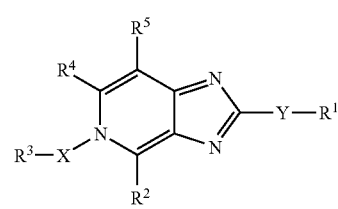

I wherein:
$R^1$ is selected from hydrogen; aryl unsubstituted or substituted with one or more $R^6$, heterocyclic ring unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, O; S(O)$_m$; $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, —O(CH$_2$)$_{1-5}$—, —(CH$_2$)$_{1-4}$—O—(CH$_2$)$_{1-4}$—, —S—(CH$_2$)$_{1-5}$—, —(CH$_2$)$_{1-4}$—S—(CH$_2$)$_{1-4}$—, —NR$^{11}$—(CH$_2$)$_{1-5}$—, —(CH$_2$)$_{1-4}$—NR$^{11}$—(CH$_2$)$_{1-4}$— and $C_{3-10}$ cycloalkylidene;

Each $R^2$ and $R^4$ is independently selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; NO$_2$; NR$^7$R$^8$; OCF$_3$; haloalkyl; C(=O)R$^9$; C(=S) R$^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —CH$_2$—, —CH(CH$_3$)—, —CH$_2$—CH$_2$—, —CH$_2$—CH$_2$—CH$_2$—, —CH$_2$—CH$_2$—CH$_2$), —(CH$_2$)$_{2-4}$—O—(CH$_2$)$_{2-4}$—, —(CH$_2$)$_{2-4}$—S—(CH$_2$)$_{2-4}$—, —(CH$_2$)$_{2-4}$—NR$^{10}$—(CH$_2$)$_{2-4}$—, $C_{3-10}$ cycloalkylidene, $C_{2-6}$ alkenylene (such as —CH=CH—CH$_2$—), $C_{2-6}$ alkynylene;

m is any integer from 0 to 2;

R³ is selected from the group consisting of aryl; aryloxy; arylthio; aryl-NR¹⁰—; 5 or 6 membered heterocyclic, oxyheterocyclic or thioheterocyclic ring; and each of said aryl, aryloxy, arylthio, aryl-NR¹⁰—, 5 or 6 membered heterocyclic, oxyheterocyclic or thioheterocyclic ring is optionally substituted with one or more R¹⁷; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

R⁵ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; NO₂; NR⁷R⁸; OCF₃; haloalkyl; C(=O)R⁹; C(=S)R⁹; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocyclic, oxyheterocyclic or thioheterocyclic ring;

Each R⁶ and R¹⁷ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; NO₂; NR⁷R⁸; OCF₃; haloalkyl; C(=O)R⁹; C(=S)R⁹; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more R¹⁹.

Each R⁷ and R⁸ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocyclic ring; C(=O)R¹²; C(=S)R¹²; an amino acid residue linked through a carboxyl group thereof; alternatively, R⁷ and R⁸, together with the nitrogen to which they are attached, combine to form a 5-6 membered heterocyclic ring;

Each R⁹ and R¹⁸ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; NR¹⁵R¹⁶; aryl an amino acid residue linked through an amino group thereof;

Each R¹⁰ and R¹¹ is independently selected from the group the group consisting of H; $C_{1-18}$ alkyl; $C_{1-18}$ alkenyl; $C_{3-10}$ cycloalkyl; $C_{4-10}$ cycloalkenyl; aryl; C(=O)R¹²; 5-6 membered heterocyclin ring; an amino acid residue linked through a carboxyl group thereof;

R¹² is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each R¹³ and R¹⁴ is independently selected from the group consisting of H; $C_{1-18}$ alkyl; $C_{2-18}$ alkenyl; aryl; $C_{3-10}$ cycloalkyl; $C_{4-10}$ cycloalkenyl; C(=O)R¹²; C(=S)R¹²; an amino acid residue linked through a carboxyl group thereof;

Each R¹⁵ and R¹⁶ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

R¹⁹ is independently selected from the group consisting of H; $C_{1-18}$ alkyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; NO₂; NR²⁰R²¹; OCF₃; haloalkyl; C(=O)R²²; C(=S)R²²; SH; C(=O)N($C_{1-6}$ alkyl), N(H)S(O)(O)($C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocyclic, oxyheterocyclic or thioheterocyclic ring each unsubstituted or substituted with 1 or more halogens;

Each R²⁰ and R²¹ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; C(=O)R¹², C(=S)R¹²;

R²² is independently selected from H; OH; $C_{1-18}$ alkyl; $C_{2-18}$ alkenyl; $C_{1-18}$ alkoxy; NR²³R²⁴; aryl; $C_{3-10}$ cycloalkyl,; $C_{1-10}$ cycloalkenyl;

Each R²³ and R²⁴ is independently selected from the group the group consisting of H; $C_{1-18}$ alkyl, preferably $C_{2-3}$ alkyl, wherein $C_{2-3}$ alkyl taken together with N of R²² can form a saturated heterocycle, which heterocycle is optionally substituted with OH or aryl or an amino acid residue.

According to another particular embodiment, the present invention relates to compounds according to the general formula (I), pharmaceutically acceptable salts, tautomers, and isomers thereof, wherein:

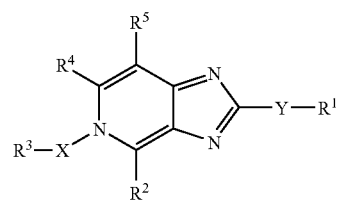

I

R¹ is selected from hydrogen; phenyl unsubstituted or substituted with 1-3 R⁶; 5 or 6 membered heterocyclic ring, optionally benzo-added, containing 1-3 heteroatoms selected from the group O, N, and S, unsubstituted or substituted with 1-2 R⁶; 1-naphthyl unsubstituted or substituted with 1-3 R⁶; 2-naphthyl unsubstituted or substituted with 1-3 R⁶; $C_{3-10}$ cycloalkyl, particularly $C_{3-7}$ cycloalkyl; $C_{5-7}$ cycloalkenyl with the proviso that the double bond cannot be adjacent to a nitrogen;

Y is selected from the group —(CH₂)₀₋₆—; O; S; NR¹¹; —CH(CH₃)—; —OCH₂—; —CH₂O—; —OCH₂—CH₂—; —CH₂—CH₂O—; —CH₂—O—CH₂—; —(CH₂)₀₋₅—S—; —S—(CH₂)₀₋₅—; —(CH₂)₀₋₂—S—(CH₂)₀₋₂—; —NR¹¹—(CH₂)₀₋₅—; —(CH₂)₀₋₅—NR¹¹—; —CH₂—NR¹¹—CH₂—; —C(CH₃)₂—; (cis or trans) —CH₂—CH=CH—; (cis or trans) —CH=CH—CH₂—;

Each R², R⁴ and R⁵ is independently selected from hydrogen; straight or branched $C_{1-18}$ alkoxy, particularly $C_{1-6}$ alkoxy; straight or branched $C_{1-18}$ alkyl particularly $C_{1-6}$ alkyl; F; Cl; Br; I; OH; CN; NO₂; NR⁷R⁸; OCF₃; CF₃; C(=O)R⁹; phenyl; phenoxy; benzyl; hydroxymethyl;

X is selected from the group —CH₂—; —CH(CH₃)—; —CH₂—CH₂—; —CH₂—CH₂—CH₂—; —CH₂—CH₂—CH₂—CH₂; —OCH₂—CH₂—; —SCH₂—CH₂—; —NR¹⁰—CH₂—CH₂—; $C_{3-7}$ cycloalkylidene;

—C(CH$_3$)$_2$—; —CH$_2$—CH(CH$_3$)—CH$_2$—; —CH(CH$_3$)—CH$_2$—CH$_2$—; —CH$_2$—CH$_2$—CH(CH$_3$)—; —CH=CH—CH$_2$—;

$R^3$ is selected from unsubstituted or phenyl substituted with 1-3 $R^{17}$; 5 or 6 membered heterocyclic ring, containing 1-3 heteroatoms selected from the group O, N, and S, unsubstituted or substituted with 1-2 $R^{17}$; 1-naphthyl unsubstituted or substituted with 1-3 $R^{17}$; 2-naphthyl unsubstituted or substituted with 1-3 $R^{17}$; $C_{3-10}$ cycloalkyl, particularly $C_{3-7}$ cycloalkyl; $C_{5-7}$ cycloalkenyl with the proviso that the double bond cannot be adjacent to a nitrogen;

Each $R^6$ and $R^{17}$ is independently selected from the group H; straight or branched $C_{1-6}$ alkoxy; straight or branched $C_{1-6}$ alkyl; F; Cl; Br; I; OH; CN; NO$_2$; NR$^{13}$R$^{14}$; OCF$_3$; CF$_3$; C(=O)R$^{18}$; unsubstituted phenyl or phenyl substituted with 1-3 $R^{19}$; 5 or 6 membered heterocycles, optionally benzo-added, containing 1-3 heteroatoms selected from O, N and S, unsubstituted or substituted with 1 or 2 $R^{19}$; 2-naphthyl unsubstituted or substituted with 1-3 $R^{19}$; $C_{3-7}$ cycloalkyl; $C_{5-7}$ cycloalkenyl, phenoxy; benzyl; hydroxymethyl;

Each $R^7$ and $R^8$ is independently selected from H; straight or branched $C_{1-18}$ alkyl, preferably $C_{1-6}$ alkyl; phenyl; C(=O)R$^{12}$; alternatively, $R^7$ and $R^8$, together with the nitrogen to which they are attached, combine to form a 5-6 membered ring;

Each $R^9$ and $R^{18}$ is independently selected from H; OH; straight or branched $C_{1-18}$ alkyl, preferably $C_{1-6}$ alkyl; straight or branched $C_{1-18}$ alkoxy, preferably $C_{1-6}$ alkoxy; NR$^{15}$R$^{16}$; phenyl;

Each $R^{10}$ and $R^{11}$ is independently selected from the group H; $C_{1-18}$ alkyl, preferably $C_{1-6}$ straight or branched alkyl; phenyl;

Each $R^{12}$ is selected from the group H; $C_{1-18}$ alkyl, preferably $C_{1-6}$ straight or branched alkyl; phenyl;

Each $R^{13}$ and $R^{14}$ is independently selected from H; straight or branched $C_{1-18}$ alkyl, preferably $C_{1-6}$ alkyl; phenyl; C(=O)R$^{12}$;

Each $R^{15}$ and $R^{16}$ is independently selected from the group H; $C_{1-6}$ straight or branched alkyl; phenyl;

$R^{19}$ is selected from the group H; straight or branched $C_{1-6}$ alkoxy; straight or branched $C_{1-6}$ alkyl; F; Cl, Br; OH; NO2; NR$^{20}$R$^{21}$; OCF3, C(=O)R$^{22}$; phenyl; phenoxy; benzyl; hydroxymethyl;

Each $R^{20}$ and $R^{21}$ is independently selected from H; straight or branched $C_{1-18}$ alkyl, preferably $C_{1-6}$ alkyl; phenyl; C(=O)R$^{12}$;

$R^{22}$ is selected from H; OH; straight or branched $C_{1-6}$ alkyl; straight or branched $C_{1-18}$ alkoxy, preferably $C_{1-6}$ alkoxy; NR$^{23}$R$^{24}$; phenyl;

Each $R^{23}$ and $R^{24}$ is independently selected from the group H; $C_{1-18}$ alkyl, preferably $C_{1-6}$ straight or branched alkyl; phenyl.

Another embodiment of present invention relates to compounds of formula (II), which are related to the general Formula (I), but wherein $R^1$ is directly linked to the imidazo[4,5-c]pyridine ring structure, pharmaceutically acceptable salts, tautomers, and isomers thereof and their use in a treatment of viral infection or to manufacture a medicament to treat viral infections, wherein:

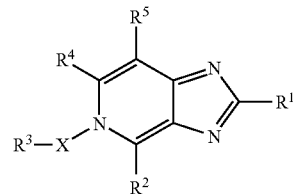

$R^1$ is selected from phenyl substituted with 0-3 $R^6$; 5 or 6 membered heterocyclic ring containing 1-3 heteroatoms selected from the group O, N, and S, substituted with 0-2 $R^6$; 1-naphthyl substituted with 0-3 $R^6$; 2-naphthyl substituted with 0-3 $R^6$; $C_{3-7}$ cycloalkyl; $C_{4-5-710}$ cycloalkenyl;

$R^2$, $R^4$ and $R^5$ are independently selected from hydrogen; straight or branched $C_{1-6}$ alkoxy; straight or branched $C_{1-6}$ alkyl; F; Cl; Br; I; OH; CN; NO$_2$; NR$^7$R$^8$; OCF$_3$; CF$_3$; C(=O)R$^9$; phenyl; phenoxy; benzyl; hydroxymethyl;

X is selected from the group —CH$_2$—; —CH(CH$_3$)—; —CH$_2$—CH$_2$—; —CH$_2$—CH$_2$—CH$_2$—; —CH$_2$—CH$_2$—CH$_2$—CH$_2$; —OCH$_2$—CH$_2$—; —SCH$_2$—CH$_2$—; —NR$^{10}$—CH$_2$—CH$_2$—; $C_{3-7}$ cycloalkylidene; —C(CH$_3$)$_2$; —CH$_2$—CH(CH$_3$)—CH$_2$—; —CH(CH$_3$)—CH$_2$—CH$_2$—; —CH$_2$—CH$_2$—CH(CH$_3$)—; —CH=CH—CH$_2$—;

$R^3$ is selected from phenyl substituted with 0-3 $R^{17}$; (benzoannellated) 5 or 6 membered aromatic heterocyclic ring containing 1-3 heteroatoms selected from the group O, N, and S, substituted with 0-2 $R^{17}$; 1-naphthyl substituted with 0-3 $R^{17}$; 2-naphthyl substituted with 0-3 $R^{17}$; $C_{3-7}$ cycloalkyl; $C_{4-10}$ cycloalkenyl with the proviso that the double bond cannot be adjacent to a nitrogen;

$R^6$ and $R^{17}$ are independently selected from the group H; straight or branched $C_{1-6}$ alkoxy; straight or branched $C_{1-6}$ alkyl; F; Cl; Br; I; OH; CN; NO$_2$; NR$^{13}$R$^{14}$; OCF$_3$; CF$_3$; C(=O)R$^{18}$; phenyl; phenoxy; benzyl; hydroxymethyl;

$R^7$ and $R^8$ are independently selected from H; straight or branched $C_{1-6}$ alkyl; phenyl; C(=O)R$^{12}$ or $R^7$ and $R^8$, together with the nitrogen to which they are attached, combine to form a 5-6 membered ring;

$R^9$ and $R^{18}$ are independently selected from H; OH; straight or branched $C_{1-6}$ alkyl; straight or branched $C_{1-6}$ alkoxy; NR$^{15}$R$^{16}$; phenyl;

$R^{10}$ is selected from the group H; $C_{1-6}$ straight or branched alkyl; phenyl;

$R^{12}$ is selected from the group H; $C_{1-6}$ straight or branched alkyl; phenyl;

$R^{13}$ and $R^{14}$ are independently selected from H; straight or branched $C_{1-6}$ alkyl; phenyl; C(=O)R$^{12}$;

$R^{15}$ and $R^{16}$ are independently selected from the group H; $C_{1-6}$ straight or branched alkyl; phenyl;

Another embodiment of the present invention relates to compounds of formula (II), pharmaceutically acceptable salts, tautomers, and isomers thereof and their use in a treatment of viral infection or to manufacture a medicament to treat viral infection, wherein:

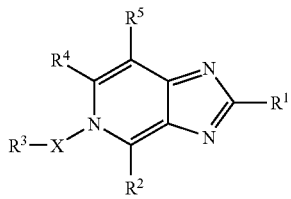

$R^1$ is selected from phenyl substituted with 0-3 $R^6$; 5 or 6 membered heterocyclic ring containing 1-3 heteroatoms selected from the group O, N, and S, substituted with 0-2 $R^6$; 1-naphthyl substituted with 0-3 $R^6$; 2-naphthyl substituted with 0-3 $R^6$; $C_{3-7}$ cycloalkyl; $C_{45-7-10}$ cycloalkenyl;

$R^2$, $R^4$ and $R^5$ are independently selected from hydrogen; straight or branched $C_{1-6}$ alkoxy; straight or branched $C_{1-6}$ alkyl; F; Cl; Br; I; OH; CN; $NO_2$; $NR^7R^8$; $OCF_3$; $CF_3$; C(=O)$R^9$; phenyl; phenoxy; benzyl; hydroxymethyl;

X is selected from the group —$CH_2$—; —$CH(CH_3)$—; —$CH_2$—$CH_2$—$CH_2$—; —$OCH_2$—$CH_2$—; —CH=CH—$CH_2$—;

$R^3$ is selected from phenyl substituted with 0-3 $R^{17}$; (benzoannellated) 5 or 6 membered aromatic heterocyclic ring containing 1-3 heteroatoms selected from the group O, N, and S, substituted with 0-2 $R^{17}$; 1-naphthyl substituted with 0-3 $R^{17}$; 2-naphthyl substituted with 0-3 $R^{17}$; $C_{3-7}$ cycloalkyl; $C_{4-7}$ cycloalkenyl with the proviso that the double bond cannot be adjacent to a nitrogen;

$R^6$ and $R^{17}$ are independently selected from the group H; straight or branched $C_{1-6}$ alkoxy; straight or branched $C_{1-6}$ alkyl; F; Cl; Br; I; OH; CN; $NO_2$; $NR^{13}R^{14}$; $OCF_3$; $CF_3$; C(=O)$R^{18}$; phenyl; phenoxy; benzyl; hydroxymethyl;

$R^7$ and $R^8$ are independently selected from H; straight or branched $C_{1-6}$ alkyl; phenyl; C(=O)$R^{12}$; alternatively, $R^7$ and $R^8$, together with the nitrogen to which they are attached, combine to form a 5-6 membered ring;

$R^9$ and $R^{18}$ are independently selected from H; OH; straight or branched $C_{1-6}$ alkyl; straight or branched $C_{1-6}$ alkoxy; $NR^{15}R^{16}$; phenyl;

$R^{12}$ is selected from the group H; $C_{1-6}$ straight or branched alkyl; phenyl;

$R^{13}$ and $R^{14}$ are independently selected from H; straight or branched $C_{1-6}$ alkyl; phenyl; C(=O)$R^{12}$;

$R^{15}$ and $R^{16}$ are independently selected from the group H; $C_{1-6}$ straight or branched alkyl; phenyl;

Another embodiment of present invention relates to compounds of formula (II), pharmaceutically acceptable salts, tautomers, and isomers and their use in a treatment of viral infection or to manufacture a medicament to treat viral infection, wherein:

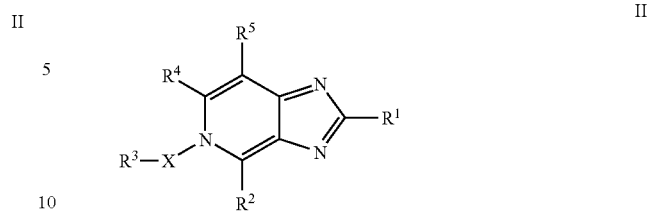

$R^1$ is selected from phenyl unsubstituted or substituted with 1-3 $R^6$; 5 or 6 membered heterocyclic ring containing 1-3 heteroatoms selected from the group O, N, and S, unsubstituted or substituted with 1-2 $R^6$; 1-naphthyl unsubstituted or substituted with 1-3 $R^6$; 2-naphthyl unsubstituted or substituted with 1-3 $R^6$; $C_{3-7}$ cycloalkyl; $C_{5-7}$ cycloalkenyl;

$R^2$, $R^4$ and $R^5$ are hydrogen;

X is selected from the group —$CH_2$—; —$CH(CH_3)$—; —$CH_2$—$CH_2$—$CH_2$—; —$OCH_2$—$CH_2$—; —CH=CH—$CH_2$—;

$R^3$ is selected from phenyl unsubstituted or substituted with 1-3 $R^{17}$; (benzoannellated) 5 or 6 membered aromatic heterocyclic ring containing 1-3 heteroatoms selected from the group O, N, and S, unsubstituted or substituted with 1-2 $R^{17}$; 1-naphthyl unsubstituted or substituted with 1-3 $R^{17}$; 2-naphthyl substituted with 0-3 $R^{17}$; $C_{3-7}$ cycloalkyl; $C_{5-7}$ cycloalkenyl with the proviso that the double bond cannot be adjacent to a nitrogen;

Each $R^6$ and $R^{17}$ is independently selected from the group H; straight or branched $C_{1-6}$ alkoxy; straight or branched $C_{1-6}$ alkyl; F; Cl; Br; I; OH; CN; $NO_2$; $NR^{13}R^{14}$; $OCF_3$; $CF_3$; C(=O)$R^9$; phenyl; phenoxy; benzyl; hydroxymethyl;

$R^9$ is selected from H; OH; straight or branched $C_{1-6}$ alkyl; straight or branched $C_{1-6}$ alkoxy; $NR^{15}R^{16}$; phenyl;

Each $R^{13}$ and $R^{14}$ is independently selected from H; straight or branched $C_{1-6}$ alkyl; phenyl; C(=O)$R^{12}$;

Each $R^{15}$ and $R^{16}$ is independently selected from the group H; $C_{1-6}$ straight or branched alkyl; phenyl;

Yet another embodiment of present invention comprises the compounds of formula (II), pharmaceutically acceptable salts, tautomers, and isomers thereof and their use in a treatment of viral infection or to manufacture a medicament to treat viral infection, wherein:

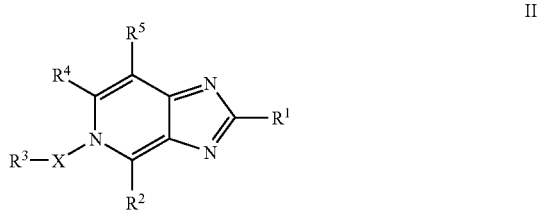

$R^1$ is selected from phenyl unsubstituted or substituted with 1-3 $R^6$; 5 or 6 membered heterocyclic ring containing 1-3 heteroatoms selected from the group O, N, and S, unsubstituted or substituted with 1-2 $R^6$; 1-naphthyl unsubstituted or substituted with 1-3 $R^6$; 2-naphthyl unsubstituted or substituted with 1-3 $R^6$;

$R^2$, $R^4$ and $R^5$ are hydrogen;

X is selected from —$CH_2$—; —$CH(CH_3)$—; —$CH_2$—$CH_2$—$CH_2$—; —$OCH_2$—$CH_2$—; —CH=CH—$CH_2$—;

$R^3$ is selected from phenyl unsubstituted or substituted with 1-3 $R^{17}$; 5 or 6 membered aromatic heterocyclic ring containing 1-3 heteroatoms selected from the group O, N, and S, unsubstituted or substituted with 1-3 $R^{17}$; 1-naphthyl unsubstituted or substituted with 1-3 $R^{17}$; 2-naphthyl unsubstituted or substituted with 1-3 $R^{17}$;

Each $R^6$ and $R^{17}$ is independently selected from the group H; straight or branched $C_{1-6}$ alkoxy; straight or branched $C_{1-6}$ alkyl; F; Cl; Br; I; OH; CN; $NO_2$; $NR^{13}R^{14}$; $OCF_3$; $CF_3$; C(=O)$R^9$; phenyl; phenoxy; benzyl; hydroxymethyl;

$R^9$ is selected from H; OH; straight or branched $C_{1-6}$ alkyl; straight or branched $C_{1-6}$ alkoxy; $NR^{15}R^{16}$; phenyl;

Each $R^{13}$ and $R^{14}$ is independently selected from H; straight or branched $C_{1-6}$ alkyl; phenyl; C(=O)$R^{12}$;

Each $R^{15}$ and $R^{16}$ is independently selected from the group H; $C_{1-6}$ straight or branched alkyl; phenyl.

Particularly, the second embodiment of present invention comprises compounds of formula (II), pharmaceutically acceptable salts, tautomers, and isomers thereof and their use in a treatment of viral infection or to manufacture a medicament to treat viral infection, wherein:

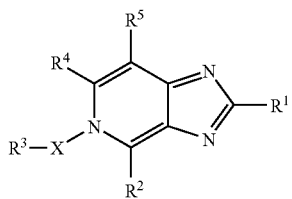

II $R^1$ is selected from phenyl unsubstituted or substituted with 1-3 $R^6$; 5 or 6 membered heterocyclic ring containing 1-3 heteroatoms selected from the group O, N, and S, unsubstituted or substituted with 1-2 $R^6$; 1-naphthyl unsubstituted or substituted with 1-3 $R^6$; 2-naphthyl unsubstituted or substituted with 1-3 $R^6$;

$R^2$, $R^4$ and $R^5$ are hydrogen;

X is selected from —$CH_2$—; —$CH(CH_3)$—; —$CH_2$—$CH_2$—$CH_2$—; —$OCH_2$—$CH_2$—; —CH=CH—$CH_2$—;

$R^3$ is selected from phenyl unsubstituted or substituted with 1-3 $R^{17}$; 5 or 6 membered aromatic heterocyclic ring containing 1-3 heteroatoms selected from the group O, N, and S, unsubstituted or substituted with 1-2 $R^{17}$; 1-naphthyl substituted with 0-3 $R^{17}$; 2-naphthyl unsubstituted or substituted with 1-3 $R^{17}$;

Each $R^6$ and $R^{17}$ is independently selected from hydrogen; straight or branched $C_{1-6}$ alkoxy; straight or branched $C_{1-6}$ alkyl; F; Cl; Br; I; OH; CN; $NO_2$; $NR^{13}R^{14}$; $OCF_3$; $CF_3$; C(=O)$R^9$; phenyl; phenoxy; benzyl; hydroxymethyl;

$R^9$ is selected from H; OH; straight or branched $C_{1-6}$ alkyl; straight or branched $C_{1-6}$ alkoxy; $NR^{15}R^{16}$; phenyl;

Each $R^{13}$ and $R^{14}$ is independently selected from H; straight or branched $C_{1-6}$ alkyl; phenyl; C(=O)$R^{12}$;

Each $R^{15}$ and $R^{16}$ is independently selected from the group H; $C_{1-6}$ straight or branched alkyl; phenyl;

A further embodiment of the present invention relates to compounds of the formula III:

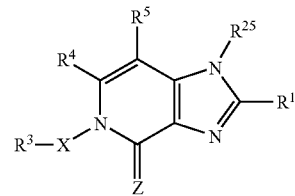

III or a pharmaceutically acceptable acid addition salt thereof wherein:

$R^1$ is selected from hydrogen; aryl unsubstituted or substituted with one or more $R^6$, heterocyclic ring unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, O; S(O)$_m$; $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, —O($CH_2$)$_{1-5}$—, —($CH_2$)$_{1-4}$—O—($CH_2$)$_{1-4}$—, —S—($CH_2$)$_{1-5}$—, —($CH_2$)$_{1-4}$—S—($CH_2$)$_{1-4}$—, —$NR^{11}$—($CH_2$)$_{1-5}$—, —($CH_2$)$_{1-4}$—$NR^{11}$—($CH_2$)$_{1-4}$— and $C_{3-10}$ cycloalkylidene;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —$CH_2$—, —$CH(CH_3)$—, —$CH_2$—$CH_2$—, —$CH_2$—$CH_2$—$CH_2$—, —$CH_2$—$CH_2$—$CH_2$—$CH_2$—), —($CH_2$)$_{2-4}$—O—($CH_2$)$_{2-4}$—, —($CH_2$)$_{2-4}$—S—($CH_2$)$_{2-4}$—, —($CH_2$)$_{2-4}$—$NR^{10}$—($CH_2$)$_{2-4}$—, $C_{3-10}$ cycloalkylidene, $C_{2-6}$ alkenylene (such as —CH=CH—$CH_2$—), $C_{2-6}$ alkynylene;

m is any integer from 0 to 2;

$R^3$ is selected from the group consisting of aryl; aryloxy; arylthio; aryl-$NR^{10}$—; 5 or 6 membered heterocyclic, oxyheterocyclic or thioheterocyclic ring; and each of said aryl, aryloxy, arylthio, aryl-$NR^{10}$—, 5 or 6 membered heterocyclic, oxyheterocyclic or thioheterocyclic ring is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^4$ is independently selected from the group consisting of hydrogen $C_{1-18}$ alkyl; $C_{2-18}$ alkenyl; $C_{2-18}$ alkylenyl; $C_{1-8}$ alkoxy; $C_{1-18}$ alkylthio; halogen; OH; CN; $NO_2$; $NR^7R^8$; $OCF_3$; haloalkyl; C(=O)$R^9$; C(=S)$R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring;

$R^5$ is independently selected from the group consisting of hydrogen; $C_{1-18}$ alkyl; $C_{2-18}$ alkenyl; $C_{2-18}$ alkynyl;

$C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocyclic, oxyheterocyclic or thioheterocyclic ring;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$;

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocyclic ring; $C(=O)R^{12}$; $C(=S) R^{12}$; an amino acid residue linked through a carboxyl group thereof; alternatively, $R^7$ and $R^8$, together with the nitrogen to which they are attached, combine to form a 5-6 membered heterocyclic ring;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; $C(=O)R^{12}$; 5-6 membered heterocyclin ring; an amino acid residue linked through a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each $R^{13}$ and $R^{14}$ is independently selected from the group consisting of H; $C_{1-18}$ alkyl; $C_{2-18}$ alkenyl; aryl; $C_{3-10}$ cycloalkyl; $C_{4-10}$ cycloalkenyl; $C(=O)R^{12}$; $C(=S)R^{12}$; an amino acid residue linked through a carboxyl group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$ alkyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocyclic, oxyheterocyclic or thioheterocyclic ring each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R$, $C(=S)R^{12}$;

$R^{22}$ is independently selected from H; OH; $C_{1-18}$ alkyl; $C_{2-18}$ alkenyl; $C_{1-18}$ alkoxy; $NR^{23}R^{24}$; aryl; $C_{3-10}$ cycloalkyl, $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Z is selected from (=O), (=S), and (=$NR^{27}$);

$R^{25}$ is selected from the group consisting of of H, $C_{1-18}$ alkyl, preferably $C_{1-4}$ alkyl; $C_{3-10}$ cycloalkyl, such as $C_{5-10}$ bicycloalkyl; $C_{3-10}$ cycloalkenyl; $(C_{3-8}$ cycloalkyl)-$C_{1-3}$ alkyl; aryl, such as phenyl; 5 or 6 membered heterocyclic ring, such as pyridyl; alkylaryl, such as benzyl; and each of said $C_{1-18}$ alkyl, preferably $C_{1-4}$ alkyl, $C_{3-10}$ cycloalkyl, $C_{3-10}$ cycloalkenyl, $(C_{3-8}$ cycloalkyl)-$C_{1-3}$ alkyl, $C_{5-10}$ bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocyclic ring having 3 to 7 carbon atoms, preferably a saturated heterocyclic ring wherein the heteroatoms are S, S(O), or $S(O)_2$ separated from the imidazopyridyl ring nitrogen atom by at least 2 heterocyclic ring carbon atoms. Typically $R^{25}$ is cyclopentyl or cyclohexyl;

$R^{27}$ is selected from the group consisting of H, $C_{1-18}$ alkyl, $C_{3-10}$ cycloalkyl, $(C_{3-10}$ cycloalkyl)-$C_{1-6}$ alkyl; aryl; arylalkyl, such as benzyl.

And pharmaceutical compositions thereof as antiviral drugs.

Another particular embodiment of the present invention relates to compounds of the formula IV:

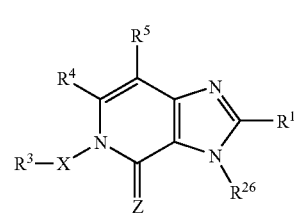

IV or a pharmaceutically acceptable acid addition salt thereof: wherein $R^1$ is selected from hydrogen; aryl unsubstituted or substituted with one or more $R^6$, heterocyclic ring unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, O; $S(O)_m$; $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, $-O(CH_2)_{1-5}-$, $-(CH_2)_{1-4}-O-(CH_2)_{1-4}$, $-S-(CH_2)_{1-5}-$, $-(CH_2)_{1-4}-S-(CH_2)_{1-4}-$, $-NR^{11}-(CH_2)_{1-5}-$, $-(CH_2)_{1-4}-NR^{11}-(CH_2)_{1-4}-$ and $C_{3-10}$ cycloalkylidene;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —$CH_2$—, —$CH(CH_3)$—, —$CH_2$—$CH_2$—, —$CH_2$—$CH_2$—$CH_2$—, —$CH_2$—$CH_2$—$CH_2$—$CH_2$), —$(CH_2)_{2-4}$—O—$(CH_2)_{2-4}$—, —$(CH_2)_{2-4}$—S—$(CH_2)_{2-4}$—, —$(CH_2)_{2-4}$—$NR^{10}$—$(CH_2)_{2-4}$—, $C_{3-10}$ cycloalkylidene, $C_{2-6}$ alkenylene (such as —CH=CH—$CH_2$—), $C_{2-6}$ alkynylene;

m is any integer from 0 to 2;

$R^3$ is selected from the group consisting of aryl; aryloxy; arylthio; aryl-$NR^{10}$—; 5 or 6 membered heterocyclic, oxyheterocyclic or thioheterocyclic ring; and each of said aryl, aryloxy, arylthio, aryl-$NR^{10}$—, 5 or 6 membered heterocyclic, oxyheterocyclic or thioheterocyclic ring is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^4$ is independently selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; C(=O)$R^9$; C(=S)$R^9$; SH; aryl; aryloxy; arylthio; arylalkyl; $C_{1-18}$ hydroxyalkyl; $C_{3-10}$ cycloalkyl; $C_{3-10}$ cycloaLkyloxy; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring;

$R^5$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; C(=O)$R^9$; C(=S)$R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocyclic, oxyheterocyclic or thioheterocyclic ring;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; C(=O)$R^9$; C(=S)$R^9$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ is hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$;

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocyclic ring; C(=O)$R^{12}$; C(=S)$R^{12}$; an amino acid residue linked through a carboxyl group thereof; alternatively, $R^7$ and $R^8$, together with the nitrogen to which they are attached, combine to form a 5-6 membered heterocyclic ring;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl an amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; C(=O)$R^{12}$; 5-6 membered heterocyclin ring; an amino acid residue linked through a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each $R^{13}$ and $R^{14}$ is independently selected from the group consisting of H; $C_{1-18}$ alkyl; $C_{2-18}$ alkenyl; aryl; $C_{3-10}$ cycloalkyl; $C_{4-10}$ cycloalkenyl; C(=O)$R^{12}$; C(=S)$R^{12}$; an amino acid residue linked through a carboxyl group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$ alkyl, preferably $C_{1-6}$ alkyl; $C_{2-18}$ alkenyl; $C_{2-18}$ alkynyl; $C_{1-18}$ is alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; C(=O)$R^{22}$; C(=S)$R^{22}$; SH; C(=O)N($C_{1-6}$ alkyl), N(H)S(O)(O)($C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocyclic, oxyheterocyclic or thioheterocyclic ring each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; C(=O)$R^{12}$, C(=S)$R^{12}$;

$R^{22}$ is independently selected from H; OH; $C_{1-18}$ alkyl; $C_{2-18}$ alkenyl; $C_{1-18}$ alkoxy; $NR^{23}R^{24}$; aryl; $C_{3-10}$ cycloalkyl,; $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Z is selected from (=O), (=S), and (=$NR^{27}$);

$R^{26}$ is selected from the group consisting of of H, $C_{1-18}$ alkyl, preferably $C_{1-4}$ alkyl; $C_{3-10}$ cycloalkyl, such as $C_{5-10}$ bicycloalkyl; $C_{3-10}$ cycloalkenyl; ($C_{3-8}$ cycloalkyl)-$C_{1-3}$ alkyl; aryl, such as phenyl; 5 or 6 membered heterocyclic ring, such as pyridyl; alkylaryl, such as benzyl; and each of said $C_{1-18}$ alkyl, preferably $C_{1-4}$ alkyl, $C_{3-10}$ cycloalkyl, $C_{3-10}$ cycloalkenyl, ($C_{3-8}$ cycloalkyl)-$C_{1-3}$ alkyl, $C_{5-10}$ bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocyclic ring having 3 to 7 carbon atoms, preferably a saturated heterocyclic ring wherein the heteroatoms are S, S(O), or S(O)$_2$ separated from the imidazopyridyl ring nitrogen atom by at least 2 heterocyclic ring carbon atoms. Typically $R^{26}$ is cyclopentyl or cyclohexyl;

$R^{27}$ is selected from the group consisting of H, $C_{1-18}$ alkyl, $C_{3-10}$ cycloalkyl, ($C_{3-10}$ cycloalkyl)-$C_{1-6}$ alkyl; aryl; arylalkyl, such as benzyl;

and pharmaceutical compositions thereof as antiviral drugs.

A further optional embodiment of the present invention relates to compounds of the formula V:

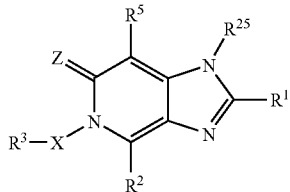

V or a pharmaceutically acceptable acid addition salt thereof: wherein $R^1$ is selected from hydrogen; aryl unsubstituted or substituted with one or more $R^6$, heterocyclic ring unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, O; $S(O)_m$; $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, —O(CH$_2$)$_{1-5}$—, —(CH$_2$)$_{1-4}$—O—(CH$_2$)$_{1-4}$—, —S—(CH$_2$)$_{1-5}$—, —(CH$_2$)$_{1-4}$—S—(CH$_2$)$_{1-4}$—, —NR$^{11}$—(CH$_2$)$_{1-5}$—, —(CH$_2$)$_{1-4}$—NR$^{11}$—(CH$_2$)$_{1-4}$— and $C_{3-10}$ cycloalkylidene;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —CH$_2$—, —CH(CH$_3$)—, —CH$_2$—CH$_2$—, —CH$_2$—CH$_2$—CH$_2$—, —CH$_2$—CH$_2$—CH$_2$—CH$_2$), —(CH$_2$)$_{2-4}$—O—(CH$_2$)$_{2-4}$—, —(CH$_2$)$_{2-4}$—S—(CH$_2$)$_{2-4}$—, —(CH$_2$)$_{2-4}$—NR$^{10}$—(CH$_2$)$_{2-4}$—, $C_{3-10}$ cycloalkylidene, $C_{2-6}$ alkenylene (such as —CH=CH—CH$_2$—), $C_{2-6}$ alkynylene;

m is any integer from 0 to 2;

$R^2$ is selected from the group consisting of hydrogen $C_{1-18}$ alkyl; $C_{2-18}$ alkenyl; $C_{2-18}$ alkyl; $C_{1-18}$ alkoxy; $C_{1-18}$ alkylthio; halogen; OH; CN; NO$_2$; NR$^7$R$^8$; OCF$_3$; haloalkyl; C(=O)R$^9$; C(=S)R$^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring;

$R^3$ is selected from the group consisting of aryl; aryloxy; arylthio; aryl-NR$^{10}$—; 5 or 6 membered heterocyclic, oxyheterocyclic or thioheterocyclic ring; and each of said aryl, aryloxy, arylthio, aryl-NR$^{10}$—, 5 or 6 membered heterocyclic, oxyheterocyclic or thioheterocyclic ring is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^5$ is selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; NO$_2$; NR$^7$R$^8$; OCF$_3$; haloalkyl; C(=O)R$^9$; C(=S)R$^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocyclic, oxyheterocyclic or thioheterocyclic ring;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; NO$_2$; NR$^7$R$^8$; OCF$_3$; haloalkyl; C(=O)R$^9$; C(=S) R$^9$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$;

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocyclic ring; C(=O)R$^{12}$; C(=S) R$^{12}$; an amino acid residue linked through a carboxyl group thereof; alternatively, $R^7$ and $R^8$, together with the nitrogen to which they are attached, combine to form a 5-6 membered heterocyclic ring;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; NR$^{15}$R$^{16}$; aryl an amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; C(=O)R$^{12}$; 5-6 membered heterocyclin ring; an amino acid residue linked through a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each $R^{13}$ and $R^{14}$ is independently selected from the group consisting of H; $C_{1-18}$ alkyl; $C_{2-18}$ alkenyl; aryl; $C_{3-10}$ cycloalkyl; $C_{4-10}$ cycloalkenyl; C(=O)R$^{12}$; C(=S)R$^{12}$; an amino acid residue linked through a carboxyl group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$ alkyl, preferably $C_{1-6}$ alkyl; $C_{2-18}$ alkenyl; $C_{2-19}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; NO$_2$; NR$^{20}$R$^{21}$; OCF$_3$; haloalkyl; C(=O)R$^{22}$; C(=S)R$^{22}$; SH; C(=O)N(C$_{1-6}$ alkyl), N(H)S(O)(O)(C$_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocyclic, oxyheterocyclic or thioheterocyclic ring each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R^{12}$, $C(=S)R^{12}$;

$R^{22}$ is independently selected from H; OH; $C_{1-18}$ alkyl; $C_{2-18}$ alkenyl; $C_{1-18}$ alkoxy; $NR^{23}R^{24}$; aryl; $C_{3-10}$ cycloalkyl, $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Z is selected from (=O), (=S), and (=$NR^{27}$);

$R^{25}$ is selected from the group consisting of of H, $C_{1-18}$ alkyl, preferably $C_{1-4}$ alkyl; $C_{3-10}$ cycloalkyl, such as $C_{5-10}$ bicycloalkyl; $C_{3-10}$ cycloalkenyl; ($C_{3-8}$ cycloalkyl)-$C_{1-3}$ alkyl; aryl, such as phenyl; 5 or 6 membered heterocyclic ring, such as pyridyl; alkylaryl, such as benzyl; and each of said $C_{1-18}$ alkyl, preferably $C_{1-4}$ alkyl, $C_{3-10}$ cycloalkyl, $C_{3-10}$ cycloalkenyl, ($C_{3-8}$ cycloalkyl)-$C_{1-3}$ alkyl, $C_{5-10}$ bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocyclic ring having 3 to 7 carbon atoms, preferably a saturated heterocyclic ring wherein the heteroatoms are S, S(O), or S($O_2$ separated from the imidazopyridyl ring nitrogen atom by at least 2 heterocyclic ring carbon atoms. Typically $R^{25}$ is cyclopentyl or cyclohexyl;

$R^{27}$ is selected from the group consisting of H, $C_{1-18}$ alkyl, $C_{3-10}$ cycloalkyl, ($C_{3-10}$ cycloalkyl)-$C_{1-6}$ alkyl; aryl; arylalkyl, such as benzyl;

and pharmaceutical compositions thereof as antiviral drugs.

A further optional embodiment of the present invention relates to compounds of the formula VI:

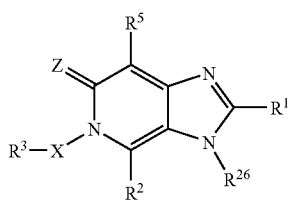

VI or a pharmaceutically acceptable acid addition salt thereof wherein $R^1$ is selected from hydrogen; aryl unsubstituted or substituted with one or more $R^6$, heterocyclic ring unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, O; $S(O)_m$; $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, —O($CH_2)_{1-5}$—, —($CH_2)_{1-4}$—O—($CH_2)_{1-4}$—, —S—($CH_2)_{1-5}$—, —($CH_2)_{1-4}$—S—($CH_2)_{1-4}$—, —$NR^{11}$—($CH_2)_{1-5}$—, —($CH_2)_{1-4}$—$NR^{11}$—($CH_2)_{1-4}$— and $C_{3-10}$ cycloalkylidene;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —$CH_2$—, —$CH(CH_3)$—, —$CH_2$—$CH_2$—, —$CH_2$—$CH_2$—$CH_2$—, —$CH_2$—$CH_2$—$CH_2$—$CH_2$), —($CH_2)_{2-4}$—O—($CH_2)_{2-4}$—, —($CH_2)_{2-4}$—S—($CH_2)_{2-4}$—, —($CH_2)_{2-4}$—$NR^{10}$—($CH_2)_{2-4}$—, $C_{3-10}$ cycloalkylidene, $C_{2-6}$ alkenylene (such as —CH=CH—$CH_2$—), $C_{2-6}$ alkynylene;

m is any integer from 0 to 2;

$R^2$ is independently selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring;

$R^3$ is selected from the group consisting of aryl; aryloxy; arylthio; aryl-$NR^{10}$—; 5 or 6 membered heterocyclic, oxyheterocyclic or thioheterocyclic ring; and each of said aryl, aryloxy, arylthio, aryl-$NR^{10}$—, 5 or 6 membered heterocyclic, oxyheterocyclic or thioheterocyclic ring is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^5$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocyclic, oxyheterocyclic or thioheterocyclic ring;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; arylalkyloxy (optionally a oxybenzyl); arylalkylthio (optionally a benzylthio); 5 or 6 membered heterocyclic, oxyheterocyclic or thioheterocyclic ring; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocyclic, oxyheterocyclic or thioheterocyclic ring, $C_{1-18}$ hydroxyalkyl is optionally substituted with 1 or more $R^{19}$;

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocyclic ring; $C(=O)R^{12}$; $C(=S)R^{12}$; an amino acid residue linked through a carboxyl group thereof; alternatively, $R^7$ and $R^8$, together with the nitrogen to which they are attached, combine to form a 5-6 membered heterocyclic ring;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl an amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; $C(=O)R^{12}$; 5-6 membered heterocyclin ring; an amino acid residue linked through a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each $R^{13}$ and $R^{14}$ is independently selected from the group consisting of H; $C_{1-18}$ alkyl; $C_{2-18}$ alkenyl; aryl; $C_{3-10}$ cycloalkyl; $C_{4-10}$ cycloalkenyl; $C(=O)R^{12}$; $C(=S)R^{12}$; an amino acid residue linked through a carboxyl group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$ allyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocyclic, oxyheterocyclic or thioheterocyclic ring each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R^{12}$, $C(=S)R^{12}$;

$R^{22}$ is independently selected from H; OH; $C_{1-18}$ alkyl; $C_{2-18}$ alkenyl; $C_{1-18}$ alkoxy; $NR^{23}R^{24}$; aryl; $C_{3-10}$ cycloalkyl, $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Z is selected from ($=O$), ($=S$), and ($=NR^{27}$);

$R^{26}$ is selected from the group consisting of of H, $C_{1-18}$ alkyl, preferably $C_{1-4}$ alkyl; $C_{3-10}$ cycloalkyl, such as $C_{5-10}$ bicycloalkyl; $C_{3-10}$ cycloalkenyl; ($C_{3-8}$ cycloalkyl)-$C_{1-3}$ alkyl; aryl, such as phenyl; 5 or 6 membered heterocyclic ring, such as pyridyl; alkylaryl, such as benzyl; and each of said $C_{1-18}$ alkyl, preferably $C_{1-4}$ alkyl, $C_{3-10}$ cycloalkyl, $C_{3-10}$ cycloalkenyl, ($C_{3-8}$ cycloalkyl)-$C_{1-3}$ alkyl, $C_{5-10}$ bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocyclic ring having 3 to 7 carbon atoms, preferably a saturated heterocyclic ring wherein the heteroatoms are S, S(O), or $S(O)_2$ separated from the imidazopyridyl ring nitrogen atom by at least 2 heterocyclic ring carbon atoms. Typically $R^{26}$ is cyclopentyl or cyclohexyl;

$R^{27}$ is selected from the group consisting of H, $C_{1-18}$ alkyl, $C_{3-10}$ cycloalkyl, ($C_{3-10}$ cycloalkyl)-$C_{1-6}$ alkyl; aryl; arylalkyl, such as benzyl;

and pharmaceutical compositions thereof as antiviral drugs.

The present invention further relates to the use of a compound of formula (Z), optionally of the formula (A), (I), (II), (III), (IV), (V) and (VI) as a medicine, to the use of such compounds in the treatment of a viral infection or to manufacture a medicament to treat or prevent viral infection in a subject. The invention also relates to the use of a compound of formula (Z), optionally of the formula (A), (I), (II), (III), (IV), (V) and (VI) as a pharmaceutically active ingredient, especially as an inhibitor of the viral replication, more preferably as an inhibitor of the replication of a virus of the family of the Flaviviridae or the Picornaviridae, and yet more preferably as an inhibitor of the replication of BVDV, HCV or Coxsackie virus. Therefore, the invention also relates to the use of a compound of formula (Z), optionally of the formula (A), (I), (II), (III), (IV), (V) and (VI) for the manufacture of a medicine or a pharmaceutical composition having antiviral activity for the prevention and/or treatment of viral infections in humans and mammals.

The present invention further relates to a method of treatment of a viral infection in a mammal, including a human, comprising administering to the mammal in need of such treatment a therapeutically effective amount of a compound of formula (Z), more particularly of the formula (A), (I), (II), (III), (IV), (V) and (VI) as an active ingredient, optionally in a mixture with at least a pharmaceutically acceptable carrier.

The present invention further relates to a composition for separate, combined or sequential use in the treatment or prophylaxis of anti-viral infections, comprising:

a) one or more compounds according to the formula (Z) or optionally formula (A), (I), (II), (III), (IV), (V) and (VI), and b) one or more compounds effective in the treatment or prophylaxis of viral infections, including Flaviviral or Picornaviral enzyme inhibitors; in proportions such as to provide a synergistic effect in the said treatment of prophylaxis.

The invention further relates to methods for the preparation of compounds of formula (Z), optionally to methods for the preparation of compounds of the formula (A), (I), (II), (III), (IV), (V) and (VI) as detailed above, more particularly to methods for the preparation of the compounds specifically disclosed herein, to pharmaceutical compositions comprising them in admixture with at least a pharmaceutically acceptable carrier, the active ingredient optionally being in a concentration range of about 0.1-100% by weight, and to the use of these derivatives namely as antiviral drugs, more particularly as drugs useful for the treatment of subjects suffering from HCV, BVDV or Coxsackie virus infection.

The invention also thus to a method for preparing a compound of formula (Z), more particularly of the formula (A), (I), (II), (III), (IV), (V) and (VI) as described herein. Such a methods may essentially comprise the steps of:

a) reacting a (substituted) 3,4-diaminopyridine (A) is reacted with B (Y—R1) to give imidazo[4,5-c]pyridines (C);

b) introducing further substituents ($R^2$, $R^4$ and/or $R^5 \ne H$) either a) by cylization of an appropriately substituted 3,4-diaminopyridine (A) or b)) by introduction of the substituent(s) onto the imidazo[4,5-c]pyridine (C);

c) reacting the imidazo[4,5-c]pyridines (C) with an alkylating agent (D) ($R^3$—X—$R^6$) in an appropriate solvent under addition of a base at ambient temperature;

optionally, in the case of hydroxy, mercapto or amino substituents in position 4 or 6 of the imidazopyridine I (Z=O, S or NR);

d) introduction of a further substituent ($R^{25}$ or $R^{26}$) at position 1 or 3 of the imidazo[4,5-c]pyridine.

According to a particular embodiment, the present invention relates to compounds selected from the following group of compounds, the pharmaceutically acceptable salts, tautomers, and isomers thereof and their use in a treatment of viral infection or to manufacture a medicament to treat viral infections:

2-(2,6-Difluorophenyl)-5-[(2,6-difluorophenyl)methyl]-5H-imidazo[4,5-c]pyridine (GPJN-8);
5-Benzyl-2-(2,6-difluorophenyl)-5H-imidazo[4,5-c]pyridine (GPJN-1);
5-[(2,6-Difluorophenyl)methyl]-2-phenyl-5H-imidazo[4,5-c]pyridine (GPJN-3);
5-Benzyl-2-phenyl-5H-imidazo[4,5-c]pyridine (GPJN-4);
2-Phenyl-5-(3-phenylpropyl)-5H-imidazo[4,5-c]pyridine (GPJN-14);
5-[(2-Chlorophenyl)methyl]-2-phenyl-5H-imidazo[4,5-c]pyridine (GPJN-7);
5-[(3-Chlorophenyl)methyl]-2-phenyl-5H-imidazo[4,5-c]pyridine (GPJN-8);
5-[(4-Chlorophenyl)methyl]-2-phenyl-5H-imidazo[4,5-c]pyridine (GPJN-9);
5-[(2-Methoxyphenyl)methyl]-2-phenyl-5H-imidazo[4,5-c]pyridine (GPJN-11);
5-[(3-Methoxyphenyl)methyl]-2-phenyl-5H-imidazo[4,5-c]pyridine (GPJN-12);
5-[(4-Methoxyphenyl)methyl]-2-phenyl-5H-imidazo[4,5-c]pyridine (GPJN-13);
5-[(4-Methylphenyl)methyl]-2-phenyl-5H-imidazo[4,5-c]pyridine (GPJN-15);
5-[(2-Fluorophenyl)methyl]-2-phenyl-5H-imidazo[4,5-c]pyridine (GPJN-17);
5-[(3-Fluorophenyl)methyl]-2-phenyl-5H-imidazo[4,5-c]pyridine (GPJN-18);
5-[(4-Fluorophenyl)methyl]-2-phenyl-5H-imidazo[4,5-c]pyridine (GPJN-19);
5-[(2-Methylphenyl)methyl]-2-phenyl-5H-imidazo[4,5-c]pyridine (GPJN-20);
5-[(3-Methylphenyl)methyl]-2-phenyl-5H-imidazo[4,5-c]pyridine (GPJN-21);
5-[(4-Bromophenyl)methyl]-2-phenyl-5H-imidazo[4,54-c]pyridine (GPJN-22)
4-[(2-Phenyl-5H-imidazo[4,5-c]pyridin-5-yl)methyl)-benzonitrile (GPJN-23);
2-Phenyl-5-[[4-(trifluoromethyl)phenyl]methyl]-5H-imidazo[4,5-c]pyridine (GPJN-24);
5-[(4-Chlorophenyl)methyl]-2-phenyl-5H-imidazo[4,5-c]pyridine hydrochloride (GPJN-9×HCl);
5-[(5-Chloro-2-thienyl)methyl]-2-phenyl-5H-imidazo[4,5-c]pyridine (GPJN-25);
5-(2-Naphthalenylmethyl)-2-phenyl-5H-imidazo[4,5c-]pyridine (GPJN-26);
2-Phenyl-5-(4-phenylbutyl)-5H-imidazo[4,5-c]pyridine (GPJN-27);
5-([1,1'-Biphenyl]-4-ylmethyl)-2-phenyl-5H-imidazo[4,5-c]pyridine (GPJN-32);
2-Phenyl-5-(1-phenylethyl)-5H-imidazo[4,5-c]pyridine (GPJN-33);
5-(1-Naphthalenylmethyl)-2-phenyl-5H-imidazo[4,5-c]pyridine (GPJN-36);
2-(2,6-Difluorophenyl)-5-[(2,4-difluorophenyl)methyl]-5H-imidazo[4,5-c]pyridine (GPJN-40);
5-[(4-Bromophenyl)methyl]-2-(2-fluorophenyl)-5H-imidazo[4,5-c]pyridine (GPJN-52);
5-[(4-Bromophenyl)methyl]-2-(2-chlorophenyl)-5H-imidazo[4,5-c]pyridine (GPJN-54);
5-[(4-Bromophenyl)methyl]-2-(3-chlorophenyl)-5H-imidazo[4,5-c]pyridine (GPJN-55);
5-[(4-Bromophenyl)methyl]-2-(4-chlorophenyl)-5H-imidazo[4,5-c]pyridine (GPJN-56);
5-[(4-Bromophenyl)methyl]-2-(2-pyridinyl)-5H-imidazo[4,5-c]pyridine (GPJN-58);
5-[(4-Bromophenyl)methyl]-2-(2-thienyl)-5H-imidazo[4,5-c]pyridine (GPJN-53);
5-[(4-Bromophenyl)methyl]-2-(1-naphthalenyl)-5H-imidazo[4,5-c]pyridine (GPJN-62);
5-[(4-Bromophenyl)methyl]-2-(2-naphthalenyl)-5H-imidazo[4,5-c]pyridine (GPJN-63);
5-[(4-Iodophenyl)methyl]-2-phenyl-5H-imidazo[4,5-c]pyridine (GPJN-68);
5-[(4-Bromophenyl)methyl]-2-(3-fluorophenyl)-5H-imidazo[4,5-c]pyridine (GPJN-50);
5-[(4-Bromophenyl)methyl]-2-(3-methylphenyl)-5H-imidazo[4,5-c]pyridine (GPJN-60);
5-[(4-Bromophenyl)methyl]-2-(3-methoxyphenyl)-5H-imidazo[4,5-c]pyridine (GPJN-64);
5-[(4-Bromophenyl)methyl]-2-(3-bromophenyl)-5H-imidazo[4,5-c]pyridine (GPJN-65);
5-[(4-Chlorophenyl)methyl]-2-(3-bromophenyl)-5H-imidazo[4,5-c]pyridine (GPJN-80);
5-[(4-Chlorophenyl)methyl]-2-(3-chlorophenyl)-5H-imidazo[4,5-c]pyridine;
5-(2-Phenoxy-ethyl)-2-phenyl-5H-imidazo[4,5-c]pyridine (GPJN-73);
5-(3-Phenyl-prop-2-en-1-yl)-2-phenyl-5H-imidazo[4,5-c]pyridine (GPJN-75);
2-(3-Bromophenyl)-5-[(4-iodophenyl)methyl]-5H-imidazo[4,5-c]pyridine (GPJN-79);
5-[(4-Bromophenyl)methyl]-2-[(phenylthio)methyl]-5H-imidazo[4,5-c]pyridine (GPJN-83);
5-[(4-Bromophenyl)methyl]-2-[3-(trifluoromethyl)phenyl]-5H-imidazo[4,5-c]pyridine (GPJN-87);
5-([1,1'-Biphenyl]-4-ylmethyl)-2-(2-fluorophenyl)-5H-imidazo[4,5-c]pyridine (GPJN-110);
5-[(4-Chlorophenyl)methyl]-2-(2-fluorophenyl)-5H-imidazo[4,5-c]pyridine (GPJN-112);
2-(2-Fluorophenyl)-5-[(4-iodophenyl)methyl]-5H-imidazo[4,5-c]pyridine (GPJN-113);
5-[[4-(1,1-Dimethylethyl)phenyl]methyl]-2-(2-fluorophenyl)-5H-imidazo[4,5-c]pyridine (GPJN-114);

Optionally, the present invention relates to compounds selected from the following group of compounds, the pharmaceutically acceptable salts, tautomers, and isomers thereof and their use in a treatment of viral infection, more particularly for the treatment of HCV infection, or to manufacture a medicament to treat viral infections, more particularly HCV infections:

5-[(4-Bromophenyl)methyl]-2-(2-fluorophenyl)-5H-imidazo[4,5-c]pyridine (GPJN-52);
5-[(4-Bromophenyl)methyl]-2-(2-pyridinyl)-5H-imidazo[4,5-c]pyridine (GPJN-58);
5-[(4-Bromophenyl)methyl]-2-[(phenylthio)methyl]-5H-imidazo[4,5-c]pyridine (GPJN-83);
5-[(4-Bromophenyl)methyl]-2-[3-(trifluoromethyl)phenyl]-5H-imidazo[4,5-c]pyridine (GPJN-87);
5-([1,1'-Biphenyl]-4-ylmethyl)-2-(2-fluorophenyl)-5H-imidazo[4,5-c]pyridine (GPJN-110);
5-[(4-Chlorophenyl)methyl]-2-(2-fluorophenyl)-5H-imidazo[4,5-c]pyridine (GPJN-112);

2-(2-Fluorophenyl)-5-[(4-iodophenyl)methyl]-5H-imidazo[4,5-c]pyridine (GPJN-113);

5-[[4-(1,1-Dimethylethyl)phenyl]methyl]-2-(2-fluorophenyl)-5H-imidazo[4,5-c]pyridine (GPJN-114).

The invention further relates to methods of screening anti-viral compounds which comprises a) providing a compounds of the formula (Z), or optionally of the formula (A), (I), (II), (III), (IV), (V) or (VI) and b) determining the anti-viral activity of said compound.

Exemplary Enumerated Compounds.

By way of example and not limitation, embodiments of the invention are named below in tabular format (Table 7). Each embodiment of Table 7 is depicted as a substituted nucleus (Sc) in which the nucleus is designated by a number and each substituent is designated in order by further numbers. Table 1 is a schedule of nuclei used in forming the embodiments of Table 7. Each nucleus (Sc) is given a number designation from Table 1, and this designation appears first in each embodiment name. Similarly, Tables 2, 3, 4, 5 and 6 list the selected substituents, again by number designation.

Accordingly, each named embodiment of Table 7 is depicted by a number designating the nucleus from Table 1. If the nucleus is of formula 1 (from Table 1), then the letter and number substituents are in the order $R^1$ (Table 2), $R^3$ (Table 3), $R^4$ (Table 4), and X (Table 6). If the nucleus is of formula 2 (from Table 1), then the letter and number substituents are in the order $R^1$ (Table 2), $R^3$ (Table 3), $R^4$ (Table 4), $R^{26}$ (Table 5), and X (Table 6). The same embodiments of the invention exist for the nucleus of formula 2 (Table 1) wherein the N at position 1 is substituted by $R^{25}$ (corresponding to the embodiments of $R^{26}$ of Table 5) and the single or double bonds in the imidazo pyridine ring are adjusted accordingly.

Each group is shown having one or more tildas ("~"). The tildas are the points of covalent attachment of the group.

TABLE 1

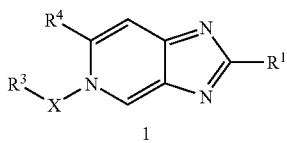

1

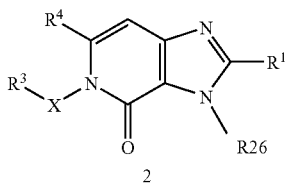

2

TABLE 2

$R^1$ Substituents

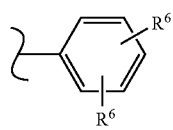

1

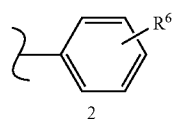

2

TABLE 2-continued $R^1$ Substituents

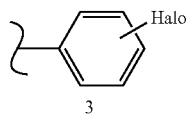

3

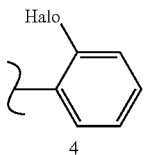

4

⊱ 5-membered benzoannellated ring having 1-2 nitrogen atoms and 1-2 $R^6$ groups

5

⊱ 6-membered benzoannellated ring having 1-2 nitrogen atoms and 1-2 $R^6$ groups

6

⊱ napthyl having 1-2 $R^6$ groups

7

TABLE 3

$R^3$ Substituents

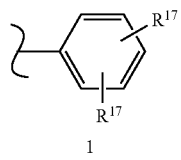

1

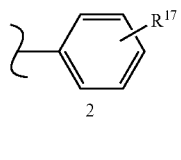

2

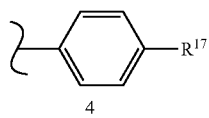

3

4

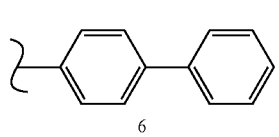

5

6

TABLE 4

$R^4$ Substituents

1

2

TABLE 5
R²⁶ Substituents
|  —H | 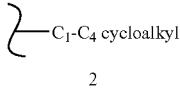 —C₁-C₄ cycloalkyl |
|---|---|
| 1 | 2 |
TABLE 6
X Substituents
| 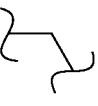 | 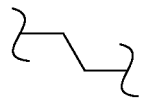 |
|---|---|
| 1 | 1 |
TABLE 6-continued
X Substituents
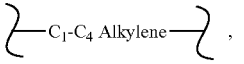 —C₁-C₄ Alkylene— ,
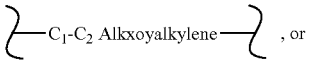 —C₁-C₂ Alkxoyalkylene— , or
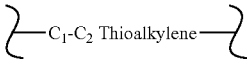 —C₁-C₂ Thioalkylene—
3
TABLE 7
Selected Embodiments of the Invention
Embodiments of Formula 1
1.1.1.1.1; 1.1.1.1.2; 1.1.1.1.3; 1.1.1.2.1; 1.1.1.2.2; 1.1.1.2.3; 1.1.2.1.1; 1.1.2.1.2; 1.1.2.1.3; 1.1.2.2.1; 1.1.2.2.2; 1.1.2.2.3; 1.1.3.1.1; 1.1.3.1.2; 1.1.3.1.3; 1.1.3.2.1; 1.1.3.2.2; 1.1.3.2.3; 1.1.4.1.1; 1.1.4.1.2; 1.1.4.1.3; 1.1.4.2.1; 1.1.4.2.2; 1.1.4.2.3; 1.1.5.1.1; 1.1.5.1.2; 1.1.5.1.3; 1.1.5.2.1; 1.1.5.2.2; 1.1.5.2.3; 1.1.6.1.1; 1.1.6.1.2; 1.1.6.1.3; 1.1.6.2.1; 1.1.6.2.2; 1.1.6.2.3; 1.2.1.1.1; 1.2.1.1.2; 1.2.1.1.3; 1.2.1.2.1; 1.2.1.2.2; 1.2.1.2.3; 1.2.2.1.1; 1.2.2.1.2; 1.2.2.1.3; 1.2.2.2.1; 1.2.2.2.2; 1.2.2.2.3; 1.2.3.1.1; 1.2.3.1.2; 1.2.3.1.3; 1.2.3.2.1; 1.2.3.2.2; 1.2.3.2.3; 1.2.4.1.1; 1.2.4.1.2; 1.2.4.1.3; 1.2.4.2.1; 1.2.4.2.2; 1.2.4.2.3; 1.2.5.1.1; 1.2.5.1.2; 1.2.5.1.3; 1.2.5.2.1; 1.2.5.2.2; 1.2.5.2.3; 1.2.6.1.1; 1.2.6.1.2; 1.2.6.1.3; 1.2.6.2.1; 1.2.6.2.2; 1.2.6.2.3; 1.3.1.1.1; 1.3.1.1.2; 1.3.1.1.3; 1.3.1.2.1; 1.3.1.2.2; 1.3.1.2.3; 1.3.2.1.1; 1.3.2.1.2; 1.3.2.1.3; 1.3.2.2.1; 1.3.2.2.2; 1.3.2.2.3; 1.3.3.1.1; 1.3.3.1.2; 1.3.3.1.3; 1.3.3.2.1; 1.3.3.2.2; 1.3.3.2.3; 1.3.4.1.1; 1.3.4.1.2; 1.3.4.1.3; 1.3.4.2.1; 1.3.4.2.2; 1.3.4.2.3; 1.3.5.1.1; 1.3.5.1.2; 1.3.5.1.3; 1.3.5.2.1; 1.3.5.2.2; 1.3.5.2.3; 1.3.6.1.1; 1.3.6.1.2; 1.3.6.1.3; 1.3.6.2.1; 1.3.6.2.2; 1.3.6.2.3; 1.4.1.1.1; 1.4.1.1.2; 1.4.1.1.3; 1.4.1.2.1; 1.4.1.2.2; 1.4.1.2.3; 1.4.2.1.1; 1.4.2.1.2; 1.4.2.1.3; 1.4.2.2.1; 1.4.2.2.2; 1.4.2.2.3; 1.4.3.1.1; 1.4.3.1.2; 1.4.3.1.3; 1.4.3.2.1; 1.4.3.2.2; 1.4.3.2.3; 1.4.4.1.1; 1.4.4.1.2; 1.4.4.1.3; 1.4.4.2.1; 1.4.4.2.2; 1.4.4.2.3; 1.4.5.1.1; 1.4.5.1.2; 1.4.5.1.3; 1.4.5.2.1; 1.4.5.2.2; 1.4.5.2.3; 1.4.6.1.1; 1.4.6.1.2; 1.4.6.1.3; 1.4.6.2.1; 1.4.6.2.2; 1.4.6.2.3; 1.5.1.1.1; 1.5.1.1.2; 1.5.1.1.3; 1.5.1.2.1; 1.5.1.2.2; 1.5.1.2.3; 1.5.2.1.1; 1.5.2.1.2; 1.5.2.1.3; 1.5.2.2.1; 1.5.2.2.2; 1.5.2.2.3; 1.5.3.1.1; 1.5.3.1.2; 1.5.3.1.3; 1.5.3.2.1; 1.5.3.2.2; 1.5.3.2.3; 1.5.4.1.1; 1.5.4.1.2; 1.5.4.1.3; 1.5.4.2.1; 1.5.4.2.2; 1.5.4.2.3; 1.5.5.1.1; 1.5.5.1.2; 1.5.5.1.3; 1.5.5.2.1; 1.5.5.2.2; 1.5.5.2.3; 1.5.6.1.1; 1.5.6.1.2; 1.5.6.1.3; 1.5.6.2.1; 1.5.6.2.2; 1.5.6.2.3; 1.6.1.1.1; 1.6.1.1.2; 1.6.1.1.3; 1.6.1.2.1; 1.6.1.2.2; 1.6.1.2.3; 1.6.2.1.1; 1.6.2.1.2; 1.6.2.1.3; 1.6.2.2.1; 1.6.2.2.2; 1.6.2.2.3; 1.6.3.1.1; 1.6.3.1.2; 1.6.3.1.3; 1.6.3.2.1; 1.6.3.2.2; 1.6.3.2.3; 1.6.4.1.1; 1.6.4.1.2; 1.6.4.1.3; 1.6.4.2.1; 1.6.4.2.2; 1.6.4.2.3; 1.6.5.1.1; 1.6.5.1.2; 1.6.5.1.3; 1.6.5.2.1; 1.6.5.2.2; 1.6.5.2.3; 1.6.6.1.1; 1.6.6.1.2; 1.6.6.1.3; 1.6.6.2.1; 1.6.6.2.2; 1.6.6.2.3; 1.7.1.1.1; 1.7.1.1.2; 1.7.1.1.3; 1.7.1.2.1; 1.7.1.2.2; 1.7.1.2.3; 1.7.2.1.1; 1.7.2.1.2; 1.7.2.1.3; 1.7.2.2.1; 1.7.2.2.2; 1.7.2.2.3; 1.7.3.1.1; 1.7.3.1.2; 1.7.3.1.3; 1.7.3.2.1; 1.7.3.2.2; 1.7.3.2.3; 1.7.4.1.1; 1.7.4.1.2; 1.7.4.1.3; 1.7.4.2.1; 1.7.4.2.2; 1.7.4.2.3; 1.7.5.1.1; 1.7.5.1.2; 1.7.5.1.3; 1.7.5.2.1; 1.7.5.2.2; 1.7.5.2.3; 1.7.6.1.1; 1.7.6.1.2; 1.7.6.1.3; 1.7.6.2.1; 1.7.6.2.2; 1.7.6.2.3.
Embodiments of Formula 2
2.1.1.1.1.1; 2.1.1.1.1.2; 2.1.1.1.1.3; 2.1.1.1.2.1; 2.1.1.1.2.2; 2.1.1.1.2.3; 2.1.1.2.1.1; 2.1.1.2.1.2; 2.1.1.2.1.3; 2.1.1.2.2.1; 2.1.1.2.2.2; 2.1.1.2.2.3; 2.1.2.1.1.1; 2.1.2.1.1.2; 2.1.2.1.1.3; 2.1.2.1.2.1; 2.1.2.1.2.2; 2.1.2.1.2.3; 2.1.2.2.1.1; 2.1.2.2.1.2; 2.1.2.2.1.3; 2.1.2.2.2.1; 2.1.2.2.2.2; 2.1.2.2.2.3; 2.1.3.1.1.1; 2.1.3.1.1.2; 2.1.3.1.1.3; 2.1.3.1.2.1; 2.1.3.1.2.2; 2.1.3.1.2.3; 2.1.3.2.1.1; 2.1.3.2.1.2; 2.1.3.2.1.3; 2.1.3.2.2.1; 2.1.3.2.2.2; 2.1.3.2.2.3; 2.1.4.1.1.2; 2.1.4.1.1.3; 2.1.4.1.2.1; 2.1.4.1.2.2; 2.1.4.1.2.3; 2.1.4.2.1.1; 2.1.4.2.1.2; 2.1.4.2.1.3; 2.1.4.2.2.1; 2.1.4.2.2.2; 2.1.4.2.2.3; 2.1.5.1.1.1; 2.1.5.1.1.2; 2.1.5.1.1.3; 2.1.5.1.2.1; 2.1.5.1.2.2; 2.1.5.1.2.3; 2.1.5.2.1.1; 2.1.5.2.1.2; 2.1.5.2.1.3; 2.1.5.2.2.1; 2.1.5.2.2.2; 2.1.5.2.2.3; 2.1.6.1.1.1; 2.1.6.1.1.2; 2.1.6.1.1.3; 2.1.6.1.2.1; 2.1.6.1.2.2; 2.1.6.1.2.3; 2.1.6.2.1.1; 2.1.6.2.1.2; 2.1.6.2.1.3; 2.1.6.2.2.1; 2.1.6.2.2.2; 2.1.6.2.2.3; 2.2.1.1.1.1; 2.2.1.1.1.2; 2.2.1.1.1.3; 2.2.1.1.2.1; 2.2.1.1.2.2; 2.2.1.1.2.3; 2.2.1.2.1.1; 2.2.1.2.1.2; 2.2.1.2.1.3; 2.2.1.2.2.1; 2.2.1.2.2.2; 2.2.1.2.2.3; 2.2.2.1.1.1; 2.2.2.1.1.2; 2.2.2.1.1.3; 2.2.2.1.2.1; 2.2.2.1.2.2; 2.2.2.1.2.3; 2.2.2.2.1.1; 2.2.2.2.1.2; 2.2.2.2.1.3; 2.2.2.2.2.1; 2.2.2.2.2.2; 2.2.2.2.2.3; 2.2.3.1.1.1; 2.2.3.1.1.2; 2.2.3.1.1.3; 2.2.3.1.2.1; 2.2.3.1.2.2; 2.2.3.1.2.3; 2.2.3.2.1.1; 2.2.3.2.1.2; 2.2.3.2.1.3; 2.2.3.2.2.1; 2.2.3.2.2.2; 2.2.3.2.2.3; 2.2.4.1.1.1; 2.2.4.1.1.2; 2.2.4.1.1.3; 2.2.4.1.2.1; 2.2.4.1.2.2; 2.2.4.1.2.3; 2.2.4.2.1.1; 2.2.4.2.1.2; 2.2.4.2.1.3; 2.2.4.2.2.1; 2.2.4.2.2.2; 2.2.4.2.2.3; 2.2.5.1.1.1; 2.2.5.1.1.2; 2.2.5.1.1.3; 2.2.5.1.2.1; 2.2.5.1.2.2; 2.2.5.1.2.3; 2.2.5.2.1.1; 2.2.5.2.1.2; 2.2.5.2.1.3; 2.2.5.2.2.1; 2.2.5.2.2.2; 2.2.5.2.2.3; 2.2.6.1.1.1; 2.2.6.1.1.2; 2.2.6.1.1.3; 2.2.6.1.2.1; 2.2.6.1.2.2; 2.2.6.1.2.3; 2.2.6.2.1.1; 2.2.6.2.1.2;

TABLE 7-continued

Selected Embodiments of the Invention 2.2.6.2.1.3; 2.2.6.2.2.1; 2.2.6.2.2.2; 2.2.6.2.2.3; 2.3.1.1.1.1; 2.3.1.1.1.2; 2.3.1.1.1.3;
2.3.1.1.2.1; 2.3.1.1.2.2; 2.3.1.1.2.3; 2.3.1.2.1.1; 2.3.1.2.1.2; 2.3.1.2.1.3; 2.3.1.2.2.1;
2.3.1.2.2.2; 2.3.1.2.2.3; 2.3.2.1.1.1; 2.3.2.1.1.2; 2.3.2.1.1.3; 2.3.2.1.2.1; 2.3.2.1.2.2;
2.3.2.1.2.3; 2.3.2.2.1.1; 2.3.2.2.1.2; 2.3.2.2.1.3; 2.3.2.2.2.1; 2.3.2.2.2.2; 2.3.2.2.2.3;
2.3.3.1.1.1; 2.3.3.1.1.2; 2.3.3.1.1.3; 2.3.3.1.2.1; 2.3.3.1.2.2; 2.3.3.1.2.3; 2.3.3.2.1.1;
2.3.3.2.1.2; 2.3.3.2.1.3; 2.3.3.2.2.1; 2.3.3.2.2.2; 2.3.3.2.2.3; 2.3.4.1.1.1; 2.3.4.1.1.2;
2.3.4.1.1.3; 2.3.4.1.2.1; 2.3.4.1.2.2; 2.3.4.1.2.3; 2.3.4.2.1.1; 2.3.4.2.1.2; 2.3.4.2.1.3;
2.3.4.2.2.1; 2.3.4.2.2.2; 2.3.4.2.2.3; 2.3.5.1.1.1; 2.3.5.1.1.2; 2.3.5.1.1.3; 2.3.5.1.2.1;
2.3.5.1.2.2; 2.3.5.1.2.3; 2.3.5.2.1.1; 2.3.5.2.1.2; 2.3.5.2.1.3; 2.3.5.2.2.1; 2.3.5.2.2.2;
2.3.5.2.2.3; 2.3.6.1.1.1; 2.3.6.1.1.2; 2.3.6.1.1.3; 2.3.6.1.2.1; 2.3.6.1.2.2; 2.3.6.1.2.3;
2.3.6.2.1.1; 2.3.6.2.1.2; 2.3.6.2.1.3; 2.3.6.2.2.1; 2.3.6.2.2.2; 2.3.6.2.2.3; 2.4.1.1.1.1;
2.4.1.1.1.2; 2.4.1.1.1.3; 2.4.1.1.2.1; 2.4.1.1.2.2; 2.4.1.1.2.3; 2.4.1.2.1.1; 2.4.1.2.1.2;
2.4.1.2.1.3; 2.4.1.2.2.1; 2.4.1.2.2.2; 2.4.1.2.2.3; 2.4.2.1.1.1; 2.4.2.1.1.2; 2.4.2.1.1.3;
2.4.2.1.2.1; 2.4.2.1.2.2; 2.4.2.1.2.3; 2.4.2.2.1.1; 2.4.2.2.1.2; 2.4.2.2.1.3; 2.4.2.2.2.1;
2.4.2.2.2.2; 2.4.2.2.2.3; 2.4.3.1.1.1; 2.4.3.1.1.2; 2.4.3.1.1.3; 2.4.3.1.2.1; 2.4.3.1.2.2;
2.4.3.1.2.3; 2.4.3.2.1.1; 2.4.3.2.1.2; 2.4.3.2.1.3; 2.4.3.2.2.1; 2.4.3.2.2.2; 2.4.3.2.2.3;
2.4.4.1.1.1; 2.4.4.1.1.2; 2.4.4.1.1.3; 2.4.4.1.2.1; 2.4.4.1.2.2; 2.4.4.1.2.3; 2.4.4.2.1.1;
2.4.4.2.1.2; 2.4.4.2.1.3; 2.4.4.2.2.1; 2.4.4.2.2.2; 2.4.4.2.2.3; 2.4.5.1.1.1; 2.4.5.1.1.2;
2.4.5.1.1.3; 2.4.5.1.2.1; 2.4.5.1.2.2; 2.4.5.1.2.3; 2.4.5.2.1.1; 2.4.5.2.1.2; 2.4.5.2.1.3;
2.4.5.2.2.1; 2.4.5.2.2.2; 2.4.5.2.2.3; 2.4.6.1.1.1; 2.4.6.1.1.2; 2.4.6.1.1.3; 2.4.6.1.2.1;
2.4.6.1.2.2; 2.4.6.1.2.3; 2.4.6.2.1.1; 2.4.6.2.1.2; 2.4.6.2.1.3; 2.4.6.2.2.1; 2.4.6.2.2.2;
2.4.6.2.2.3; 2.5.1.1.1.1; 2.5.1.1.1.2; 2.5.1.1.1.3; 2.5.1.1.2.1; 2.5.1.1.2.2; 2.5.1.1.2.3;
2.5.1.2.1.1; 2.5.1.2.1.2; 2.5.1.2.1.3; 2.5.1.2.2.1; 2.5.1.2.2.2; 2.5.1.2.2.3; 2.5.2.1.1.1;
2.5.2.1.1.2; 2.5.2.1.1.3; 2.5.2.1.2.1; 2.5.2.1.2.2; 2.5.2.1.2.3; 2.5.2.2.1.1; 2.5.2.2.1.2;
2.5.2.2.1.3; 2.5.2.2.2.1; 2.5.2.2.2.2; 2.5.2.2.2.3; 2.5.3.1.1.1; 2.5.3.1.1.2; 2.5.3.1.1.3;
2.5.3.1.2.1; 2.5.3.1.2.2; 2.5.3.1.2.3; 2.5.3.2.1.1; 2.5.3.2.1.2; 2.5.3.2.1.3; 2.5.3.2.2.1;
2.5.3.2.2.2; 2.5.3.2.2.3; 2.5.4.1.1.1; 2.5.4.1.1.2; 2.5.4.1.1.3; 2.5.4.1.2.1; 2.5.4.1.2.2;
2.5.4.1.2.3; 2.5.4.2.1.1; 2.5.4.2.1.2; 2.5.4.2.1.3; 2.5.4.2.2.1; 2.5.4.2.2.2; 2.5.4.2.2.3;
2.5.5.1.1.1; 2.5.5.1.1.2; 2.5.5.1.1.3; 2.5.5.1.2.1; 2.5.5.1.2.2; 2.5.5.1.2.3; 2.5.5.2.1.1;
2.5.5.2.1.2; 2.5.5.2.1.3; 2.5.5.2.2.1; 2.5.5.2.2.2; 2.5.5.2.2.3; 2.5.6.1.1.1; 2.5.6.1.1.2;
2.5.6.1.1.3; 2.5.6.1.2.1; 2.5.6.1.2.2; 2.5.6.1.2.3; 2.5.6.2.1.1; 2.5.6.2.1.2; 2.5.6.2.1.3;
2.5.6.2.2.1; 2.5.6.2.2.2; 2.5.6.2.2.3; 2.6.1.1.1.1; 2.6.1.1.1.2; 2.6.1.1.1.3; 2.6.1.1.2.1;
2.6.1.1.2.2; 2.6.1.1.2.3; 2.6.1.2.1.1; 2.6.1.2.1.2; 2.6.1.2.1.3; 2.6.1.2.2.1; 2.6.1.2.2.2;
2.6.1.2.2.3; 2.6.2.1.1.1; 2.6.2.1.1.2; 2.6.2.1.1.3; 2.6.2.1.2.1; 2.6.2.1.2.2; 2.6.2.1.2.3;
2.6.2.2.1.1; 2.6.2.2.1.2; 2.6.2.2.1.3; 2.6.2.2.2.1; 2.6.2.2.2.2; 2.6.2.2.2.3; 2.6.3.1.1.1;
2.6.3.1.1.2; 2.6.3.1.1.3; 2.6.3.1.2.1; 2.6.3.1.2.2; 2.6.3.1.2.3; 2.6.3.2.1.1; 2.6.3.2.1.2;
2.6.3.2.1.3; 2.6.3.2.2.1; 2.6.3.2.2.2; 2.6.3.2.2.3; 2.6.4.1.1.1; 2.6.4.1.1.2; 2.6.4.1.1.3;
2.6.4.1.2.1; 2.6.4.1.2.2; 2.6.4.1.2.3; 2.6.4.2.1.1; 2.6.4.2.1.2; 2.6.4.2.1.3; 2.6.4.2.2.1;
2.6.4.2.2.2; 2.6.4.2.2.3; 2.6.5.1.1.1; 2.6.5.1.1.2; 2.6.5.1.1.3; 2.6.5.1.2.1; 2.6.5.1.2.2;
2.6.5.1.2.3; 2.6.5.2.1.1; 2.6.5.2.1.2; 2.6.5.2.1.3; 2.6.5.2.2.1; 2.6.5.2.2.2; 2.6.5.2.2.3;
2.6.6.1.1.1; 2.6.6.1.1.2; 2.6.6.1.1.3; 2.6.6.1.2.1; 2.6.6.1.2.2; 2.6.6.1.2.3; 2.6.6.2.1.1;
2.6.6.2.1.2; 2.6.6.2.1.3; 2.6.6.2.2.1; 2.6.6.2.2.2; 2.6.6.2.2.3; 2.7.1.1.1.1; 2.7.1.1.1.2;
2.7.1.1.1.3; 2.7.1.1.2.1; 2.7.1.1.2.2; 2.7.1.1.2.3; 2.7.1.2.1.1; 2.7.1.2.1.2; 2.7.1.2.1.3;
2.7.1.2.2.1; 2.7.1.2.2.2; 2.7.1.2.2.3; 2.7.2.1.1.1; 2.7.2.1.1.2; 2.7.2.1.1.3; 2.7.2.1.2.1;
2.7.2.1.2.2; 2.7.2.1.2.3; 2.7.2.2.1.1; 2.7.2.2.1.2; 2.7.2.2.1.3; 2.7.2.2.2.1; 2.7.2.2.2.2;
2.7.2.2.2.3; 2.7.3.1.1.1; 2.7.3.1.1.2; 2.7.3.1.1.3; 2.7.3.1.2.1; 2.7.3.1.2.2; 2.7.3.1.2.3;
2.7.3.2.1.1; 2.7.3.2.1.2; 2.7.3.2.1.3; 2.7.3.2.2.1; 2.7.3.2.2.2; 2.7.3.2.2.3; 2.7.4.1.1.1;
2.7.4.1.1.2; 2.7.4.1.1.3; 2.7.4.1.2.1; 2.7.4.1.2.2; 2.7.4.1.2.3; 2.7.4.2.1.1; 2.7.4.2.1.2;
2.7.4.2.1.3; 2.7.4.2.2.1; 2.7.4.2.2.2; 2.7.4.2.2.3; 2.7.5.1.1.1; 2.7.5.1.1.2; 2.7.5.1.1.3;
2.7.5.1.2.1; 2.7.5.1.2.2; 2.7.5.1.2.3; 2.7.5.2.1.1; 2.7.5.2.1.2; 2.7.5.2.1.3; 2.7.5.2.2.1;
2.7.5.2.2.2; 2.7.5.2.2.3; 2.7.6.1.1.1; 2.7.6.1.1.2; 2.7.6.1.1.3; 2.7.6.1.2.1; 2.7.6.1.2.2;
2.7.6.1.2.3; 2.7.6.2.1.1; 2.7.6.2.1.2; 2.7.6.2.1.3; 2.7.6.2.2.1; 2.7.6.2.2.2; 2.7.6.2.2.3.

DETAILED DESCRIPTION

In each of the following definitions, the number of carbon atoms represents the maximum number of carbon atoms generally optimally present in the substituent or linker; it is understood that where otherwise indicated in the present application, the number of carbon IS atoms represents the optimal maximum number of carbon atoms for that particular substituent or linker.

The term "$C_{1-18}$ alkyl" as used herein C1-C18 normal, secondary, or tertiary hydrocarbon. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl. The term also includes $C_{1-18}$ halo-alkyls, which is a $C_{1-18}$ alkyl bearing at least one halogen.

As used herein and unless otherwise stated, the term "$C_{3-10}$ cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein and unless otherwise stated, the term "$C_{3-10}$ cycloalkylene" refers to a cyclic hydrocarbon radical of 3-10 carbon atoms, and having two monovalent radical centers derived by the removal of two hydrogen atoms from the same or two different carbon atoms of a parent alkane; i.e. the divalent hydrocarbon radical corresponding to the above defined $C_{3-10}$ cycloalkyl.

The terms "$C_{2-18}$ alkenyl" and "$C_{3-10}$ cycloalkenyl" as used herein is C2-C18 normal, secondary or tertiary and respectively C3-10 cyclic hydrocarbon with at least one site (usually 1 to 3, preferably 1) of unsaturation, i.e. a carbon-carbon, sp2 double bond. Examples include, but are not limited to: ethylene or vinyl (—CH=CH2), allyl (—CH2CH=CH2), cyclopentenyl (—C5H7), and 5-hexenyl (—CH2CH2CH2CH=CH2). The double bond may be in the cis or trans configuration.

The terms "$C_{2-18}$ alkynyl" and "$C_{3-10}$ cycloalkynyl" as used herein refer respectively C2-C18 normal, secondary, tertiary or the C3-10 cyclic hydrocarbon with at least one site (usually 1 to 3, preferably 1) of unsaturation, i.e. a carbon-carbon, sp triple bond. Examples include, but are not limited to: acetylenic (—C°CH) and propargyl (—CH2C°CH).

The terms "$C_{1-18}$ alkylene" as used herein each refer to a saturated, branched or straight chain hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH2-) 1,2-ethyl (—CH2CH2-), 1,3-propyl (—CH2CH2CH2-), 1,4-butyl (—CH2CH2CH2CH2-), and the like.

The terms "$C_{2-18}$ alkenylene" and "$C_{3-10}$ cycloalkenylene as used herein refer to an unsaturated branched chain, straight chain, and respectively a cyclic hydrocarbon radical of 2-18 respectively 3-10 carbon atoms, and having two monovalent radical centers derived by the removal of two hydrogen atoms from the same or two different carbon atoms of a parent alkene, i.e. double carbon-carbon bond moiety. Typical alkenylene radicals include, but are not limited to: 1,2-ethylene (—CH=CH—).

The terms "$C_{2-18}$ alkynylene" and "$C_{3-10}$ cycloalkenylene" as used herein refer respectively to an unsaturated, branched or straight chain of 2-18 carbon atoms or to a cyclic hydrocarbon radical of 3-10 carbon atoms respectively, having two monovalent radical centers derived by the removal of two hydrogen atoms from the same or two different carbon atoms of a parent alkane, i.e. triple carbon-carbon bond moiety. Typical alkynylene radicals include, but are not limited to: acetylene (—C°C—), propargyl (—CH2C°C—), and 4-pentynyl (—CH2CH2CH2C°CH—).

The term "aryl" as used herein means a aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, spiro, anthracene, biphenyl, and the like.

"Arylalkyl" as used herein refers to an alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

The term "heterocyclic ring" as used herein means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4a-carbazolyl, carbazolyl, β-carbolinyl, phenanthridinyl, acridinyl, pyrimidinyl, phenantbrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

Heteroaryl means pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazoline, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated, unsaturated or aromatic ring system having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. Carbocycle thus includes some aryl groups.

As used herein and unless otherwise stated, the terms "$C_{1-18}$ alkoxy", "$C_{3-10}$ cycloalkoxy", "aryloxy", "arylalkyloxy", "oxyheterocyclic ring", "thio $C_{1-7}$ alkyl", thio $C_{3-10}$ cycloalkyl", "arylthio", "arylalkylthio" and "thioheterocyclic ring" refer to substituents wherein a $C_{1-18}$ alkyl radical, respectively a $C_{3-10}$ cycloalkyl, aryl, arylalkyl or heterocyclic ring radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like.

As used herein and unless otherwise stated, the term halogen means any atom selected from the group consisting of fluorine, chlorine, bromine and iodine.

Any substituent designation that is found in more than one site in a compound of this invention shall be independently selected.

As used herein and unless otherwise stated, the term "amino-acid" refers to a radical derived from a molecule having the chemical formula $H_2N$—$CHR^{28}$—COOH, wherein $R^{28}$ is the side group of atoms characterizing the amino-acid type; said molecule may be one of the 20 naturally-occurring amino-acids or any non naturally-occurring amino-acid. Esters of amino acids included within this definition are substituted at one or more carboxyl groups with $C_{1-6}$ alkyl. This is the case even when the amino acid is bonded through carboxyl because some amino acids contain more than one carboxyl groups, and in this case the unbonded carboxyl optionally is esterified.

$R^{28}$ is $C_1$-$C_6$ alkyl or C1-C6 alkyl substituted with amino, carboxyl, amide, carboxyl (as well as esters, as noted above), hydroxyl, $C_6$-$C_7$ aryl, guanidinyl, imidazolyl, indolyl, sulfhydryl, sulfoxide, and/or alkylphosphate. $R^{28}$ also is taken together with the amino acid αnitrogen to form a proline residue ($R^{27}$ is —$(CH_2)_3$—). However, $R^{28}$ is generally the side group of a naturally-occurring amino acid such as H, —$CH_3$, —$CH(CH_3)_2$, —$CH_2$—$CH(CH_3)_2$, —$CHCHH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—C($NH_2$)—$NH_2$. $R^{28}$ also includes 1-guanidinoprop-3-yl, benzyl, 4-hydroxybenzyl, imidazol-4-yl, indol-3-yl, methoxyphenyl and ethoxyphenyl.

Optionally the amino acid residue is a hydrophobic residue such as mono-or di-alkyl or aryl amino acids, cycloalkylamino acids and the like. Optionally, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included.

Generally, only one of any site in the parental molecule is substituted with an amino acid, although it is within the scope of this invention to introduce amino acids at more than one permitted site. In general, the α-amino or α-carboxyl group of the amino acid are bonded to the remainder of the molecule, i.e., carboxyl or amino groups in the amino acid side chains generally are not used to form the amide bonds with the parental compound (although these groups may need to be protected during synthesis of the conjugates).

The amino acid esters optionally are hydrolyzable in vivo or in vitro under acidic (pH<3) or basic (pH>10) conditions. Optionally, they are substantially stable in the gastrointestinal tract of humans but are hydrolyzed enzymatically in blood or in intracellular environments.

Substituents optionally are designated with or without bonds. Regardless of bond indications, if a substituent is polyvalent (based on its position in the structure referred to), then any and all possible orientations of the substituent are intended.

Formula's (Z) and (A) depict optional single or double bonds. It will be understood that the bonds are present such that the aromatic nature of the nucleus of formula (Z) or (A) is preserved, i.e., these formulas are intended to embrace all possible tautomers. For example $R^{25}$ or $R^{26}$ will be absent if the ring N to which they are bonded as indicated in the formula is linked to a flanking ring carbon atom by a double bond. On the other hand, $R^{25}$ or $R^{26}$ may be present when the N atom to which it is bonded as indicated in the formula is linked to its flanking carbon atoms by single bonds only; in this case aromaticity is accomodated by other substituents, e.g. where $R^2$ or $R^4$ is oxo.

The compounds of the invention optionally are bound covalently to an insoluble matrix and used for affinity chromatography (separations, depending on the nature of the groups of the compounds, for example compounds with pendant aryl are useful in hydrophobic affinity separations.

The compounds of the invention are employed for the treatment or prophylaxis of viral infections, more particularly flaviviral or picornaviral infections, in particular, HCV and BVDV. When using one or more derivatives of the formula (Z) as defined herein:

the active ingredients of the compound(s) may be administered to the mammal (including a human) to be treated by any means well known in the art, i.e. orally, intranasally, subcutaneously, intramuscularly, intradermally, intravenously, intra-arterially, parenterally or by catheterization.

the therapeutically effective amount of the preparation of the compound(s), especially for the treatment of viral infections in humans and other mammals, preferably is a flaviviral or picornaviral enzyme inhibiting amount. More preferably, it is a flaviviral or picornaviral replication inhibiting amount or a flaviviral or picornaviral enzyme inhibiting amount of the derivative(s) of formula (Z) as defined herein corresponds to an amount which ensures a plasma level of between 1 μg/ml and 100 mg/ml, optionally of 10 mg/ml.

This can be achieved by administration of a dosage of in the range of 0.001 mg to 20 mg, preferably 0.01 mg to 5 mg, preferably 0.1 mg to 1 mg per day per kg bodyweight for humans. Depending upon the pathologic condition to be treated and the patient's condition, the said effective amount may be divided into several sub-units per day or may be administered at more than one day intervals.

The present invention further relates to a method for preventing or treating a viral infections in a subject or patient by administering to the patient in need thereof a therapeutically effective amount imidazo[4,5-c]pyridine derivatives of the present invention. The therapeutically effective amount of the preparation of the compound(s), especially for the treatment of viral infections in humans and other mammals, preferably is a flaviviral or picornaviral enzyme inhibiting amount. More preferably, it is a flaviviral or picornaviral replication inhibiting amount or a flaviviral or picornaviral enzyme inhibiting amount of the derivative(s) of formula (Z) as defined herein. Suitable dosage is usually in the range of 0.001 mg to 60 mg, optionally 0.01 mg to 10 mg, optionally 0.1 mg to 1 mg per day per kg bodyweight for humans. Depending upon the pathologic condition to be treated and the patient's condition, the said effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x + FIC_y$) is equal to 1.0, the combination is said to be additive; when it is between 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

This principle may be applied to a combination of different antiviral drugs of the invention or to a combination of the antiviral drugs of the invention with other drugs that exhibit anti-BVDV or anti-HCV activity.

The invention thus relates to a pharmaceutical composition or combined preparation having synergistic effects against a viral infection and containing:

Either:
A)
(a) a combination of two or more of the imidazo[4,5-c]pyridine derivatives of the present invention, and
(b) optionally one or more pharmaceutical excipients or pharmaceutically acceptable carriers, for simultaneous, separate or sequential use in the treatment or prevention of a viral infection or
B)
(c) one or more anti-viral agents, and
(d) at least one of the imidazo[4,5-c]pyridine derivatives of the present invention, and
(e) optionally one or more pharmaceutical excipients or pharmaceutically acceptable carriers, for simultaneous, separate or sequential use in the treatment or prevention of a viral infection.

Suitable anti-viral agents for inclusion into the synergistic antiviral compositions or combined preparations of this invention include, for instance, interferon-alfa (either pegylated or not), ribavirin and other selective inhibitors of the replication of BVDV or HCV.

The pharmaceutical composition or combined preparation with synergistic activity against viral infection according to this invention may contain the imidazo[4,5-c]pyridine derivatives of the present invention over a broad content range depending on the contemplated use and the expected effect of the preparation. Generally, the content of the imidazo[4,5-c] pyridine derivatives of the present invention of the combined preparation is within the range of 0.1 to 99.9% by weight, preferably from 1 to 99% by weight, more preferably from 5 to 95% by weight.

According to a particular embodiment of the invention, the compounds of the invention may be employed in combination with other therapeutic agents for the treatment or prophylaxis of flaviviral or picornaviral infections, optionally, HCV and BVDV. The invention therefore relates to the use of a composition comprising:

(a) one or more compounds of formula (Z), and
(b) one or more Flaviviral or Picornaviral enzyme inhibitors as biologically active agents in respective proportions such as to provide a synergistic effect against a viral infection, particularly a Flaviviral or Picornaviral infection in a mammal, for instance in the form of a combined preparation for simultaneous, separate or sequential use in viral infection therapy, such as of HCV, BVDV and Coxsackie virus. Examples of such further therapeutic agents for use in combinations include agents that are effective for the treatment or prophylaxis of these infections, including interferon alpha, ribavirin, a compound falling within the scope of disclosure EP1162196, WO 03/010141, WO 03/007945 and WO 03/010140, a compound falling within the scope of disclosure WO 00/204425, and other patents or patent applications within their patent families or all the foregoing filings and/or an inhibitor of flaviviral protease and/or one or more additional flavivirus polymerase inhibitors.

When using a combined preparation of (a) and (b):
the active ingredients (a) and (b) may be administered to the mammal (including a human) to be treated by any means well known in the art, i.e. orally, intranasally, subcutaneously, intramuscularly, intradermally, intravenously, intra-arterially, parenterally or by catheterization.

the therapeutically effective amount of the combined preparation of (a) and (b), especially for the treatment of viral infections in humans and other mammals, particularly is a flaviviral or picornaviral enzyme inhibiting amount. More particularly, it is a fiaviviral or picornaviral replication inhibiting amount of derivative (a) and a flaviviral or picornaviral enzyme inhibiting amount of inhibitor (b). Still more particularly when the said flaviviral or picornaviral enzyme inhibitor (b) is a polymerase inhibitor, its effective amount is a polymerase inhibiting amount When the said flaviviral or picornaviral enzyme inhibitor (b) is a protease inhibitor, its effective amount is a protease inhibiting amount ingredients (a) and (b) may be administered simultaneously but it is also beneficial to administer them separately or sequentially, for instance within a relatively short period of time (e.g. within about 24 hours) in order to achieve their functional fusion in the body to be treated.

The invention also relates to the compounds of formula (Z) being used for inhibition of the proliferation of other viruses than BVDV, HCV or Coxsackie virus, particularly for the inhibition of other flaviviruses or picornaviruses, with in particular yellow fever virus, Dengue virus, hepatitis B virus, hepatitis G virus, Classical Swine Fever virus or the Border Disease Virus, and also for the inhibition of HIV and other retroviruses or lentiviruses.

The present invention further provides veterinary compositions comprising at least one active ingredient as above defined together with a veterinary carrier therefore, for example in the treatment of BVDV. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

More generally, the invention relates to the compounds of formula (Z) being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formula (Z) are able to form. Therefore, the compounds of this invention optionally comprise salts of the compounds herein, especially pharmaceutically acceptable non-toxic salts containing for example, Na+, Li+, K+, Ca+2 and Mg+2. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing Li+, Na+, and K+. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formula (Z) as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and. NX4+ (wherein X is C1-C4 alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as Na+ and NX4+ (wherein X typically is independently selected from H or a C1-C4 alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and sterochemical forms, which the compounds of formula (Z) may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formula (Z) may have at least one chiral center) of the basic molecular structure, as well as the stereochemically pure or enriched compounds. More particularly, stereogenic centers may have either the R— or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure"

relates to compounds having a stereoisomeric excess of at least about 80% (i.e. at least 90% of one isomer and at most 10% of the other possible isomers), preferably at least 90%, more preferably at least 94% and most preferably at least 97%. The terms "enantionierically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as bromine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as methyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifuoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and ChiralpakTM AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of formula (1) may easily be determined by those skilled in the art while using well-known methods such as, for example, X-ray diffraction.

The compounds of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by incironisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalritoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw", 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner.

While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

The compounds of formula (Z), (A), (I), (II), (III), (IV), (V) and (VI) can be prepared while using a series of chemical reactions well known to those skilled in the art, altogether making up the process for preparing said compounds and exemplified further. The processes described further are only meant as examples and by no means are meant to limit the scope of the present invention.

General Methods and Materials for the Preparation of the Compounds of the Invention:

The compounds according to the invention are conveniently prepared in two steps; known to to the skilled person. First, a (substituted) 3,4-diaminopyridine (A) is reacted with B to give imidazo[4,5-c]pyridines C (scheme 1). If Y is COOH, then the cyclization is carried out under acidic catalysis (preferably in polyphosphoric acid at a temperature between 90 and 200° C.); other methods include reaction in 4N hydrochloric acid at reflux temperature or neat at a temperature between 90 and 180° C. (for aliphatic carboxylic acids). In the case of acid-sensitive groups like alkoxy or thiophene, the reaction can be carried out in phosphorus oxychloride at a temperature between 70 and 120° C. Alternatively, reaction with aldehydes (Y=CHO) or their bisulfite adducts under oxidative conditions (nitrobenzene, DDQ, copper(II)acetate, $O_2$, sulfur etc.) gives imidazo[4,5-c]pyridines C. Other methods are the reaction of (substituted) 3,4-diaminopyridines (A) with orthoesters (Y=C(OR)$_3$), anhydrides (Y=OCOOR) or acid halogenides (Y=COX), etc.

Scheme 1:

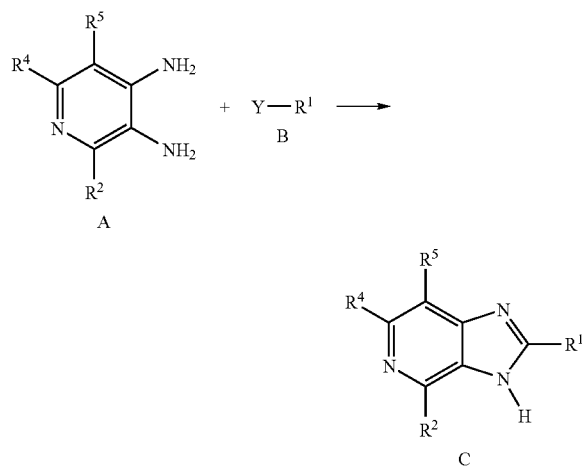

The imidazo[4,5-c]pyridines C can be formulated in three tautomeric forms (1H, 3H or 5H), as shown in scheme 2.

Scheme 2:

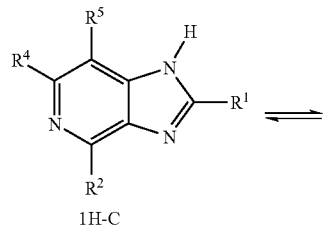

1H-C

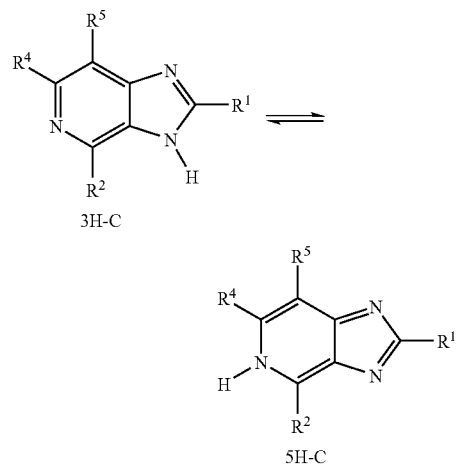

Substituents ($R^2$, $R^4$ and/or $R^5 \neq H$) can be introduced by two ways: i) either by cyclization of an appropriately substituted 3,4-diaminopyridine A or ii) by introduction of the substituent(s) onto the imidazo[4,5-c]pyridine C. For example, halogens can be introduced in position 7 of the imidazo[4,5-c]pyridine C by direct halogenation ($R^5$=Br: with bromine in acetic acid or with NBS in acetic acid; $R^5$=Cl: with chlorine in acetic acid or with NCS in acetic acid). Another example is the direct nitration ($R^5$=NO$_2$), followed by reduction to give the amino group ($R^5$=NH$_2$). Substituents in position 4 of the imidazo[4,5-c]pyridine C can be introduced, for example, via the corresponding imidazo[4,5-c]pyridine $N^5$-oxides.

Substituted 3,4-diaminopyridines can, for example, be prepared according to the following route (scheme 3): Nitration (HNO$_3$/H$_2$SO$_4$) of a 2- or 3-substituted pyridine N-oxide gives the corresponding 4-nitro product. Double reduction of the N-oxide and the nitro group with iron in acetic acid gives the 2- or 3-substituted 4-aminopyridine. Subsequent nitration (HNO$_3$/H$_2$SO$_4$) and reduction of the nitro group with iron in a mixture of concentrated hydrochloric acid and ethanol gives the desired substituted 3,4-diaminopyridines.

Scheme 3:

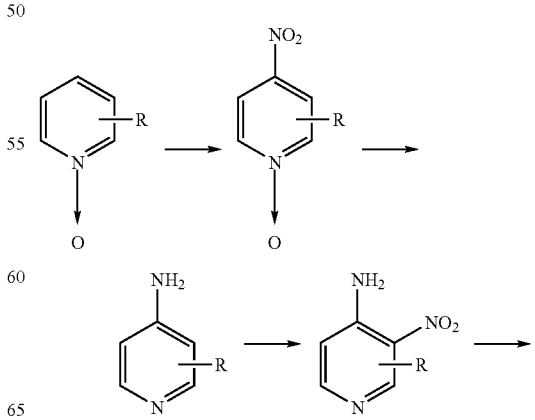

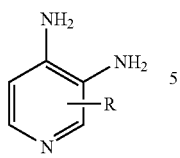

In the case of the 3-substituted pyridines as starting materials 5-substituted 3,4-diaminopyridines are obtained. Nitration of 2-substituted 4-aminopyridines gives mixtures of 3- and 5-nitropyridines, with 3-nitration as the predominant reaction.

4-Amino-2-methoxy-3-nitropyridine can be prepared by reaction of 4-amino-2-chloro-3-nitropyridine with sodium methoxide. 3-Substituted 4-aminopyridines can also be prepared by electrophilic substitution of 4-aminopyridines (e.g. chlorination, bromination etc.). 4-Amino-3-bromo-5-nitropyridine can be obtained by bromination of 4-amino-3-nitropyridine.

The second and final step is the reaction of the imidazo[4,5]pyridines C with an alkylating agent D ($R^6$=Cl, Br, etc.) in an appropriate solvent (preferably DMF) under addition of a base (preferably aqueous sodium hydroxide) at ambient temperature (scheme 4).

Scheme 4:

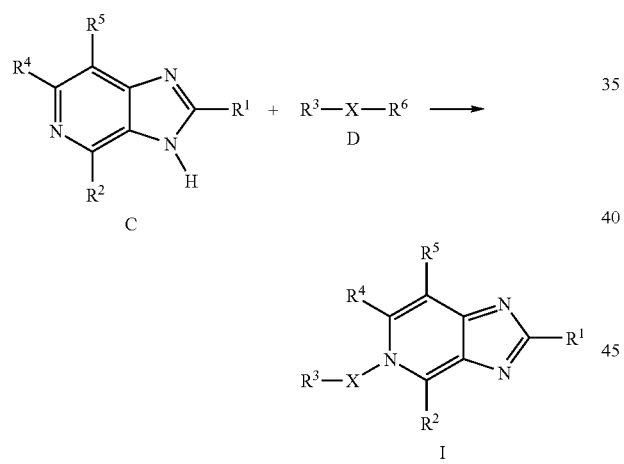

This reaction gives mixtures of three products (alkylation at the $N^1$, $N^3$ or $N^5$ of the imidazo[4,5-c]pyridine C, respectively). For example, reaction of imidazo[4,5-c]pyridine C $R^1$=2,6-difluorophenyl, $R^2$=$R^4$=$R^5$=H) with 2,6-difluorobenzyl bromide gave the following mixture (scheme 5):

Scheme 5:

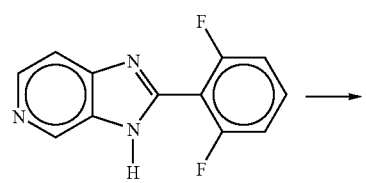

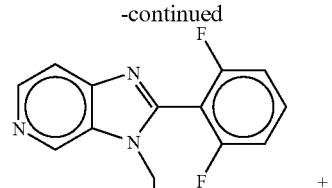

16%

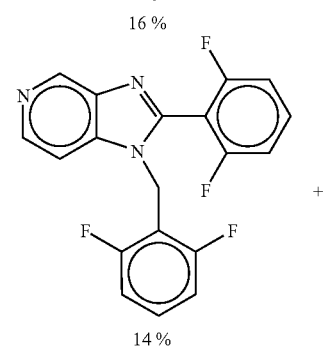

14%

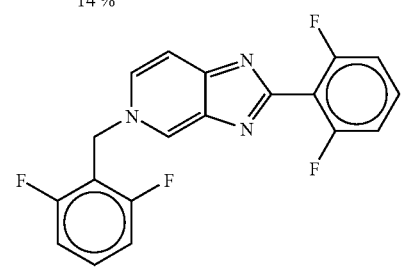

GPRTI-8 (65%)

This mixture can be separated by column chromatography (silica gel, eluent: mixture of dichloromethane and methanol). The structures of the isolated components can then be assigned by NMR spectroscopy (for example by one-dimensional NOE-techniques: irradiation at the $CH_2$ resonance frequency; applying this to GPRTI-8 gives signal enhancements of the protons in positions 4 and 6 of the imidazo[4,5-c] pyridine ringsystem) or by single crystal x-ray analysis.

Alternatively, the crude reaction mixture can be recrystallized from an appropriate solvent (mixture), e.g. from a mixture of diisopropyl ether and ethyl acetate, to give the pure $N^5$ alkylated products.

(Hetero)aromatic substituents on (hetero)aromatic rings ($R^2$, $R^4$, $R^5$, $R^6$, $R^{17}$, $R^{19}$) can be introduced by crosscoupling reactions, e.g. Suzuki coupling.

In the case of hydroxy, mercapto or amino substituents in position 4 or 6 of the imidazopyridine I (Z=O, S or NR), tautomers can be formulated:

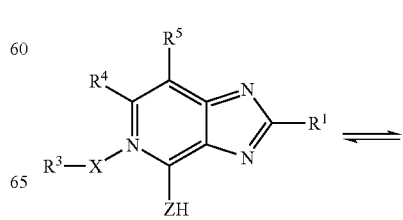

-continued

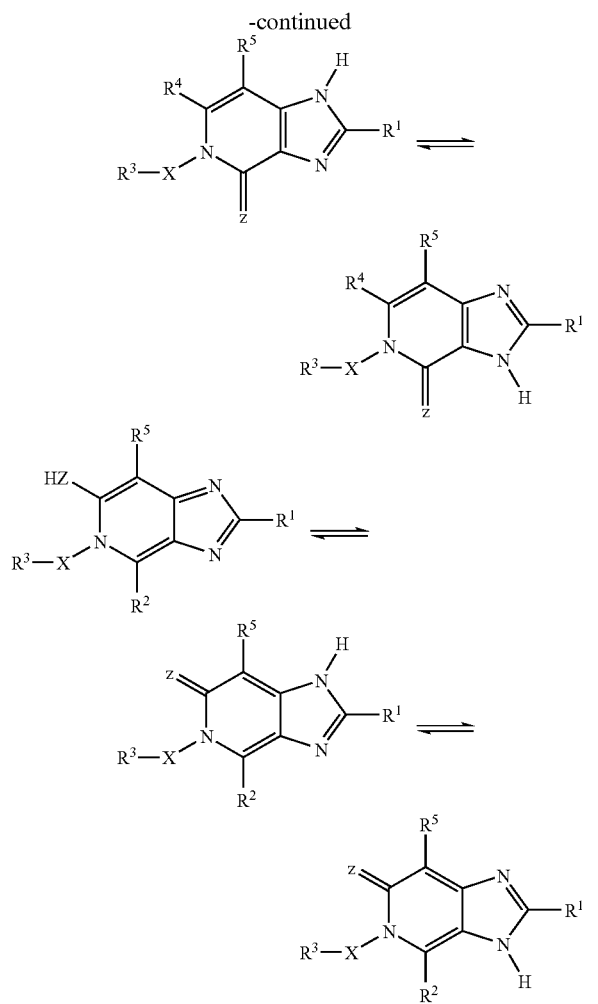

Therefore, an additional substituent ($R^{25}$) can be introduced at position 1 or 3 of the imidazo[4,5-c]pyridine:

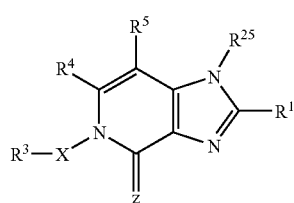

-continued

Compounds of general structure E, F, G and H can be prepared by alkylation (for example with (cyclo)alkylbromide or (cyclo)alkyliodide etc.) of the corresponding 1(3)H-imidazo[4,5-c]pyridin 4-ones (Z=O) or -thiones (Z=S) or -one-imines (Z=NR), or 1(3)H-imidazo[4,5-c]pyridin-6-ones or -thiones or -one-imines, respectively (scheme 6). The resulting mixtures can be separated by column chromatography. The required 1(3)H-imidazo[4,5-c]pyridine-4-ones or -thiones or -one-imines, or 1(3)H-imidazo[4,5-c]pyridine-6-ones or -thiones or -one-imines can, for example, be prepared from the corresponding 4- or 6-chloro-imidazo[4,5-c]pyridines by nucleophilic substitution. 1(3)H-Imidazo[4,5-c]pyridine-4-ones or -6-ones can also be prepared by ether cleavage of the corresponding 4 or 6-alkoxy-imidazo[4,5-c]pyridines.

Scheme 6:

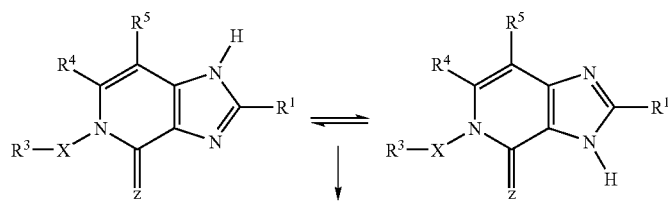

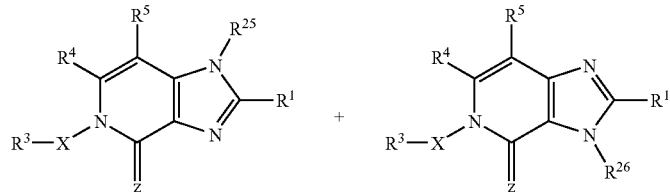

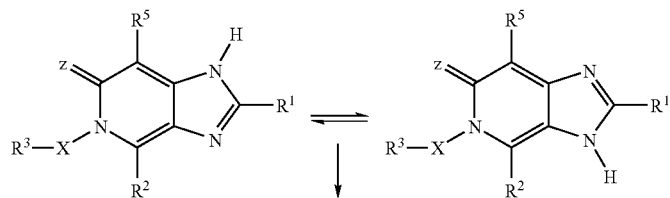

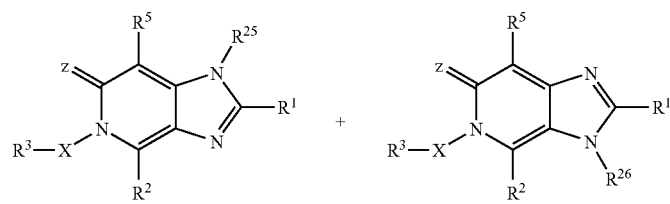

Alternatively, compounds of general structures E and G (Z=O) can be synthesized starting from (substituted) 2,4-dihydroxy-3-nitropyridine (scheme 7) or (substituted) 2,4-dihydroxy-5-nitropyridine, respectively. Introduction of the substituent in position 1 of the pyridine (for example by alkylation), followed by subsequent reaction with $POCl_3$ and an appropriate amine, reduction of the nitro function and cyclization gives the desired imidazo[4,5-c]pyridines E or G. These can be transformed into the corresponding thiones by reaction with phosphorus(V)-sulfide or Laweson's reagent or into the corresponding one-imines by reaction with phosphorus(III)-chloride/amine.

Scheme 7:

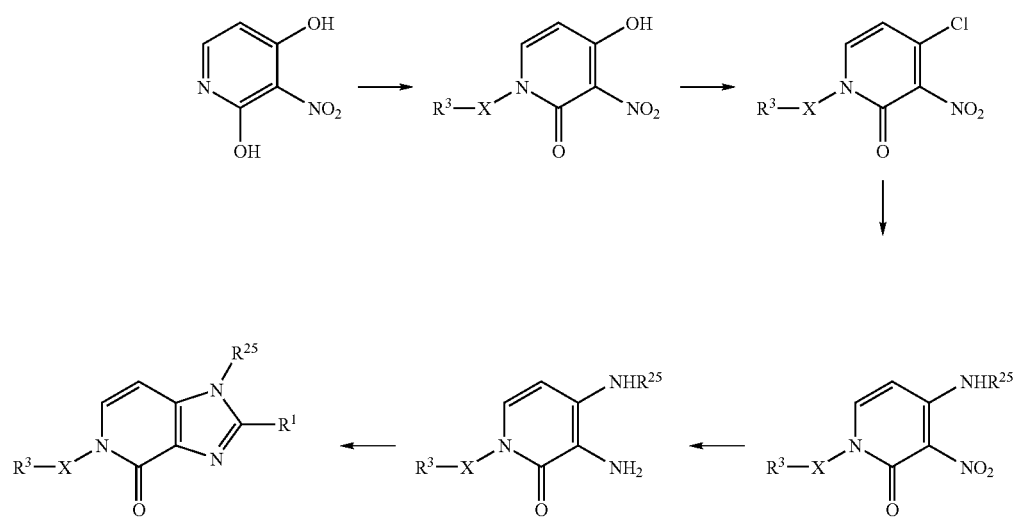

Another methods to introduce $R^{25}$ or $R^{26}$, respectively, is by reductive amination with a carbonyl reagent and sodium-cyanoborohydride, as exemplified in scheme 8:

Scheme 8:

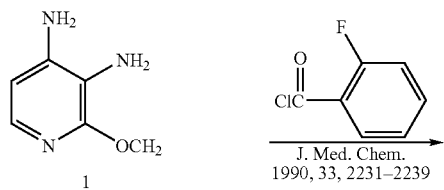

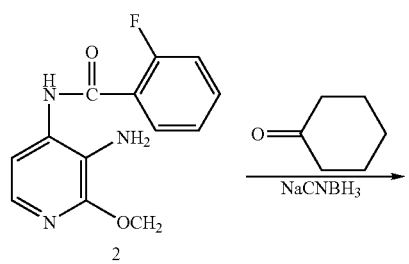

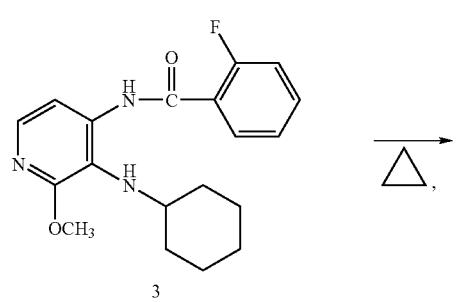

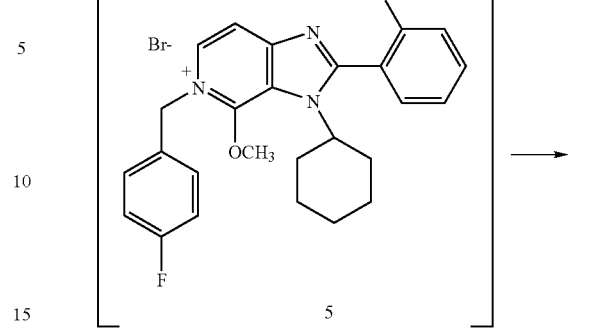

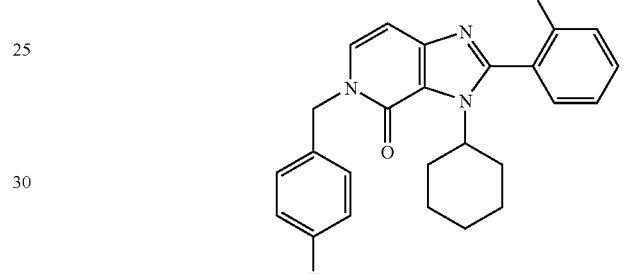

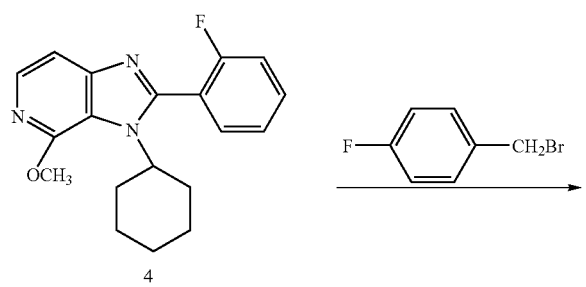

Monobenzoylation of a (substituted) 3,4-diaminopyridine, followed by reductive amination and cyclization gives the 1- or 3-substituted imidazo[4,5-c]pyridine. Quaternization, for example with a benzyl bromide, followed by cleavage of the 4-methoxy function, results in the desired imidazo[4,5-c] pyridinone.

Introduction of a carboxylic function (carboxylic acid, ester, amide) in position 6 of the imidazo[4,5-c]pyridine can be achieved by different routes. One involves the imidazo[4,5-c]pyridine $N^5$-oxide (for example obtained by N-oxidation of the corresponding imidazo[4,5-c]pyridine with meta-chlorperbenzoic acid (MCPBA) or with $H_2O_2$/methyl-trioxorhenium), which can be brominated in position 6. Removal of the N-oxygen (e.g. with iron in acetic acid), bromine/lithium exchange, for example with n-BuLi, followed by reaction with carbon dioxide, gives the desired 6-carboxy compounds. Another method is the conversion of the 6-bromo substituent into a carboxylic ester function by reaction with carbon monoxide in alcohol with palladium acetate as the catalyst. Yet another possibility is the reaction of the 4-substituted $N^5$-oxide with trimethylsilylcyanide/N,N-diethylcarbamoylchloride to give the 6-cyano product, which can be hydrolysed to the corresponding 6-carboxylic acid.

Scheme 9:
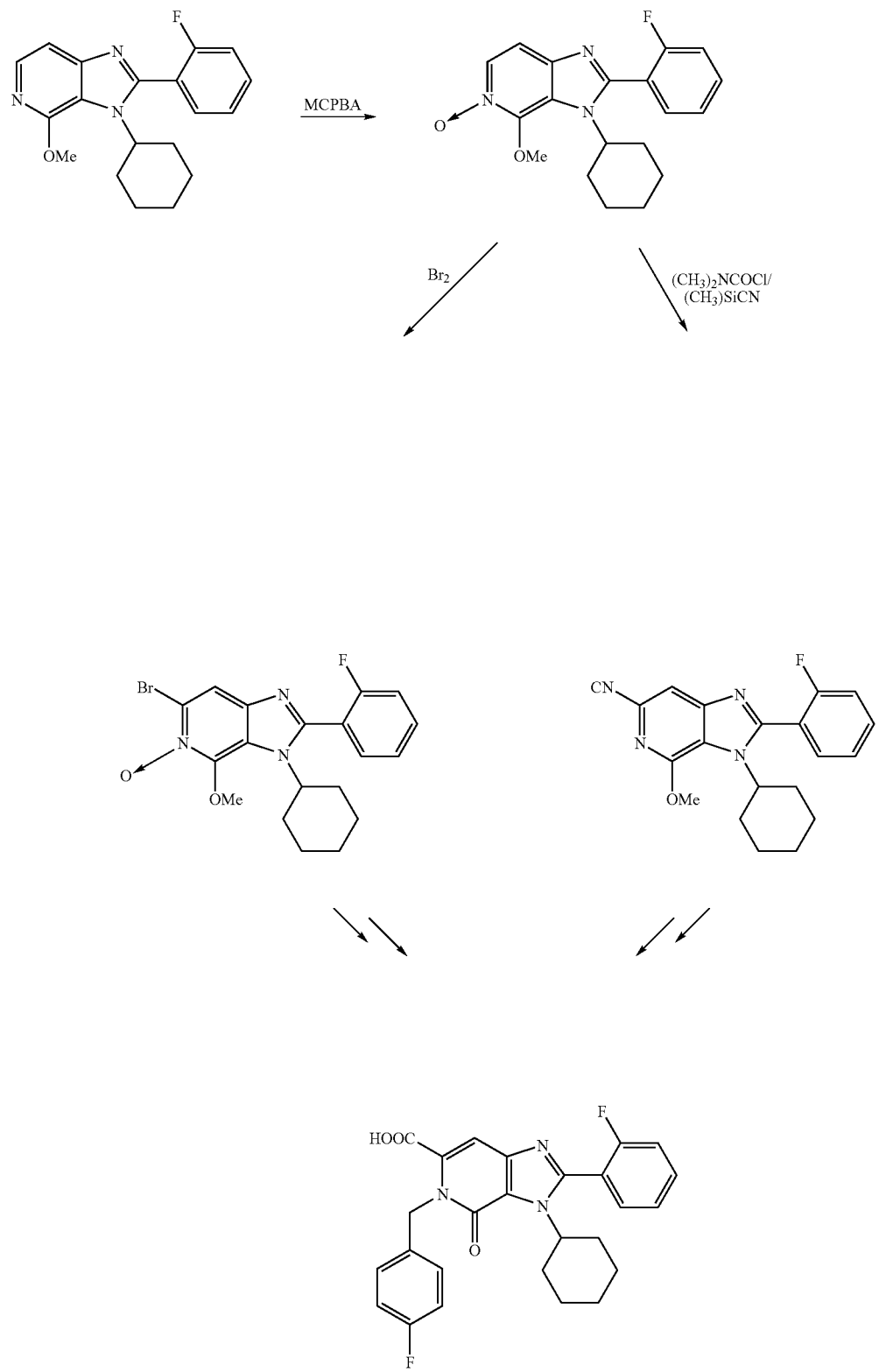

The 5-substituted idazo[4,5-c]pyridin-6-ones can be prepared by similar methodologies, as shown in scheme 10.

Scheme 10:

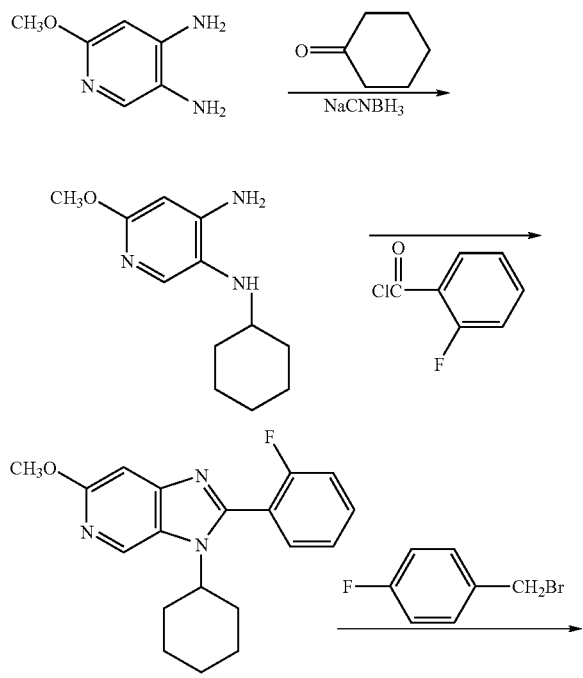

The 6-carboxy group can easily be converted into an amide function by reaction with an amine using DCC (dicyclohexyl carbodiimide):

Scheme 11:

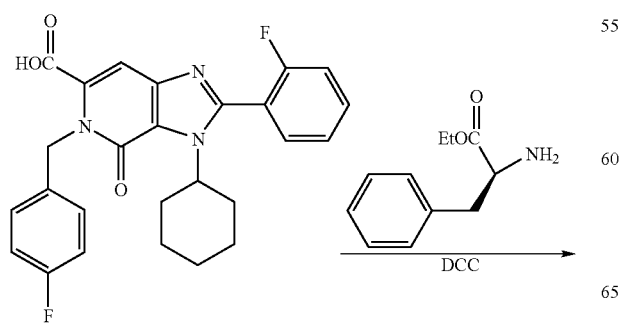

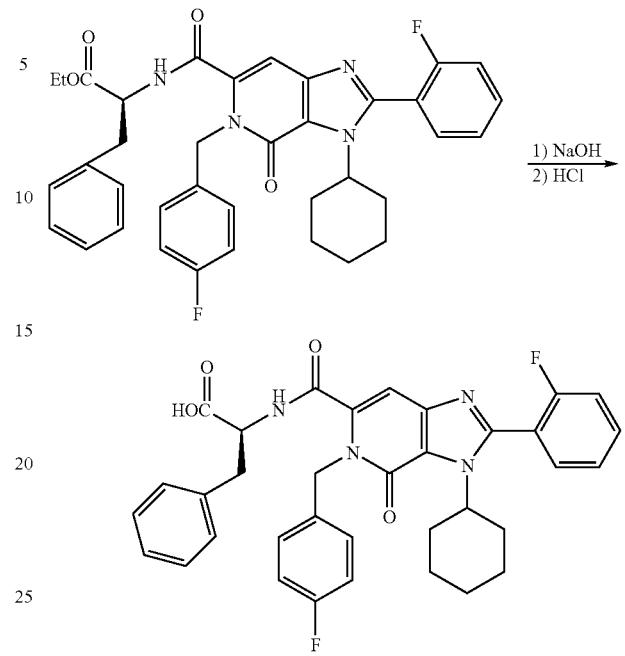

Alternatively, carboxyl groups can be introduced by oxidation (e.g. with KMnO$_4$) of the corresponding methyl analogues (scheme 12)

Scheme 12:

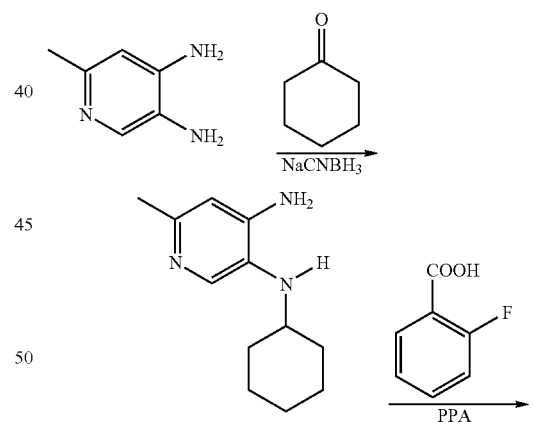

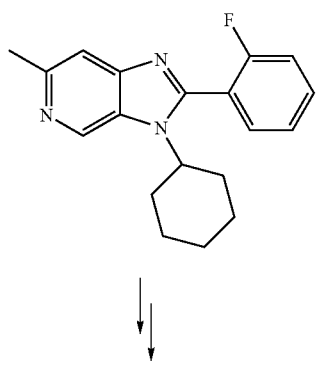

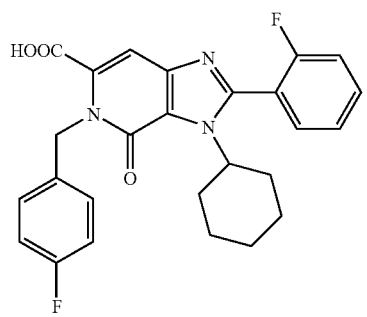

Scheme 13 shows further examples for the synthesis of compounds with a substituted (het)aryl in position 2 of the imidazo[4,5-c]pyridine ringsystem.

Scheme 13:

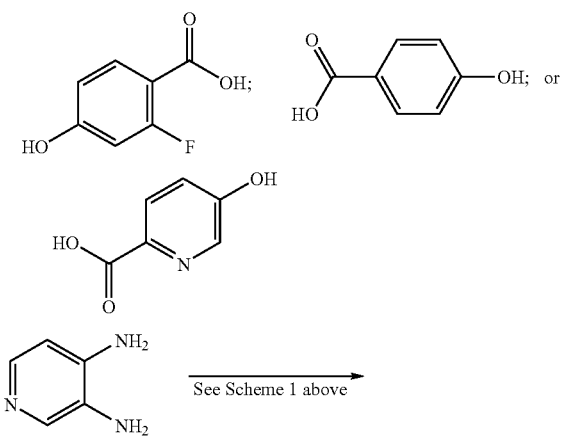

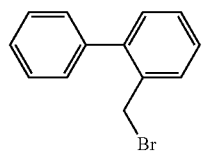

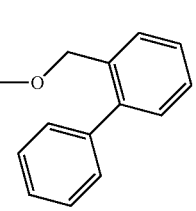

Analogous compounds are synthesized in the same fashion as in the foregoing schemes by varying the stating materials, intermediates, solvents and conditions as will be known by those skilled in the art.

EXAMPLES

The following examples illustrate the present invention without being limited thereto. Part A represent the preparation of the compounds whereas Part B represents the pharmacological examples.

TABLE 8

Structures of examples and their respective codes

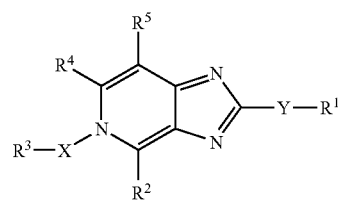

| Entry | code | X | Y | $R^1$ | $R^2$ | $R^3$ | $R^4$ | $R^5$ |
|---|---|---|---|---|---|---|---|---|
| 1 | GPRTI-8 | $CH_2$ | — | 2,6-difluorophenyl | H | 2,6-difluorophenyl | H | H |
| 2 | GPJN-1 | $CH_2$ | — | 2,6-difluorophenyl | H | phenyl | H | H |
| 3 | GPJN-2 | $CH_2$ | — | 2,6-difluorophenyl | H | phenyl | H | H |
| 4 | GPJN-3 | $CH_2$ | — | phenyl | H | 2,6-difluorophenyl | H | H |
| 5 | GPJN-4 | $CH_2$ | — | phenyl | H | phenyl | H | H |
| 6 | GPJN-7 | $CH_2$ | — | phenyl | H | 2-chorophenyl | H | H |
| 7 | GPJN-8 | $CH_2$ | — | phenyl | H | 3-chorophenyl | H | H |
| 8 | GPJN-9 | $CH_2$ | — | phenyl | H | 4-chorophenyl | H | H |
| 9 | GPJN-11 | $CH_2$ | — | phenyl | H | 2-methoxyphenyl | H | H |
| 10 | GPJN-12 | $CH_2$ | — | phenyl | H | 3-methoxyphenyl | H | H |

TABLE 8-continued

Structures of examples and their respective codes

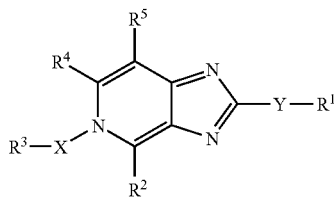

| Entry | code | X | Y | $R^1$ | $R^2$ | $R^3$ | $R^4$ | $R^5$ |
|---|---|---|---|---|---|---|---|---|
| 11 | GPJN-13 | $CH_2$ | — | phenyl | H | 4-methoxyphenyl | H | H |
| 12 | GPJN-14 | $(CH_2)_3$ | — | phenyl | H | phenyl | H | H |
| 13 | GPJN-15 | $CH_2$ | — | phenyl | H | 4-methylphenyl | H | H |
| 14 | GPJN-16 | $CH_2$ | — | phenyl | H | 4-(1,1-dimethylethyl)phenyl | H | H |
| 15 | GPJN-17 | $CH_2$ | — | phenyl | H | 2-fluorophenyl | H | H |
| 16 | GPJN-18 | $CH_2$ | — | phenyl | H | 3-fluorophenyl | H | H |
| 17 | GPJN-19 | $CH_2$ | — | phenyl | H | 4-fluorophenyl | H | H |
| 18 | GPJN-20 | $CH_2$ | — | phenyl | H | 2-methylphenyl | H | H |
| 19 | GPJN-21 | $CH_2$ | — | phenyl | H | 3-methylphenyl | H | H |
| 20 | GPJN-22 | CH | — | phenyl | H | 4-bromophenyl | H | H |
| 21 | GPJN-23 | $CH_2$ | — | phenyl | H | 4-cyanophenyl | H | H |
| 22 | GPJN-24 | $CH_2$ | — | phenyl | H | 4-(trifluoromethyl)phenyl | H | H |
| 23 | GPJN-25 | $CH_2$ | — | phenyl | H | 5-chloro-2-thienyl | H | H |
| 24 | GPJN-26 | $CH_2$ | — | phenyl | H | 2-naphthalenyl | H | H |
| 25 | GPJN-27 | $(CH_2)_4$ | — | phenyl | H | phenyl | H | H |
| 26 | GPJN-31 | $CH_2$ | — | phenyl | H | 4-pyridinyl | H | H |
| 27 | GPJN-32 | $CH_2$ | — | phenyl | H | 4-phenyl-phenyl | H | H |
| 28 | GPJN-33 | $CH(CH_3)$ | — | phenyl | H | phenyl | H | H |
| 29 | GPJN-34 | $CH_2$ | — | phenyl | H | 2-pyridinyl | H | H |
| 30 | GPJN-35 | $CH_2$ | — | phenyl | H | 3-pyridinyl | H | H |
| 31 | GPJN-36 | $CH_2$ | — | phenyl | H | 1-naphthalenyl | H | H |
| 32 | GPJN-37 | $CH_2$ | — | phenyl | H | cyclohexyl | H | H |
| 33 | GPJN-39 | $CH_2$ | — | 2,6-difluorophenyl | H | 4-fluorophenyl | H | H |
| 34 | GPJN-40 | $CH_2$ | — | 2,6-difluorophenyl | H | 2,4-difluorophenyl | H | H |
| 35 | GPJN-41 | $CH_2$ | — | 2,6-difluorophenyl | H | 2,4,6-trifluorophenyl | H | H |
| 36 | GPJN-42 | $CH_2$ | — | phenyl | H | 2-bromophenyl | H | H |
| 37 | GPJN-43 | $CH_2$ | — | phenyl | H | 3-bromophenyl | H | H |
| 38 | GPJN-44 | $CH_2$ | — | phenyl | H | 2-cyanophenyl | H | H |
| 39 | GPJN-45 | $CH_2$ | — | phenyl | H | 3-cyanophenyl | H | H |
| 40 | GPJN-46 | $CH_2$ | — | phenyl | H | 2-(trifluoromethyl)phenyl | H | H |
| 41 | GPJN-47 | $CH_2$ | — | phenyl | H | 3-(trifluoromethyl)phenyl | H | H |
| 42 | GPJN-48 | $CH_2$ | $(CH_2)_2$ | H | H | 4-bromophenyl | H | H |
| 43 | GPJN-49 | $CH_2$ | — | 4-pyridyl | H | 4-bromophenyl | H | H |
| 44 | GPJN-50 | $CH_2$ | — | 3-fluorophenyl | H | 4-bromophenyl | H | H |
| 45 | GPJN-51 | $CH_2$ | — | 4-fluorophenyl | H | 4-bromophenyl | H | H |
| 46 | GPJN-52 | $CH_2$ | — | 2-fluorophenyl | H | 4-bromophenyl | H | H |
| 47 | GPJN-53 | $CH_2$ | — | 2-thienyl | H | 4-bromophenyl | H | H |
| 48 | GPJN-54 | $CH_2$ | — | 2-chlorophenyl | H | 4-bromophenyl | H | H |
| 49 | GPJN-55 | $CH_2$ | — | 3-chlorophenyl | H | 4-bromophenyl | H | H |
| 50 | GPJN-56 | $CH_2$ | — | 4-chlorophenyl | H | 4-bromophenyl | H | H |
| 51 | GPJN-57 | $CH_2$ | — | 3-pyridyl | H | 4-bromophenyl | H | H |
| 52 | GPJN-58 | $CH_2$ | — | 2-pyridyl | H | 4-bromophenyl | H | H |
| 53 | GPJN-59 | $CH_2$ | — | 2-methylphenyl | H | 4-bromophenyl | H | H |
| 54 | GPJN-60 | $CH_2$ | — | 3-methylphenyl | H | 4-bromophenyl | H | H |
| 55 | GPJN-61 | $CH_2$ | — | 4-methylphenyl | H | 4-bromophenyl | H | H |
| 56 | GPJN-62 | $CH_2$ | — | 1-naphtalenyl | H | 4-bromophenyl | H | H |
| 57 | GPJN-63 | $CH_2$ | — | 2-naphtalenyl | H | 4-bromophenyl | H | H |
| 58 | GPJN-64 | $CH_2$ | — | 3-methoxyphenyl | H | 4-bromophenyl | H | H |
| 59 | GPJN-65 | $CH_2$ | — | 3-bromophenyl | H | 4-bromophenyl | H | H |
| 60 | GPJN-66 | $CH_2$ | — | 3-(dimethylamino)phenyl | H | 4-bromophenyl | H | H |
| 61 | GPJN-67 | $CH_2$ | $(CH_2)_1$ | phenyl | H | 4-bromophenyl | H | H |
| 62 | GPJN-68 | $CH_2$ | — | phenyl | H | 4-iodophenyl | H | H |
| 63 | GPJN-69 | $CH_2$ | — | 3-iodophenyl | H | 4-bromophenyl | H | H |
| 64 | GPJN-70 | $CH_2$ | — | 2-bromophenyl | H | 4-bromophenyl | H | H |
| 65 | GPJN-73 | $O—CH_2—CH_2$ | - | phenyl | H | phenyl | H | H |
| 66 | GPJN-74 | $CH_2$ | — | phenyl | H | 3,4-dichlorophenyl | H | H |
| 67 | GPJN-75 | $CH=CH—CH_2$ | — | phenyl | H | phenyl | H | H |
| 68 | GPJN-76 | $CH_2$ | $(CH_2)_2$ | phenyl | H | 4-bromophenyl | H | H |
| 69 | GPJN-77 | $CH_2$ | $(CH_2)_3$ | phenyl | H | 4-bromophenyl | H | H |
| 70 | GPJN-78 | $CH_2$ | — | 3,5-dibromphenyl | H | 4-bromophenyl | H | H |
| 71 | GPJN-79 | $CH_2$ | — | 3-bromophenyl | H | 4-iodophenyl | H | H |

TABLE 8-continued

Structures of examples and their respective codes

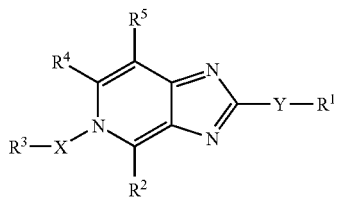

| Entry | code | X | Y | $R^1$ | $R^2$ | $R^3$ | $R^4$ | $R^5$ |
|---|---|---|---|---|---|---|---|---|
| 72 | GPJN-80 | $CH_2$ | — | 3-bromophenyl | H | 4-chlorophenyl | H | H |
| 73 | GPJN-81 | $CH_2$ | CH=CH | phenyl | H | 4-bromophenyl | H | H |
| 74 | GPJN-82 | $CH_2$ | $CH_2$—O | phenyl | H | 4-bromophenyl | H | H |
| 75 | GPJN-83 | $CH_2$ | $CH_2$—S | phenyl | H | 4-bromophenyl | H | H |
| 76 | GPJN-84 | $CH_2$ | — | 3-bromophenyl | H | 3,4-dichlorophenyl | H | H |
| 77 | GPJN-85 | $CH_2$ | $(CH_2)_4$ | phenyl | H | 4-bromophenyl | H | H |
| 78 | GPJN-86 | $CH_2$ | — | 5-bromo-2-thienyl | H | 4-bromophenyl | H | H |
| 79 | GPJN-87 | $CH_2$ | — | 3-(trifluoromethyl)phenyl | H | 4-bromophenyl | H | H |
| 80 | GPJN-88 | $CH_2$ | — | phenyl | H | 4-(trifluoromethoxy)phenyl | H | H |
| 81 | GPJN-89 | $CH_2$ | — | 2,3,6-trifluorophenyl | H | 4-bromophenyl | H | H |
| 82 | GPJN-90 | $CH_2$ | — | 2,5-difluorophenyl | H | 4-bromophenyl | H | H |
| 83 | GPJN-91 | $CH_2$ | — | phenyl | H | 4-bromophenyl | H | Br |
| 84 | GPJN-94 | $CH_2$ | — | phenyl | H | 4-carboxyphenyl | H | H |
| 85 | GPJN-95 | $CH_2$ | — | phenyl | CH | 4-bromophenyl | H | H |
| 86 | GPJN-96 | $CH_2$ | — | phenyl | Cl | 4-bromophenyl | H | H |
| 87 | GPJN-98 | $(CH_2)_2$ | $(CH_2)_1$ | phenyl | H | phenyl | H | H |
| 88 | GPJN-99 | $(CH_2)_3$ | — | 3-bromophenyl | H | phenyl | H | H |
| 89 | GPJN-100 | O—$CH_2$—$CH_2$ | — | 3-bromophenyl | H | phenyl | H | H |
| 90 | GPJN-103 | $CH_2$ | — | phenyl | H | 4-bromophenyl | H | Cl |
| 91 | GPJN-104 | $CH_2$ | — | phenyl | H | 4-bromophenyl | H | $CH_3$ |
| 92 | GPJN-105 | $CH_2$ | — | 2-fluorophenyl | H | phenyl | H | H |
| 93 | GPJN-106 | $CH_2$ | — | 2-fluorophenyl | H | 2-methylphenyl | H | H |
| 94 | GPJN-107 | $CH_2$ | — | 2-fluorophenyl | H | 3-methylphenyl | H | H |
| 95 | GPJN-108 | $CH_2$ | — | 2-fluorophenyl | H | 4-methylphenyl | H | H |
| 96 | GPJN-109 | $CH_2$ | — | phenyl | $CH_3$ | 4-bromophenyl | H | H |
| 97 | GPJN-110 | $CH_2$ | — | 2-fluorophenyl | H | 4-phenyl-phenyl | H | H |
| 98 | GPJN-111 | $CH_2$ | $CH_2$—S | phenyl | H | 4-phenyl-phenyl | H | H |
| 99 | GPJN-112 | $CH_2$ | — | 2-fluorophenyl | H | 4-chlorophenyl | H | H |
| 100 | GPJN-113 | $CH_2$ | — | 2-fluorophenyl | H | 4-iodophenyl | H | H |
| 101 | GPJN-114 | $CH_2$ | — | 2-fluorophenyl | H | 4-(1,1-dimethylethyl)phenyl | H | H |
| 102 | GPJN-115 | $CH_2$ | — | 1-naphtalenyl | H | 4-phenyl-phenyl | H | H |
| 103 | GPC-10 | $CH_2$ | — | 2,6-difluorophenyl | H | 3,4-dichlorophenyl | H | H |
| 104 | GPC-11 | $CH_2$ | — | 3-fluorophenyl | H | 2,4-difluorophenyl | H | H |
| 105 | GPC-12 | $CH_2$ | — | 2,3,6-trifluorophenyl | H | 2,4-difluorophenyl | H | H |
| 106 | GPC-13 | $CH_2$ | — | 2,5-difluorophenyl | H | 2,4-difluorophenyl | H | H |

Part A

Example 1

Preparation of 2-(2,6-Difluorophenyl)-1(3)H-imidazo[4,5-c]pyridine

A mixture of 3,4-diaminopyridine (2.00 g), 2,6-difluorobenzoic acid (1 equivalent) and polyphosphoric acid (50 g) was heated at 180° C. for 4 h with stirring. Then the mixture was cooled to ambient temperature and poured into ice/water. The resulting mixture was neutralized by addition of solid $Na_2CO_3$. The crude product was collected by filtration, washed with water and dried. It was used in the next step without further purification.

Recrystallized from water; brownish crystals; mp: 189-190° C.; yield: 60%; $^1$H NMR (200 MHz, DMSO-d6) δ 13.20 (br s, 1H, NH), 9.04 (br s, 1H, H4), 8.37 (br d, 1H, H6, J=5.4 Hz), 7.76-7.61 (m, 2H, H7/4'), 7.42-7.30 (m, 2H, H3'/5').

Example 2

Preparation of 2-Phenyl-1(3)H-imidazo[4,5-c]pyridine (GPJN-10)

A mixture of 3,4-diaminopyridine (2.00 g), benzoic acid (1 equivalent) and polyphosphoric acid (50 g) was heated at 190° C. for 3 h with stirring. Then the mixture was cooled to ambient temperature and poured into ice/water. The resulting mixture was neutralized by addition of solid $Na_2CO_3$. The crude product was collected by filtration, washed with water and dried. It was used in the next step without further purification.

Recrystallized from water; off-white crystals; mp: 229-230° C.; yield: 96%; $^1$H NMR (200 MHz, DMSO-$d_6$) δ 8.95 (d, 1H, H4, J=1.0 Hz), 8.31 (d, 1H, H6, J=5.4 Hz), 8.28-8.17 (m, 2H, arom. H), 7.64-7.50 (m, 4H, arom. H).

Example 3

Preparation of 2-(2,6-Difluorophenyl)-5-[(2,6-difluorophenyl)methyl]-5H-imidazo[4,5-c]pyridine (GPRTI-8)

2-(2,6-Difluorophenyl)-1(3)H-imidazo[4,5-c]pyridine (0.500 g) was dissolved in dry DMF (5 mL) and the resulting solution was cooled to 0° C. Aqueous 50% sodium hydroxide (1.5 equivalents) was added and the mixture was stirred for 15 min. Then 2,6-difluorobenzyl bromide (1.2 equivalents) was added portionwise and the resulting mixture was stirred for 24 h at room temperature. Finally, water (50 mL) was added, the precipitate was collected by filtration and dried to give the crude product mixture.

Recrystallized from ethyl acetate; colorless crystals; mp: 195-197° C.; yield: 65%; $^1$H NMR (200 MHz, DMSO-d6) δ 9.08 (br s, 1H, H4), 8.09 (dd, 1H, H6, J=6.6, 1.7 Hz), 7.82 (d, 1H, H7, J=6.6 Hz), 7.63-7.46 (m, 2H, H4'/4''), 7.29-7.13 (m, 4H, H3'/5'/3''/5''), 5.87 (s, 2H, CH$_2$); MS (EI, 70 eV) m/z 357 (M$^+$, 77%), 338 (4%), 230 (11%), 127 (100%); Anal. (C$_{19}$H$_{11}$F$_4$N$_3$) calcd.: C 63.87%, H 3.10%, N 11.76%, found: C 63.83%, H 3.15%, N 11.63%.

Example 4

Preparation of 5-Benzyl-2-(2,6-difluorophenyl)-5H-imidazo[4,5-c]pyridine (GPJN-1)

Prepared as described in example 3 from 2-(2,6-difluorophenyl)-1(3)H-imidazo[4,5-c]pyridine (0.500 g) and benzyl bromide (0.444 g, 1.2 equivalents).

Recrystallized from a mixture of diisopropyl ether and ethyl acetate; off-white crystals; mp: 180-181° C. (degr.); yield: 30%; $^1$H NMR (200 MHz, DMSO-d$_6$) δ 9.24 (br d, 1H, H4, J=1.5 Hz), 8.25 (dd, 1H, H6, J=6.9, 1.5 Hz), 7.81 (d, 1H, H7, J=6.9 Hz), 7.60-7.33 (m, 6H, H4'/2''/3''/4''/5''/6''), 7.26-7.13 (m, 2H, H3'/5'), 5.71 (s, 2H, CH$_2$).

Example 5

Preparation of 5-[(2,6-Difluorophenyl)methyl]-2-phenyl-5H-imidazo[4,5-c]pyridine (GPJN-3)

Prepared as described in example 3 from 2-phenyl-1(3)H-imidazo[4,5-c]pyridine (0.500 g) and 2,6-difluorobenzyl bromide (0.636 g, 1.2 equivalents).

Recrystallized from a mixture of diisopropyl ether (25 mL) and ethyl acetate (60 mL); colorless crystals; mp: 214-216° C.; yield: 64%; $^1$H NMR (200 MHz, DMSO-d$_6$) δ 8.91 (br s, 1H, H4), 8.39-8.32 (m, 2H, arom. H), 8.01 (dd, 1H, H6, J=6.9, 1.5 Hz), 7.72 (d, 1H, H7, J=6.9 Hz), 7.63-7.37 (m, 4H, arom. H), 7.30-7.16 (m, 2H, H3'/5'), 5.81 (s, 2H, CH$_2$).

Example 6

Preparation of 5-Benzyl-2-phenyl-5H-imidazo[4,5-c]pyridine (GPJN-4)

Prepared as described in example 3 from 2-phenyl-1(3)H-imidazo[4,5-c]pyridine (0.500 g) and benzyl bromide (0.526 g, 1.2 equivalents).

Recrystallized from a mixture of diisopropyl ether (25 mL), ethyl acetate (50 mL) and methanol (4 mL); colorless crystals; mp: 214-216° C.; yield: 33%; $^1$H NMR (200 MHz, DMSO-d$_6$) δ 9.09 (d, 1H, H4, J=1.4 Hz), 8.40-8.33 (m, 2H, arom. H), 8.18 (dd, 1H, H6, J=6.9, 1.4 Hz), 7.73 (d, 1H, H7, J=6.9 Hz), 7.52-7.32 (m, 8H, arom. H), 5.66 (s, 2H, CH$_2$).

Example 7

Preparation of 2-(2,6-Difluorophenyl)-5-(2-phenylethyl)-5H-imidazo[4,5-c]pyridine (GPJN-2)

Prepared as described in example 3 from 2-(2,6-difluorophenyl)-1(3)H-imidazo[4,5-c]pyridine (0.500 g) and 2-phenylethyl bromide (0.480 g, 1.2 equivalents).

Recrystallized from a mixture of diisopropyl ether (50 mL) and ethyl acetate (40 mL); off-white crystals; mp: 184-186° C. (degr.); yield: 14%; $^1$H NMR (200 MHz, DMSO-d$_6$) δ 9.02 (br d, 1H, H4, J=1.4 Hz), 8.09 (dd, 1H, H6, J=6.7, 1.4 Hz), 7.74 (d, 1H, H7, J=6.7 Hz), 7.60-7.45 (m, 1H, H4'), 7.34-7.12 (m, 7H, H3'/5'/2''/3''/4''/5''/6''), 4.74 (t, 2H, N—CH$_2$, J=7.4 Hz), 3.26 (t, 2H, CH$_2$, J=7.4 Hz).

Example 8

Preparation of 2-Phenyl-5-(3-phenylpropyl)-5H-imidazo[4,5-c]pyridine (GPJN-14)

Prepared as described in example 3 from 2-phenyl-1(3)H-imidazo[4,5-c]pyridine (0.300 g) and 1-bromo-3-phenylpropane (0.367 g, 1.2 equivalents).

Recrystallized from a mixture of diisopropyl ether (10 mL) and ethyl acetate (7 mL); off-white crystals; mp: 44-46° C.; yield: 44%; $^1$H NMR (200 MHz, DMSO-d$_6$) δ 8.95 (d, 1H, H4, J=1.4 Hz), 8.40-8.33 (m, 2H, arom. H), 8.09 (dd, 1H, H6, J=6.8, 1.4 Hz), 7.71 (d, 1H, H7, J=6.8 Hz), 7.52-7.13 (m, 8H, arom. H), 4.84 (t, 2H, N—CH$_2$, J=7.2 Hz), 2.65-2.57 (m, 2H, CH$_2$), 2.31-2.16 (m, 2H, CH$_2$).

Example 9

Preparation of 5-[(2-Chlorophenyl)methyl]-2-phenyl-5H-imidazo[4,5-c]pyridine (GPJN-7)

Prepared as described in example 3 from 2-phenyl-1(3)H-imidazo[4,5-c]pyridine (0.300 g) and 2-chlorobenzyl chloride (0.297 g, 1.2 equivalents).

Recrystallized from a mixture of diisopropyl ether (25 mL) and ethyl acetate (65 mL); colorless crystals; mp: 224-225° C.; yield: 52%; $^1$H NMR (200 MHz, DMSO-d$_6$) δ 8.99 (d, 1H, H4, J=1.6 Hz), 8.40-8.33 (m, 2H, arom. H), 8.10 (dd, 1H, H6, J=6.7, 1.6 Hz), 7.75 (d, 1H, H7, J=6.7 Hz), 7.59-7.34 (m, 6H, arom. H), 7.18-7.12 (m, 1H, arom. H), 5.80 (s, 2H, CH$_2$).

Example 10

Preparation of 5-[(3-Chlorophenyl)methyl]-2-phenyl-5H-imidazo[4,5-c]pyridine (GPJN-8)

Prepared as described in example 3 from 2-phenyl-1(3)H-imidazo[4,5-c]pyridine (0.300 g) and 3-chlorobenzyl bromide (0.379 g, 1.2 equivalents).

Recrystallized from a mixture of diisopropyl ether (10 mL) and ethyl acetate (27 mL); colorless crystals; mp: 210-212° C.; yield: 54%; $^1$H NMR (200 MHz, DMSO-d$_6$) δ 9.12 (d, 1H, H4, J=1.5 Hz), 8.39-8.32 (m, 2H, arom. H), 8.20 (dd, 1H, H6, J=6.7, 1.5 Hz), 7.74 (d, 1H, H7, J=6.7 Hz), 7.61-7.38 (m, 7H, arom. H), 5.66 (s, 2H, $CH_2$).

Example 11

Preparation of 5-[(4-Chlorophenyl)methyl]-2-phenyl-5H-imidazo[4,5-c]pyridine (GPJN-9)

Prepared as described in example 3 from 2-phenyl-1(3)H-imidazo[4,5-c]pyridine (0.300 g) and 4-chlorobenzyl chloride (0.297 g, 1.2 equivalents).

Recrystallized from a mixture of diisopropyl ether (10 mL) and ethyl acetate (24 mL); colorless crystals; mp: 211-212° C.; yield: 55%; $^1$H NMR (200 MHz, DMSO-$d_6$) δ 9.09 (d, 1H, H4, J=1.5 Hz), 8.40-8.33 (m, 2H, arom. H), 8.17 (dd, 1H, H6, J=6.9, 1.5 Hz), 7.73 (d, 1H, H7, J=6.9 Hz), 7.52-7.40 (m, 7H, arom. H), 5.66 (s, 2H, $CH_2$).

Example 12

Preparation of 5-[(2-Methoxyphenyl)methyl]-2-phenyl-5H-imidazo[4,5-c]pyridine (GPJN-11)

Prepared as described in example 3 from 2-phenyl-1(3)H-imidazo[4,5-c]pyridine (0.300 g) and 2-methoxybenzyl chloride (0.288 g, 1.2 equivalents).

Recrystallized from a mixture of diisopropyl ether (10 mL) and ethyl acetate (30 mL); colorless crystals; mp: 182-184° C.; yield: 60%; $^1$H NMR (200 MHz, DMSO-$d_6$) δ 8.94 (d, 1H, H4, J=1.6 Hz), 8.39-8.32 (m, 2H, arom. H), 8.08 (dd, 1H, H6, J=6.7, 1.6 Hz), 7.69 (d, 1H, H7, J=6.7 Hz), 7.51-7.29 (m, 5H, arom. H), 7.10-6.94 (m, 2H, arom. H), 5.61 (s, 2H, $CH_2$), 3.84 (s, 3H, $OCH_3$).

Example 13

Preparation of 5-[(3-Methoxyphenyl)methyl]-2-phenyl-5H-imidazo[4,5-c]pyridine (GPJN-12)

Prepared as described in example 3 from 2-phenyl-1(3)H-imidazo[4,5-c]pyridine (0.300 g) and 3-methoxybenzyl chloride (0.288 g, 1.2 equivalents).

Recrystallized from a mixture of diisopropyl ether (10 mL) and ethyl acetate (23 mL); colorless crystals; mp: 157-158° C.; yield: 62%; $^1$H NMR (200 MHz, DMSO-$d_6$) δ 9.10 (d, 1H, H4, J=1.7 Hz), 8.40-8.33 (m, 2H, arom. H), 8.18 (dd, 1H, H6, J=6.7, 1.7 Hz), 7.72 (d, 1H, H7, J=6.7 Hz), 7.52-7.27 (m, 4H, arom. H), 7.10-6.89 (m, 3H, arom. H), 5.61 (s, 2H, $CH_2$), 3.75 (s, 3H, $OCH_3$).

Example 14

Preparation of 5-[(4-Methoxyphenyl)methyl]-2-phenyl-5H-imidazo[4,5-c]pyridine (GPJN-13)

Prepared as described in example 3 from 2-phenyl-1(3)H-imidazo[4,5-c]pyridine (0.300 g) and 4-methoxybenzyl chloride (0.288 g, 1.2 equivalents).

Recrystallized from a mixture of diisopropyl ether (10 mL) and ethyl acetate (31 mL); colorless crystals; mp: 211-212° C.; yield: 52%; $^1$H NMR (200 MHz, DMSO-$d_6$) δ 9.07 (d, 1H, H4, J=1.5 Hz), 8.39-8.32 (m, 2H, arom. H), 8.16 (dd, 1H, H6, J=6.9, 1.5 Hz), 7.70 (d, 1H, H7, J=6.9 Hz), 7.51-7.37 (m, 5H, arom. H), 6.99-6.92 (AA'BB', 2H, arom. H), 5.57 (s, 2H, $CH_2$), 3.73 (s, 3H, $OCH_3$).

Example 15

Preparation of 5-[(2-Methylphenyl)methyl]-2-phenyl-5H-imidazo[4,5-c]pyridine (GPJN-20)

Prepared as described in example 3 from 2-phenyl-1(3)H-imidazo[4,5-c]pyridine (0.300 g) and 2-methylbenzyl chloride (0.259 g, 1.2 equivalents).

Recrystallized from a mixture of diisopropyl ether (10 mL) and ethyl acetate (44 mL); colorless crystals; mp: 223-224° C.; yield: 60%; $^1$H NMR (200 MHz, DMSO-$d_6$) δ 8.93 (d, 1H, H4, J=1.6 Hz), 8.41-8.33 (m, 2H, arom. H), 8.04 (dd, 1H, H6, J=6.7, 1.6 Hz), 7.75 (d, 1H, H7, J=6.7 Hz), 7.53-7.15 (m, 5H, arom. H), 6.92 (br d, 1H, arom. H, J=7.0 Hz), 5.73 (s, 2H, $CH_2$), 2.32 (s, 3H, $CH_3$).

Example 16

Preparation of 5-[(3-Methylphenyl)methyl]-2-phenyl-5H-imidazo[4,5-c]pyridine (GPJN-21)

Prepared as described in example 3 from 2-phenyl-1(3)H-imidazo[4,5-c]pyridine (0.300 g) and 3-methylbenzyl chloride (0.259 g, 1.2 equivalents).

Recrystallized from a mixture of diisopropyl ether (10 mL) and ethyl acetate (15 mL); colorless crystals; mp: 183-185° C.; yield: 46%; $^1$H NMR (200 MHz, DMSO-$d_6$) δ 9.08 (d, 1H, H4, J=1.5 Hz), 8.40-8.33 (m, 2H, arom. H), 8.16 (dd, 1H, H6, J=6.7, 1.5 Hz), 7.72 (d, 1H, H7, J=6.7 Hz), 7.52-7.14 (m, 7H, arom. H), 5.61 (s, 2H, $CH_2$), 2.29 (s, 3H, $CH_3$).

Example 17

Preparation of 5-[(4-Methylphenyl)methyl]-2-phenyl-5H-imidazo[4,5-c]pyridine (GPJN-15)

Prepared as described in example 3 from 2-phenyl-1(3)H-imidazo[4,5-c]pyridine (0.300 g) and 4-methylbenzyl chloride (0.259 g, 1.2 equivalents).

Recrystallized from a mixture of diisopropyl ether (10 mL) and ethyl acetate (32 mL); colorless crystals; mp: 206-208° C.; yield: 57%; $^1$H NMR (200 MHz, DMSO-$d_6$) δ 9.07 (d, 1H, H4, J=1.5 Hz), 8.39-8.32 (m, 2H, arom. H), 8.15 (dd, 1H, H6, J=6.7, 1.5 Hz), 7.71 (d, 1H, H7, J=6.7 Hz), 7.52-7.17 (m, 7H, arom. H), 5.60 (s, 2H, $CH_2$), 2.28 (s, 3H, $CH_3$).

Example 18

Preparation of 5-[(2-Fluorophenyl)methyl]-2-phenyl-5H-imidazo[4,5-c]pyridine (GPJN-17)

Prepared as described in example 3 from 2-phenyl-1(3)H-imidazo[4,5-c]pyridine (0.300 g) and 2-fluorobenzyl bromide (0.349 g, 1.2 equivalents).

Recrystallized from a mixture of diisopropyl ether (10 mL) and ethyl acetate (37 mL); colorless crystals; mp: 209-211° C.; yield: 67%; $^1$H NMR (200 MHz, DMSO-$d_6$) δ 9.01 (br s, 1H, H4), 8.41-8.33 (m, 2H, arom. H), 8.06 (dd, 1H, H6, J=6.8, 1.6 Hz), 7.74 (d, 1H, H7, J=6.8 Hz), 7.52-7.21 (m, 7H, arom. H), 5.76 (s, 2H, $CH_2$).

Example 19

Preparation of 5-[(3-Fluorophenyl)methyl]-2-phenyl-5H-imidazo[4,5-c]pyridine (GPJN-18)

Prepared as described in example 3 from 2-phenyl-1(3)H-imidazo[4,5-c]pyridine (0.300 g) and 3-fluorobenzyl bromide (0.349 g, 1.2 equivalents).

Recrystallized from a mixture of diisopropyl ether (10 mL) and ethyl acetate (34 mL); colorless crystals; mp: 228-230° C.; yield: 55%; $^1$H NMR (200 MHz, DMSO-$d_6$) δ 9.12 (d, 1H, H4, J=1.5 Hz), 8.41-8.33 (m, 2H, arom. H), 8.20 (dd, 1H, H6, J=6.7, 1.5 Hz), 7.74 (d, 1H, H7, J=6.7 Hz), 7.52-7.15 (m, 7H, arom. H), 5.67 (s, 2H, $CH_2$).

Example 20

Preparation of 5-[(4-Fluorophenyl)methyl]-2-phenyl-5H-imidazo[4,5-c]pyridine (GPJN-19)

Prepared as described in example 3 from 2-phenyl-1(3)H-imidazo[4,5-c]pyridine (0.300 g) and 4-fluorobenzyl chloride (0.267 g, 1.2 equivalents).

Recrystallized from a mixture of diisopropyl ether (10 mL) and ethyl acetate (19 mL); colorless crystals; mp: 205-206° C.; yield: 56%; $^1$H NMR (200 MHz, DMSO-$d_6$) δ 9.11 (d, 1H, H4, J=1.7 Hz), 8.40-8.33 (m, 2H, arom. H), 8.18 (dd, 1H, H6, J=6.8, 1.7 Hz), 7.73 (d, 1H, H7, J=6.8 Hz), 7.61-7.37 (m, 5H, arom. H), 7.30-7.18 (m, 2H, arom. H), 5.64 (s, 2H, $CH_2$).

Example 21

Preparation of 5-[[4-(1,1-Dimethylethyl)phenyl]methyl]-2-phenyl-5H-imidazo[4,5-c]pyridine (GPJN-16)

Prepared as described in example 3 from 2-phenyl-1(3)H-imidazo[4,5-c]pyridine (0.300 g) and 4-tert-butylbenzyl bromide (0.419 g, 1.2 equivalents).

Recrystallized from a mixture of diisopropyl ether (10 mL) and ethyl acetate (23 mL); colorless crystals; mp: 213-215° C.; yield: 49%; $^1$H NMR (200 MHz, DMSO4) δ 9.07 (d, 1H, H4, J=1.6 Hz), 8.39-8.33 (m, 2H, arom. H), 8.17 (dd, 1H, H6, J=6.7, 1.6 Hz), 7.71 (d, 1H, H7, J=6.7 Hz), 7.53-7.35 (m, 7H, arom. H), 5.61 (s, 2H, $CH_2$), 1.24 (s, 9H, $(CH_3)_3$).

Example 22

Preparation of 5-[(4-Bromophenyl)methyl]-2-phenyl-5H-imidazo[4,5-c]pyridine (GPJN-22)

Prepared as described in example 3 from 2-phenyl-1(3)H-imidazo[4,5-c]pyridine (0.300 g) and 4-bromobenzyl bromide (0.461 g, 1.2 equivalents).

Recrystallized from a mixture of diisopropyl ether (10 mL) and ethyl acetate (26 mL); colorless crystals; mp: 212-214° C.; yield: 45%; $^1$H NMR (200 MHz, DMSO-$d_6$) δ 9.09 (br s, 1H, H4), 8.40-8.33 (m, 2H, arom. H), 8.17 (dd, 1H, H6, J=6.8, 1.5 Hz), 7.73 (d, 1H, H7, J=6.8 Hz), 7.64-7.58 (AA'BB', 2H, arom. H), 7.52-7.37 (m, 5H, arom. H), 5.64 (s, 2H, $CH_2$).

Example 23

Preparation of 4-[(2-Phenyl-5H-imidazo[4,5-c]pyridin-5-yl)methyl]-benzonitrile (GPJN-23)

Prepared as described in example 3 from 2-phenyl-1(3)H-imidazo[4,5-c]pyridine (0.300 g) and 4-bromomethyl-benzonitrile (0.362 g, 1.2 equivalents).

Recrystallized twice from a mixture of diisopropyl ether (10 mL) and ethyl acetate (25 mL); pale orange crystals; mp: 93° C. (degr.); yield: 34%; $^1$H NMR (200 MHz, DMSO-$d_6$) δ 9.10 (d, 1H, H4, J=1.5 Hz), 8.40-8.33 (m, 2H, arom. H), 8.18 (dd, 1H, H6, J=6.9, 1.5 Hz), 7.91-7.85 (AA'BB', 2H, arom. H), 7.75 (d, 1H, H7, J=6.9 Hz), 7.61-7.55 (AA'BB', 2H, arom. H), 7.52-7.37 (m, 3H, arom. H), 5.77 (s, 2H, $CH_2$).

Example 24

Preparation of 2-Phenyl-5-[[4-(trifluoromethyl)phenyl]methyl]-5H-imidazo[4,5-c]pyridine (GPJN-24)

Prepared as described in example 3 from 2-phenyl-1(3)H-imidazo[4,5-c]pyridine (0.300 g) and 4-(trifluoromethyl)benzyl bromide (0.441 g, 1.2 equivalents).

Recrystallized from a mixture of diisopropyl ether (10 mL) and ethyl acetate (20 mL); colorless crystals; mp: 230-232° C.; yield: 50%; $^1$H NMR (200 MHz, DMSO-$d_6$) δ 9.12 (d, 1H, H4, J=1.6 Hz), 8.40-8.33 (m, 2H, arom. H), 8.19 (dd, 1H, H6, J=6.9, 1.6 Hz), 7.81-7.73 (m, 3H, arom. H), 7.65-7.59 (AA'BB', 2H, arom. H), 7.53-7.38 (m, 3H, arom. H), 5.78 (s, 2H, $CH_2$).

Example 25

Preparation of 5-[(4-Chlorophenyl)methyl]-2-phenyl-5H-imidazo[4,5-c]pyridine hydrochloride (GPJN-9×HCl)

98 mg of 5-(4-chloro-benzyl)-2-phenyl-5H-imidazo[4,5-c]pyridine (GPJN-9) were dissolved in dry dichloromethane (18 mL) and to this solution was added one equivalent of HCl (1M in diethyl ether). After 2 hours the precipitate was collected by filtration and dried to give 70% of the hydrochloride; colorless crystals; mp:147-148° C. (degr.).

Example 26

Preparation of 5-[(5-Chloro-2-thienyl)methyl]-2-phenyl-5H-imidazo[4,5-c]pyridine (GPJN-25)

Prepared as described in example 3 from 2-phenyl-1(3)H-imidazo[4,5-c]pyridine (0.300 g) and 2-chloro-5-chloromethyl-thiophene (0.308 g, 1.2 equivalents).

Recrystallized from a mixture of diisopropyl ether (20 mL) and ethyl acetate (50 mL); off-white crystals; mp: 215-216° C.; yield: 39%; $^1$H NMR (200 MHz, DMSO-$d_6$) δ 9.07 (d, 1H, H4, J=1.5 Hz), 8.40-8.33 (m, 2H, arom. H), 8.19 (dd, 1H, H6, J=6.8, 1.5 Hz), 7.74 (d, 1H, H7, J=6.8 Hz), 7.55-7.37 (m, 3H, arom. H), 7.28 (d, 1H, thiophene-H, J=3.8 Hz), 7.08 (d, 1H, thiophene-H, J=3.8 Hz), 5.81 (s, 2H, $CH_2$).

Example 27

Preparation of 5-(2-Naphthalenylmethyl)-2-phenyl-5H-imidazo[4,5-c]pyridine (GPJN-26)

Prepared as described in example 3 from 2-phenyl-1(3)H-imidazo[4,5-c]pyridine (0.300 g) and 2-bromomethyl-naphthalene (0.408 g, 1.2 equivalents).

Recrystallized from a mixture of ethyl acetate (20 mL) and ethanol (8 mL); colorless crystals; mp: 267° C.; yield: 36%; $^1$H NMR (200 MHz, DMSO-$d_6$) δ 9.17 (d, 1H, H4, J=1.7 Hz), 8.40-8.33 (m, 2H, arom. H), 8.23 (dd, 1H, H6, J=6.7, 1.7 Hz), 7.99-7.87 (m, 4H, arom. H), 7.74 (d, 1H, H7, J=6.7 Hz), 7.60-7.37 (m, 6H, arom. H), 5.84 (s, 2H, $CH_2$).

Example 28

Preparation of 2-Phenyl-5-(4-phenylbutyl)-5H-imidazo[4,5-c]pyridine (GPJN-27)

Prepared as described in example 3 from 2-phenyl-1(3)H-imidazo[4,5-c]pyridine (0.300 g) and 1-chloro-4-phenylbutane (0.311 g, 1.2 equivalents).

Recrystallized from a mixture of diisopropyl ether (20 mL) and ethyl acetate (11 mL); colorless crystals; mp: 119-120° C.; yield: 53%; $^1$H NMR (200 MHz, DMSO-$d_6$) δ 8.95 (d, 1H, H4, J=1.4 Hz), 8.40-8.33 (m, 2H, arom. H), 8.07 (dd, 1H, H6, J=6.8, 1.4 Hz), 7.70 (d, 1H, H7, J=6.8 Hz), 7.52-7.37 (m, 3H, arom. H), 7.31-7.10 (m, 5H, arom. H), 4.46 (t, 2H, $CH_2$, J=7.1 Hz), 2.62 (t, 2H, $CH_2$, J=7.6 Hz), 2.00-1.85 (m, 2H, $CH_2$), 1.63-1.46 (m, 2H, $CH_2$).

Example 29

Preparation of 5-(3-Methyl-2-butenyl)-2-phenyl-5H-imidazo[4,5-c]pyridine (GPJN-28)

Prepared as described in example 3 from 2-phenyl-1(3)H-imidazo[4,5-c]pyridine (0.300 g) and 4-bromo-2-methylbut-2-ene (0.275 g, 1.2 equivalents).

Recrystallized from a mixture of diisopropyl ether (20 mL) and ethyl acetate (11 mL); off-white crystals; mp: 162-163° C.; yield: 58%; $^1$H NMR (200 MHz, DMSO-$d_6$) δ 8.86 (d, 1H, H4, J=1.7 Hz), 8.40-8.33 (m, 2H, arom. H), 7.99 (dd, 1H, H6, J=6.8, 1.7 Hz), 7.71 (d, 1H, H7, J=6.8 Hz), 7.52-7.37 (m, 3H, arom. H), 5.57-5.47 (m, 1H, =CH), 5.06 (br d, 2H, $CH_2$, J=7.4 Hz), 1.86 (br s, 3H, $CH_3$), 1.77 (br s, 3H, $CH_3$).

Example 30

Preparation of 5-Ethyl-2-phenyl-5H-imidazo[4,5-c]pyridine (GPJN-29)

Prepared as described in example 3 from 2-phenyl-1(3)H-imidazo[4,5-c]pyridine (0.300 g) and ethyl iodide (0.288 g, 1.2 equivalents).

Recrystallized from a mixture of diisopropyl ether (5 mL) and ethyl acetate (12 mL); colorless crystals; mp: 188° C.; yield: 22%; $^1$H NMR (200 MHz, DMSO-$d_4$) δ 8.96 (d, 1H, H4, J=1.6 Hz), 8.40-8.33 (m, 2H, arom. H), 8.09 (dd, 1H, H6, J=6.8, 1.6 Hz), 7.71 (d, 1H, H7, J=6.8 Hz), 7.52-7.36 (m, 3H, arom. H), 4.47 (q, 2H, $CH_2$, J=7.3 Hz), 1.52 (t, 3H, $CH_3$, J=7.3 Hz).

Example 31

Preparation of 5-[2-[bis(1-Methylethyl)amnino]ethyl]-2-phenyl-5H-imidazo[4,5-c]pyridine (GPJN-30)

Prepared as described in example 3 from 2-phenyl-1(3)H-imidazo[4,5-c]pyridine (0.300 g), and 2-(diisopropylamino)ethyl chloride hydrochloride (0.369 g, 1.2 equivalents).

Recrystallized from a mixture of diisopropyl ether (20 mL) and ethyl acetate (10 mL); colorless crystals; mp: 151-152° C.; yield: 57%; $^1$H NMR (200 MHz, DMSO-$d_6$) δ 8.80 (d, 1H, H4, J=1.5 Hz), 8.39-8.33 (m, 2H, arom. H), 7.99 (dd, 1H, H6, J=6.8, 1.5 Hz), 7.67 (d, 1H, H7, J=6.8 Hz), 7.51-7.36 (m, 3H, arom. H), 4.36 (t, 2H, $CH_2$, J=5.4 Hz), 3.04-2.84 (m, 4H, 2×CH and $CH_2$), 0.78 (d, 12H, 4×$CH_3$, J=6.6 Hz).

Example 32

Preparation of 2-Phenyl-5-(4-pyridinylmethyl)-5H-iniidazo[4,5-c]pyridine (GPJN-31)

Prepared as described in example 3 from 2-phenyl-1(3)H-imidazo[4,5-c]pyridine (0.300 g), and 4-chloromethyl-pyridine hydrochloride (0.303 g, 1.2 equivalents).

Recrystallized from a mixture of diisopropyl ether (20 mL) and ethyl acetate (15 mL); colorless crystals (hygroscopic); yield: 25%; $^1$H NMR (200 MHz, DMSO-$d_6$) δ 9.09 (d, 1H, H4, J=1.6 Hz), 8.60-8.57 (m, 2H, pyridine-H2/6), 8.40-8.33 (m, 2H, arom. H), 8.17 (dd, 1H, H6, J=6.8, 1.6 Hz), 7.67 (d, 1H, H7, J=6.8 Hz), 7.52-7.37 (m, 3H, arom. H), 7.31-7.28 (m, 2H, pyridine-H3/5), 5.74 (s, 2H, $CH_2$).

Example 33

Preparation of 2-Phenyl-5-(2-pyridinylmethyl)-5H-imidazo[4,5-c]pyridine (GPJN-34)

Prepared as described in example 3 from 2-phenyl-1(3)H-imidazo[4,5-c]pyridine (0.300 g), and 2-chloromethyl-pyridine hydrochloride (0.303 g, 1.2 equivalents).

Recrystallized from a mixture of diisopropyl ether (20 mL) and ethyl acetate (17 mL); colorless crystals; mp: 102-103° C.; yield: 44%; $^1$H NMR (200 MHz, DMSO-$d_6$) δ 9.02 (d, 1H, H4, J=1.4 Hz), 8.53 (ddd, 1H, pyridine-H6, J=4.7, 1.7, 0.8 Hz), 8.40-8.33 (m, 2H, arom. H), 8.13 (dd, 1H, H6, J=6.8, 1.4 Hz), 7.90-7.82 (m, 1H, pyridine-H4), 7.72 (d, 1H, H7, J=6.8 Hz), 7.52-7.33 (m, 5H, arom. H), 5.79 (s, 2H, $CH_2$).

Example 34

Preparation of 2-Phenyl-5-(3-pyridinylmethyl)-5H-imidazo[4,5-c]pyridine (GPJN-35)

Prepared as described in example 3 from 2-phenyl-1(3)H-imidazo[4,5-c]pyridine (0.300 g), and 3-chloromethyl-pyridine hydrochloride (0.303 g, 1.2 equivalents).

Recrystallized from a mixture of diisopropyl ether (20 mL) and ethyl acetate (41 mL); off-white crystals; mp: 53° C. (degr.); yield: 46%; $^1$H NMR (200 MHz, DMSO-$d_6$) δ 9.14 (d, 1H, H4, J=1.6 Hz), 8.76 (br d, 1H, pyridine-H2), 8.57 (dd, 1H, pyridine-H6, J=4.8, 1.6 Hz), 8.40-8.33 (m, 2H, arom. H), 8.22 (dd, 1H, H6, J=6.8, 1.6 Hz), 7.90-7.84 (m, 1H, pyridine-H4), 7.74 (d, 1H, H7, J=6.8 Hz), 7.52-7.38 (m, 45H, arom. H), 5.71 (s, 2H, $CH_2$).

Example 35

Preparation of 5-([1,1'-Biphenyl]-4-ylmethyl)-2-phenyl-5H-imidazo[4,5-c]pyridine (GPJN-32)

Prepared as described in example 3 from 2-phenyl-1(3)H-imidazo[4,5-c]pyridine (0.300 g) and 4-chloromethyl-biphenyl (0.374 g, 1.2 equivalents).

Recrystallized from a mixture of ethyl acetate (50 mL) and ethanol (1.5 mL); colorless crystals; mp: 247-248° C.; yield: 65%; $^1$H NMR (200 MHz, DMSO-d$_6$) δ 9.14 (d, 1H, H4, J=1.4 Hz), 8.40-8.33 (m, 2H, arom. H), 8.22 (dd, 1H, H6, J=6.8, 1.4 Hz), 7.75 (d, 1H, H7, J=6.8 Hz), 7.72-7.30 (m, 12H, arom. H), 5.71 (s, 2H, CH$_2$).

Example 36

Preparation of 2-Phenyl-5-(1-phenylethyl)-5H-imidazo[4,5-c]pyridine (GPJN-33)

Prepared as described in example 3 from 2-phenyl-1(3)H-imidazo[4,5-c]pyridine (0.300 g) and 1-phenylethyl bromide (0.341 g, 1.2 equivalents).

Recrystallized from a mixture of diisopropyl ether (20 mL) and ethyl acetate (40 mL); colorless crystals; mp: 190-192° C.; yield: 57%; $^1$H NMR (200 MHz, DMSO-d$_6$) δ 9.13 (d, 1H, H4, J=1.6 Hz), 8.39-8.33 (m, 2H, arom. H), 8.19 (dd, 1H, H6, J=6.7, 1.6 Hz), 7.70 (d, 1H, H7, J=6.7 Hz), 7.53-7.31 (m, 8H, arom. H), 6.01 (q, 1H, CH, J=7.0 Hz), 2.04 (d, 3H, CH$_3$, J=7.0 Hz).

Example 37

Preparation of 5-(1-Naphthalenylmethyl)-2-phenyl-5H-imidazo[4,5-c]pyridine (GPJN-36)

Prepared as described in example 3 from 2-phenyl-1(3)H-imidazo[4,5-c]pyridine (0.300 g) and 1-chloromethyl-naphthalene (0.326 g, 1.2 equivalents).

Recrystallized from a mixture of diisopropyl ether (10 mL) and ethyl acetate (45 mL); colorless crystals; mp: 191° C.; yield: 73%; $^1$H NMR (200 MHz, DMSO-d,) δ 9.08 (d, 1H, H4, J=1.5 Hz), 8.39-8.33 (m, 2H, arom. H), 8.23-8.15 (m, 2H, arom. H), 7.75 (d, 1H, H7, J=6.8 Hz), 7.68-7.37 (m, 6H, arom. H), 7.25 (br d, 1H, arom. H, J=6.6 Hz), 6.22 (s, 2H, CH$_2$).

Example 38

Preparation of 5-(Cyclohexylmethyl)-2-phenyl-5H-imidazo[4,5-c]pyridine (GPJN-37)

Prepared as described in example 3 from 2-phenyl-1(3)H-imidazo[4,5-c]pyridine (0.300 g) and cyclohexylmethyl bromide (0.327 g, 1.2 equivalents) with heating at 80° C.

Recrystallized from a mixture of diisopropyl ether (20 mL) and ethyl acetate (14 mL); colorless crystals; mp: 188-189° C.; yield: 36%; $^1$H NMR (200 MHz, DMSO-d$_6$) δ 8.89 (d, 1H, H4, J=1.5 Hz), 8.39-8.33 (m, 2H, arom. H), 8.03 (dd, 1H, H6, J=6.6, 1.5 Hz), 7.69 (d, 1H, H7, J=6.6 Hz), 7.52-7.37 (m, 3H, arom. H), 4.28 (d, 2H, CH$_2$, J=7.4 Hz), 2.02-0.92 (m, 11H, cyclohexyl H).

Example 39

Preparation of 5-(3-Methylbutyl)-2-phenyl-5H-imidazo[4,5-c]pyridine (GPJN-38)

Prepared as described in example 3 from 2-phenyl-1(3)H-imidazo[4,5-c]pyridine (0.300 g) and 1-bromo-3-methylbutane (0.279 g, 1.2 equivalents).

Recrystallized from a mixture of diisopropyl ether (20 mL) and ethyl acetate (17 mL); colorless crystals; mp: 207° C.; yield: 37%; $^1$H NMR (200 MHz, DMSO-d$_6$) δ 8.96 (d, 1H, H4, J=1.5 Hz), 8.40-8.34 (m, 2H, arom. H), 8.09 (dd, 1H, H6, J=6.8, 1.5 Hz), 7.70 (d, 1H, H7, J=6.8 Hz), 7.52-7.37 (m, 3H, arom. H), 4.45 (t, 2H, CH$_2$, J=7.4 Hz), 1.87-1.75 (m, 2H, CH$_2$), 1.53 hept, 1H, CH, J=6.6 Hz), 0.94 (d, 6H, (CH$_3$)$_2$).

Example 40

Preparation of 2-(2,6-Difluorophenyl)-5-[(4-fluorophenyl)methyl]-5H-imidazo[4,5-c]pyridine (GPJN-39)

Prepared as described in example 3 from 2-(2,6-Difluorophenyl)-1(3)H-imidazo[4,5-c]pyridine (0.300 g) and 4-fluorobenzyl chloride (0.225 g, 1.2 equivalents).

Recrystallized from a mixture of diisopropyl ether (10 mL) and ethyl acetate (10 mL); off-white crystals; mp: 104-105° C.; yield: 48%; $^1$H NMR (200 MHz, DMSO-d$_6$) δ 9.26 (d, 1H, H4, J=1.4 Hz), 8.26 (dd, 1H, H6, J=6.8, 1.4 Hz), 7.81 (d, 1H, H7, J=6.8 Hz), 7.61-7.45 (m, 3H, arom. H), 7.30-7.13 (m, 4H, arom. H), 5.69 (s, 2H, CH$_2$).

Example 41

Preparation of 2-(2,6-Difluorophenyl)-5-[(2,4-difluorophenyl)methyl]-5H-imidazo[4,5-c]pyridine (GPJN-40)

Prepared as described in example 3 from 2-(2,6-difluorophenyl)-1(3)H-imidazo[4,5-c]pyridine (0.300 g) and 2,4-difluorobenzyl bromide (0.322 g, 1.2 equivalents).

Recrystallized from a mixture of diisopropyl ether (10 mL) and ethyl acetate (8 mL); off-white crystals; mp: 186-188° C.; yield: 29%; $^1$H NMR (200 MHz, DMSO-d$_6$) δ 9.16 (br s, 1H, H4), 8.18 (dd, 1H, H6, J=6.8, 1.3 Hz), 7.82 (d, 1H, H7, J=6.8 Hz), 7.64-7.11 (m, 6H, arom. H), 5.78 (s, 2H, CH$_2$).

Example 42

Preparation of 2-(2,6-Difluorophenyl)-5-[(2,4,6-trifluorophenyl)methyl]-5H-imidazo[4,5-c]pyridine (GPJN-41)

Prepared as described in example 3 from 2-(2,6-difluorophenyl)-1(3)H-imidazo[4,5-c]pyridine (0.200 g) and 2,4,6-trifluorobenzyl bromide (0.234 g, 1.2 equivalents).

Recrystallized from a mixture of diisopropyl ether (10 mL) and ethyl acetate (8 mL); off-white crystals; mp: 186-187° C.; yield: 26%; $^1$H NMR (200 MHz, DMSO-d$_6$) δ 9.06 (br s, 1H, H4), 8.08 (dd, 1H, H6, J=6.8, 1.6 Hz), 7.81 (d, 1H, H7, J=6.8 Hz), 7.61-7.46 (m, 1H, H4'), 7.42-7.13 (m, 4H, H3'/5'/3"/5"), 5.82 (s, 2H, CH$_2$).

Example 43

Preparation of 5-[(4-Bromophenyl)methyl]-2-ethyl-5H-imidazo[4,5-c]pyridine (GPJN-48)

A mixture of 3,4-diaminopyridine (1.00 g), propionic acid (1 equivalent) and polyphosphoric acid (25 g) was heated at 150° C. for 1 h and then at 190° C. for 2 h with stirring. Then the mixture was cooled to ambient temperature and poured into ice/water. The resulting mixture was made alkaline by addition of 2N NaOH and extracted with ethyl acetate (100 mL) six times. The combined organic phases were dried (Na$_2$SO$_4$) and evaporated to give the crude product, which was recrystallized from ethyl acetate (100 mL) to give 56% of 2-ethyl-1(3)H-imidazo[4,5-c]pyridine as a white powder.

2-Ethyl-1(3)H-imidazo[4,5-c]pyridine (0.245 g) was dissolved in dry DMF (6 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (50 mL) was added, the precipitate was collected by filtration and dried to give the crude product mixture.

Recrystallized from a mixture of diisopropyl ether (10 mL) and ethyl acetate (6 mL); off-white crystals; mp: 149-151° C. (degr.); yield: 47%; $^1$H NMR (200 MHz, DMSO-d$_6$) δ 8.89 (d, 1H, H4, J=1.5 Hz), 8.09 (dd, 1H, H6, J=6.8, 1.5 Hz), 7.62-7.54 (m, 3H, arom. H), 7.39-7.32 (AA'BB', 2H, arom. H), 5.60 (s, 2H, CH$_2$), 2.84 (q, 2H, CH$_2$, J=7.5 Hz), 1.30 (t, 3H, CH$_3$, J=7.5 Hz).

Example 44

Preparation of 5-[(4-Bromophenyl)methyl]-2-(2-chlorophenyl)-5H-imidazo[4,5-c]pyridine (GPJN-54)

A mixture of 3,4-diaminopyridine (1.00 g), 2-chlorobenzoic acid (1 equivalent) and polyphosphoric acid (25 g) was heated at 190° C. for 3 h with stirring. Then the mixture was cooled to ambient temperature and poured into ice water. The resulting mixture was made alkaline by addition of 2N NaOH and the resulting precipitate was collected by filtration and dried. The crude product was recrystallized from a mixture of water (100 mL) and ethanol (17 mL) to give 67% of 2-(2-chlorophenyl)-1(3)H-imidazo[4,5-c]pyridine as an off-white powder.

2-(2-Chlorophenyl)-1(3)H-imidazo[4,5-c]pyridine (0.383 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (20 mL) and ethyl acetate (25 mL); pale orange powder; mp: 190-192° C.; yield: 33%; $^1$H NMR (200 MHz, DMSO-d$_6$) δ 9.21 (d, 1H, H4, J=1.6 Hz), 8.22 (dd, 1H, H6, J=6.8, 1.6 Hz), 8.09-8.02 (m, 1H, arom. H), 7.80 (d, 1H, H7, J=6.8 Hz), 7.65-7.51 (m, 3H, arom. H), 7.46-7.38 (m, 4H, arom. H), 5.67 (s, 2H, CH$_2$).

Example 45

Preparation of 5-[(4-Bromophenyl)methyl]-2-(3-chlorophenyl)-5H-imidazo[4,5-c]pyridine (GPJN-55)

A mixture of 3,4-diaminopyridine (1.00 g), 3-chlorobenzoic acid (1 equivalent) and polyphosphoric acid (25 g) was heated at 190° C. for 3 h with stirring. Then the mixture was cooled to ambient temperature and poured into ice/water. The resulting mixture was made alkaline by addition of 2N NaOH and the resulting precipitate was collected by filtration and dried. The crude product was recrystallized from a mixture of water (100 mL) and ethanol (180 mL) to give 63% of 2-(3-chlorophenyl)-1(3)H-imidazo[4,5-c]pyridine as a white powder.

2-(3-Chlorophenyl)-1(3)H-imidazo[4,5-c]pyridine (0.383 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (20 mL) and ethyl acetate (45 mL); colorless powder; mp: 155-157° C.; yield: 42%; $^1$H NMR (200 MHz, DMSO-d$_6$) δ 9.16 (d, 1H, H4, J=1.5 Hz), 8.35-8.28 (m, 2H, arom. H), 8.20 (dd, 1H, H6, J=6.9, 1.5 Hz), 7.80 (d, 1H, H7, J=6.9 Hz), 7.64-7.38 (m, 6H, arom. H), 5.66 (s, 2H, CH$_2$).

Example 46

Preparation of 5-[(4-Bromophenyl)methyl]-2-(4-chlorophenyl)-5H-imidazo[4,5-c]pyridine (GPJN-56)

A mixture of 3,4-diaminopyridine (1.00 g), 4-chlorobenzoic acid (1 equivalent) and polyphosphoric acid (25 g) was heated at 190° C. for 3 h with stirring. Then the mixture was cooled to ambient temperature and poured into ice/water. The resulting mixture was made alkaline by addition of 2N NaOH and the resulting precipitate was collected by filtration and dried. The crude product was recrystallized from a mixture of water (100 mL) and ethanol (110 mL) to give 47% of 2-(4-chlorophenyl)-1(3)H-imidazo[4,5-c]pyridine as a colorless powder.

2-(4-Chlorophenyl)-1(3)H-imidazo[4,5-c]pyridine (0.383 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (20 mL) and ethyl acetate (25 mL); off-white powder; mp: 214-215° C.; yield: 67%; $^1$H NMR (200 MHz, DMSO-$_6$) δ 9.13 (d, 1H, H4, J=1.6 Hz), 8.39-8.32 (AA'BB', 2H, arom. H), 8.18 (dd, 1H, H6, J=6.9, 1.6 Hz), 7.64-7.58 (AA'BB', 2H, arom. H), 7.56-7.49 (AA'BB', 2H, arom. H), 7.44-7.38 (AA'BB', 2H, arom. H), 5.65 (s, 2H, CH$_2$).

Example 47

Preparation of 5-[(4-Bromophenyl)methyl]-2-(2-pyridinyl)-5H-imidazo[4,5-c]pyridine (GPJN-58)

A mixture of 3,4-diaminopyridine (1.00 g), picolinic acid (1 equivalent) and polyphosphoric acid (25 g) was heated at 190° C. for 3 h with stirring. Then the mixture was cooled to ambient temperature and poured into ice/water. The resulting mixture was made alkaline by addition of solid NaOH and the resulting precipitate was collected by filtration and dried. The crude product was recrystallized from a mixture of water (50 mL) and ethanol (7 mL) to give 55% of 2-(2-pyridyl)-1(3)H-imidazo[4,5-c]pyridine as an off-white powder.

2-(2-Pyridyl)-1(3)H-imidazo[4,5-c]pyridine (0.327 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of ethyl acetate (75 mL) and ethanol (10 mL); pale brown crystals; mp: 256-258° C.; yield: 43%; $^1$H NMR (200 MHz, DMSO-d,) δ 9.21 (d, 1H, H4, J=1.4 Hz), 8.68 (ddd, 1H, pyridine-H6), 8.40 (ddd, 1H, pyridine-H), 8.20 (dd, 1H, H6, J=6.8, 1.4 Hz), 7.89 (ddd, H, pyridine-H), 7.79 (d, 1H, H7, J=6.8 Hz), 7.65-7.58 (AA'BB', 2H, arom. H), 7.45-7.37 (m, 3H, arom. H), 5.68 (s, 2H, CH$_2$).

Example 48

Preparation of 5-[(4-Bromophenyl)methyl]-2-(3-pyridinyl)-5H-imidazo[4,5-c]pyridine (GPJN-57)

A mixture of 3,4-diaminopyridine (1.00 g), nicotinic acid (1 equivalent) and polyphosphoric acid (25 g) was heated at 190° C. for 3 h with stirring. Then the mixture was cooled to ambient temperature and poured into ice/water. The resulting mixture was made alkaline by addition of solid NaOH and the resulting solution was evaporated. The residue was extracted twice with ethyl acetate (2×200 mL) and the combined organic phases were dried (Na$_2$SO$_4$) and evaporated. The crude product, thus obtained, was recrystallized from a mixture of ethyl acetate (50 mL) and ethanol (13 mL) to give 34% of 2-(3-pyridyl)-1(3)H-imidazo[4,5-c]pyridine as an off-white powder.

2-(3-Pyridyl)-1(3)H-imidazo[4,5-c]pyridine (0.327 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (10 mL), ethyl acetate (75 mL) and ethanol (20 mL); pale yellow powder; mp: 270-272° C.; yield: 40%; $^1$H NMR (200 MHz, DMSO-d$_6$) δ 9.49 (m, 1H, pyridine-H2), 9.18 (d, 1H, H4, J=1.5 Hz), 8.65-8.60 (m, 2H, arom. H), 8.21 (dd, 1H, H6, J=6.8, 1.5 Hz), 7.79 (d, 1H, H7, J=6.8 Hz), 7.65-7.58 (AA'BB', 2H, arom. H), 7.54-7.38 (m, 3H, arom. H), 5.66 (s, 2H, CH$_2$).

Example 49

Preparation of 5-[(4-Bromophenyl)methyl]-2-(4-pyridinyl)-5H-imidazo[4,5-c]pyridine (GPJN-49)

A mixture of 3,4-diaminopyridine (1.00 g), isonicotinic acid (1 equivalent) and polyphosphoric acid (25 g) was heated at 190° C. for 3 h with stirring. Then the mixture was cooled to ambient temperature and poured into ice/water. The resulting mixture was made alkaline by addition of solid NaOH and the resulting precipitate was collected by filtration and dried. The crude product was recrystallized from water (55 mL) to give 84% of 2-(4-pyridyl)-1(3)H-imidazo[4,5-c]pyridine as a pale orange powder.

2-(4-Pyridyl)-1(3)H-imidazo[4,5-c]pyridine (0.327 g) was dissolved in dry DMF (11 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (10 mL) and ethyl acetate (75 mL); pale brown powder; mp: 190-194° C. (degr.); yield: 40%; $^1$H NMR (200 MHz, DMSO-d$_6$) δ 9.25 (d, 1H, H4, J=1.4 Hz), 8.70-8.67 (m, 2H, pyridine-H2/6), 8.25-8.20 (m, 3H, arom. H), 7.83 (d, 1H, H7, J=6.8 Hz), 7.64-7.58 (AA'BB', 2H, arom. H), 7.45-7.39 (AA'BB', 2H, arom. H), 5.68 (s, 2H, CH$_2$).

Example 50

Preparation of 5-[(4-Bromophenyl)methyl]-2-(2-thienyl)-5H-imidazo[4,5-c]pyridine (GPJN-53)

A mixture of 3,4-diaminopyridine (1.00 g), thiophene-2-carboxylic acid (1 equivalent) and polyphosphoric acid (25 g) was heated at 190° C. for 3 h with stirring. Then the mixture was cooled to ambient temperature and poured into ice/water. The resulting mixture was neutralized by addition of solid NaOH and the resulting precipitate was collected by filtration and dried. The crude product was recrystallized from a mixture of water (50 mL) and ethanol (25 ml) to give 30% of 2-(2-thienyl)-1(3)H-imidazo[4,5-c]pyridine as pale yellow crystals.

2-(2-Thienyl)-1(3)H-imidazo[4,5-c]pyridine (0.335 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from ethyl acetate (70 mL); pale yellow powder; mp: 230-231° C.; yield: 24%; $^1$H NMR (200 MHz, DMSO-d$_6$) δ 9.01 (d, 1H, H4, J=1.5 Hz), 8.16 (dd, 1H, H6, J=6.8, 1.5 Hz), 7.81 (dd, 1H, thiophene-H, J=3.6, 1.4 Hz), 7.67 (d, 1H, H7, J=6.8 Hz), 7.64-7.57 (m, 3H, arom. H), 7.43-7.37 (AA'BB', 2H, arom. H), 5.63 (s, 2H, CH$_2$).

Example 51

Preparation of 2-Benzyl-5-[(4-bromophenyl)methyl]-5H-imidazo[4,5-c]pyridine (GPJN-67)

A mixture of 3,4-diaminopyridine (1.00 g), phenylacetic acid (1 equivalent) and polyphosphoric acid (25 g) was heated at 120° C. for 1 h and then at 150° C. for 12 h with stirring. Then the mixture was cooled to ambient temperature and poured into ice/water. The resulting mixture was made alkaline by addition of solid NaOH and the resulting precipitate was collected by filtration and dried. The crude product was recrystallized from a mixture of diisopropyl ether (20 mL) and ethyl acetate (76 mL) to give 57% of 2-benzyl-1(3)H-imidazo[4,5-c]pyridine as a colorless powder.

2-Benzyl-1(3)H-imidazo[4,5-c]pyridine (0.500 g) was dissolved in dry DMF (5 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of ethyl acetate (50 mL) and ethanol (6.5 mL); pale yellow powder; mp: 232-233° C.; yield: 46%; $^1$H NMR (200 z, DMSO-d$_6$) δ 8.94 (d, 1H, H4, J=1.4 Hz), 8.10 (dd, 1H, H6, J=6.8, 1.4 Hz), 7.61-7.39 (m, 3H, arom. H), 7.38-7.10 (m, 7H, arom. H), 5.65 (s, 2H, 5-CH$_2$), 4.17 (s, 2H, 2-CH$_2$).

Example 52

Preparation of 5-[(4-Bromophenyl)methyl]-2-(1-naphthalenyl)-5H-imidazo[4,5-c]pyridine (GPJN-62)

A mixture of 3,4-diaminopyridine (1.00 g), 1-naphthoic acid (1 equivalent) and polyphosphoric acid (25 g) was heated at 190° C. for 3 hours with stirring. Then the mixture was cooled to ambient temperature and poured into ice/water. The resulting mixture was made alkaline by addition of solid NaOH and the resulting precipitate was collected by filtration and dried. The crude product was recrystallized from a mixture of water (100 mL) and ethanol (130 mL) to give 47% of 2-(1-naphthalenyl)-I(3)H-imidazo[4,5-c]pyridine as an off-white powder.

2-(1-Naphthalenyl)-1(3)H-imidazo[4,5-c]pyridine (0.409 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (10 mL), ethyl acetate (50 mL) and ethanol (5 mL); pale yellow powder; mp: 210-213° C. (degr.); yield: 22%; $^1$H NMR (200 MHz, DMSO-d$_6$) δ 9.73 (m, 1H, arom. H), 9.22 (d, 1H, H4, J=1.6 Hz), 8.52 (dd, 1H, arom. H, J=7.2, 1.4 Hz), 8.23 (dd, 1H, H6, J=6.8, 1.6 Hz), 8.03-7.95 (m, 2H, arom. H), 7.83 (d, 1H, H7, J=6.8 Hz), 7.65-7.41 (m, 7H, arom. H), 5.68 (s, 2H, CH$_2$).

Example 53

Preparation of 5-[(4-Bromophenyl)methyl]-2-(2-naphthalenyl)-5H-imidazo[4,5-c]pyridine (GPJN-63)

A mixture of 3,4-diaminopyridine (1.00 g), 2-naphthoic acid (1 equivalent) and polyphosphoric acid (25 g) was heated at 190° C. for 3 hours with stirring. Then the mixture was cooled to ambient temperature and poured into ice/water. The resulting mixture was made alkaline by addition of solid NaOH and the resulting precipitate was collected by filtration and dried. The crude product was recrystallized from a mixture of water (100 mL) and ethanol (400 mL) to give 28% of 2-(2-naphthalenyl)-1(3)H-imidazo[4,5-c]pyridine as an off-white powder.

2-(2-Naphthalenyl)-1(3)H-imidazo[4,5-c]pyridine (0.409 g) was dissolved in dry DMF (10 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (20 mL) and ethyl acetate (60 mL); pale orange powder; mp: 133-138° C. (degr.); yield: 52%; $^1$H NMR (200 MHz, DMSO-d$_6$) δ 9.13 (d, 1H, H4, J=1.4 Hz), 8.93 (br s, 1H, arom. H), 8.51 (dd, 1H, arom. H, J=8.6, 1.6 Hz), 8.19 (dd, 1H, H6, J=6.7, 1.4 Hz), 8.10-7.90 (m, 3H, arom. H), 7.76 (d, 1H, H7, J=6.7 Hz), 7.65-7.50 (m, 4H, arom. H), 7.52-7.39 (AA'BB', 2H, arom. H), 5.67 (s, 2H, CH$_2$).

Example 54

Preparation of 5-[(4-Bromophenyl)methyl]-2-(2-fluorophenyl)-5H-imidazo[4,5-c]pyridine (GPJN-52)

A mixture of 3,4-diaminopyridine (1.00 g), 2-fluorobenzoic acid (1 equivalent) and polyphosphoric acid (25 g) was heated at 190° C. for 3 h with stirring. Then the mixture was cooled to ambient temperature and poured into ice/water. The resulting mixture was made alkaline by addition of 2N NaOH and the resulting precipitate was collected by filtration and dried. The crude product was recrystallized from a mixture of water (100 mL) and ethanol (20 mL) to give 87% of 2-(2-fluorophenyl)-1(3)H-imidazo[4,5-c]pyridine as an off-white powder.

2-(2-Fluorophenyl)-1(3)H-imidazo[4,5-c]pyridine (0.355 g) was dissolved in dry DMF (7 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (80 mL) was added, the precipitate was collected by filtration and dried to give the crude product.

Recrystallized from a mixture of diisopropyl ether (10 mL) and ethyl acetate (25 mL); off-white powder; mp: 156° C.; yield: 53%; $^1$H NMR (200 MHz, DMSO-d$_6$) δ 9.18 (d, 1H, H4, J=1.6 Hz), 8.35-8.26 (m, 1H, arom. H), 8.20 (dd, 1H, H6, J=6.8, 1.6 Hz), 7.78 (d, 1H, H7, J=6.8 Hz), 7.64-7.58 (AA'BB', 2H, arom. H), 7.52-7.24 (m, 5H, arom. H), 5.66 (s, 2H, CH$_2$).

Example 55

Preparation of 5-[(4-Bromophenyl)methyl]-2-[(1E)-2-phenylethenyl]-5H-imidazo[4,5-c]pyridine (GPJN-81)

A mixture of 3,4-diaminopyridine (0.500 g) and cinnamic acid (2.036 g, 3 equivalents) was heated at 160° C. for 24 h with stirring. The resulting mixture was cooled to ambient temperature and washed with diisopropyl ether. The remaining solid was dissolved in ethyl acetate and the resulting solution was extracted with 2N aqueous sodium hydroxide solution. The organic phase was dried and evaporated to give 0.580 g of a pale brown solid. Recrystallization from a mixture of diisopropyl ether (20 mL) and ethyl acetate (31 mL) gave 30% of 2-[(1E)-2-phenylethenyl]-1(3)H-imidazo[4,5-c]pyridine as an off-white powder.

2-[(1E)-2-Phenylethenyl]-1(3)H-imidazo[4,5-c]pyridine (0.250 g) was dissolved in dry DMF (3 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (30 mL) was added, the precipitate was collected by filtration and dried to give the crude product.

Recrystallized from a mixture of diisopropyl ether (10 mL) and ethyl acetate (35 mL); pale brown powder; mp: 212-214° C. (degr.); yield: 27%; $^1$H NMR (200 MHz, DMSO-d$_6$) δ 9.02 (d, 1H, H4, J=1.6 Hz), 8.15 (dd, 1H, H6, J=6.6, 1.6 Hz), 7.83 (d, 1H, =CH, J=16.2 Hz), 7.72-7.59 (m, 5H, arom. H), 7.48-7.30 (m, 6H), 5.63 (s, 2H, CH$_2$).

Example 56

Preparation of 5-[(4-Bromophenyl)methyl]-2-[(phenylthio)methyl]-5H-imidazo[4,5-c]pyridine (GPJN-83)

A mixture of 3,4-diaminopyridine (0.500 g) and phenylthioacetic acid (2.312 g, 3 equivalents) was heated at 160° C. for 6 h with stirring. The resulting mixture was cooled to ambient temperature and washed with diisopropyl ether. The remaining solid was dissolved in ethyl acetate and the resulting solution was extracted with 2N aqueous sodium hydroxide solution. The organic phase was dried and evaporated to give 0.520 g of a pale brown solid. Recrystallization from a mixture of diisopropyl ether (20 mL) and ethyl acetate (16 mL) gave 32% of 2-[(phenylthio)methyl]-1(3)H-imidazo[4,5-c]pyridine as an off-white powder.

2-[(Phenylthio)methyl]-1(3)H-imidazo[4,5-c]pyridine (0.300 g) was dissolved in dry DMF (5 mL) and the resulting solution was cooled to 0° C. Aqueous 33% sodium hydroxide (1.5 equivalents) was added and the mixture was stirred for 15 min. Then 4-bromobenzyl bromide (1.2 equivalents) was added portionwise and the resulting mixture was stirred for 24 h at room temperature. Finally, water (50 mL) was added, the precipitate was collected by filtration and dried to givee the crude product.

Recrystallized from a mixture of diisopropyl ether (10 mL) and ethyl acetate (30 mL); pale brown powder; mp: 168-170° C. (degr.); yield: 32%; $^1$H NMR (200 MHz, DMSO-d$_6$) δ 9.05 (d, 1H, H4, J=1.6 Hz), 8.16 (dd, 1H, H6, J=6.8, 1.6 Hz), 7.67 (d, 1H, H7, J=6.8 Hz), 7.63-7.56 (AA'BB', 2H, arom. H), 7.48-7.14 (m, 6H, arom. H), 7.18-7.09 (m, 1H, arom. H), 5.63 (s, 2H, N—CH$_2$), 4.41 (s, 2H, S—CH$_2$).

Example 57

Preparation of 5-([1,1'-Biphenyl]-4-ylmethyl)-2-(2-fluorophenyl)-5H-imidazo[4,5-c]pyridine (GPJN-110)

Prepared as described in example 3 from 2-(2-fluorophenyl)-1(3)H-imidazo[4,5-c]pyridine (0.263 g) and 4-chloromethyl-biphenyl (0.300 g, 1.2 equivalents).

Recrystallized from ethyl acetate (55 mL); colorless needles; mp: 216° C.; yield: 35%; $^1$H NMR (200 MHz, DMSO-d$_6$) δ 9.23 (d, 1H, H4, J=1.6 Hz), 8.36-8.23 (m, 2H, arom. H), 7.80 (d, 1H, H7, J=6.6 Hz), 7.73-7.24 (m, 12H, arom. H), 5.73 (s, 2H, CH$_2$).

Example 58

Preparation of 5-[(4-Chlorophenyl)methyl]-2-(2-fluorophenyl)-5H-imidazo[4,5-c]pyridine (GPJN-112)

Prepared as described in example 3 from 2-(2-fluorophenyl)-1(3)H-imidazo[4,5-c]pyridine (0.300 g) and 4-chlorobenzyl chloride (0.272 g, 1.2 equivalents).

Recrystallized from a mixture of diisopropyl ether (10 mL) and ethyl acetate (25 mL); off-white crystals; mp: 167° C.; yield: 53%; $^1$H NMR (200 MHz, DMSO-d$_6$) δ 9.18 (d, 1H, H4, J=1.4 Hz), 8.35-8.26 (m, 1H, arom. H), 8.21 (dd, 1H, H6, J=6.6, 1.4 Hz), 7.78 (d, 1H, H7, J=6.6 Hz), 7.53-7.24 (m, 7H, arom. H), 5.68 (s, 2H, CH$_2$).

Example 59

Preparation of 2-(2-Fluorophenyl)-5-[(4-iodophenyl)methyl]-5H-imidazo[4,5-c]pyridine (GPJN-113)

Prepared as described in example 3 from 2-(2-fluorophenyl)-1(3)H-imidazo[4,5-c]pyridine (0.300 g) and 4-iodobenzyl bromide (0.501 g, 1.2 equivalents).

Recrystallized from a mixture of diisopropyl ether (10 mL) and ethyl acetate (25 mL); off-white crystals; mp: 181° C.; yield: 75%; $^1$H NMR (200 MHz, DMSO-d$_6$) δ 9.17 (d, 1H, H4, J=1.6 Hz), 8.35-8.26 (m, 1H, arom. H), 8.19 (dd, 1H, H6, J=6.6, 1.6 Hz), 7.81-7.74 (m, 3H, arom. H), 7.52-7.23 (m, 5H, arom. H), 5.64 (s, 2H, CH$_2$).

Example 60

Preparation of 5-[[4-(1,1-Dimethylethyl)phenyl]methyl]-2-(2-fluorophenyl)-5H-imidazo[4,5-c]pyridine (GPJN-114)

Prepared as described in example 3 from 2-(2-fluorophenyl)-1(3)H-imidazo[4,5-c]pyridine (0.300 g) and 4-tert-butylbenzyl bromide (0.384 g, 1.2 equivalents).

Recrystallized from a mixture of diisopropyl ether (10 mL) and ethyl acetate (58 mL); colorless crystals; mp: 235° C.; yield: 59%; $^1$H NMR (200 MHz, DMSO-d$_6$) δ 9.17 (d, 1H, H4, J=1.6 Hz), 8.35-8.26 (m, 1H, arom. H), 8.21 (dd, 1H, H6, J=6.8, 1.6 Hz), 7.77 (d, 1H, H7, J=6.8 Hz), 7.52-7.24 (m, 7H, arom. H), 5.64 (s, 2H, CH$_2$), 1.25 (s, 9H, (CH$_3$)$_3$).

Example 61

Preparation of 5-([1,1'-Biphenyl]-4-ylmethyl)-2-(1-naphthalenyl)-5H-imidazo[4,5-c]pyridine (GPJN-115)

Prepared as described in example 3 from 2-(1-naphthalenyl)-1(3)H-imidazo[4,5-c]pyridine (0.303 g) and 4-chloromethyl-biphenyl (0.300 g, 1.2 equivalents).

Recrystallized from a mixture of diisopropyl ether (5 mL) and ethyl acetate (43 mL); off-white powder; mp: 216° C.; yield: 23%; $^1$H NMR (200 MHz, DMSO-$d_6$) δ 9.77-9.71 (m, 1H, arom. H), 9.28 (d, 1H, H4, J=1.6 Hz), 8.53 (dd, 1H, arom. H, J=7.2, 1.2 Hz), 8.29 (dd, 1H, H6, J=6.6, 1.6 Hz), 8.02-7.32 (m, 15H, arom. H), 5.75 (s, 2H, $CH_2$).

Example 62

Preparation of 5-[(4-Bromophenyl)methyl]-2-(phenoxymethyl)-5H-imidazo[4,5-c]pyridine (GPJN-82)

Prepared in analogy to example 56 by using phenoxyacetic acid instead of phenylthioacetic acid.

Recrystallized from a mixture of diisopropyl ether (10 mL) and ethyl acetate (30 mL); off-white powder, mp: 168-169° C.; yield: 31%; $^1$H NMR (200 MHz, DMSO-$d_6$) δ 9.13 (d, 1H, H4, J=1.5 Hz), 8.19 (dd, 1H, H6, J=6.8, 1.5 Hz), 7.72 (d, 1H, H7, J=6.8 Hz), 7.63-7.56 (AA'BB', 2H, arom. H), 7.42-7.35 (AA'BB', 2H, arom. H), 7.31-6.86 (m, 5H, arom. H), 5.65 (s, 2H, N—$CH_2$), 5.28 (s, 2H, O—$CH_2$).

Example 63

Preparation of 5-[(4-Bromophenyl)methyl]-4-chloro-2-phenyl-5H-imidazo[4,5-c]pyridine (GPJN-96)

Prepared as described in example 3 from 4-chloro-2-phenyl-1(3)H-imidazo[4,5-c]pyridine (0.425 g) and 4-bromobenzyl bromide (0.270 g, 1.2 equivalents).

Purified by column chromatography (dichloromethane:methanol=20:1); colorless crystals; mp: 245-250° C.; yield: 11%; $^1$H NMR (200 MHz, DMSO-$d_6$) δ 8.44 (d, 1H, H6, J=6.7 Hz), 8.40-8.33 (m, 2H, arom. H), 7.83 (d, 1H, H7, J=6.7 Hz), 7.63-7.57 (AA'BB', 2H, arom. H), 7.55-7.43 (m, 3H, arom. H), 7.21-7.15 (AA'BB', 2H, arom. H), 5.88 (s, 2H, $CH_2$).

Example 64

Preparation of 5-[(4-Bromophenyl)methyl]-4-hydroxy-2-phenyl-5H-imidazo[4,5-c]pyridine (GPJN-95) (=5-[(4-Bromophenyl)methyl]-1,4-dihydro-4-oxo-2-phenyl-5H-imidazo[4,5-c]pyridine)

5-[(4-Bromophenyl)methyl]-4-chloro-2-phenyl-5H-imidazo[4,5-c]pyridine (GPJN-96) (see example 63) (0.200 g) was dissolved in DMF (5 mL) and 2N aqueous sodium hydroxide solution (10 mL) was added. The resulting mixture was heated at 60° C. for 24 h. Then water (50 mL) was added and the resulting mixture was neutralized by addition of 2N HCl. The precipitate was collected by filtration to give the crude product.

Recrystallized from a mixture of diisopropyl ether (25 mL) and ethyl acetate (23 mL); colorless powder; mp: 268-270° C.; yield: 81%; $^1$H NMR (200 MHz, DMSO-$d_6$) δ 8.17-8.13 (m, 2H, arom. H), 7.59-7.44 (m, 6H, arom. H), 7.28-7.23 (AA'BB', 2H, arom. H), 6.67 (br d, 2H, H7, J=6.8 Hz), 5.21 (s, 2H, $CH_2$).

Example 65

Preparation of 5-[(4-Bromophenyl)methyl]-7-chloro-2-phenyl-5H-imidazo[4,5-c]pyridine (GPJN-103)

Prepared as described in example 3 from 7-chloro-2-phenyl-1(3)H-imidazo[4,5c]pyridine (0.300 g) (prepared as described in example 2 from 5-chloro-3,4-diaminopyridine and benzoic acid) and 4-bromobenzyl bromide (0.240 g, 1.2 equivalents).

Recrystallized from a mixture of diisopropyl ether (10 mL), ethyl acetate (35 mL) and ethanol (2 mL); off-white crystals; mp: 215-217° C.; yield: 48%; $^1$H NMR (200 MHz, DMSO-$d_6$) δ 9.17 (d, 1H, H4, J=1.2 Hz), 8.56 (d, 1H, H6, J=1.2 Hz), 8.40-8.33 (m, 2H, arom. H), 7.65-7.59 (AA'BB', 2H, arom. H), 7.54-7.44 (m, 5H, arom. H), 5.65 (s, 2H, $CH_2$).

In analogy to the above examples, the following additional compounds were prepared:

5-[(2-Bromophenyl)methyl]-2-phenyl-5H-imidazo[4,5-c]pyridine (GPJN-42)
5-[(3-Bromophenyl)methyl]-2-phenyl-5H-imidazo[4,5-c]pyridine (GPJN-43)
2-[(2-Phenyl-5H-imidazo[4,5-c]pyridin-5-yl)methyl]-benzonitrile (GPJN-44)
3-[(2-Phenyl-5H-imidazo[4,5-c]pyridin-5-yl)methyl]-benzonitrile (GPJN-45)
2-Phenyl-5-[[2-(trifluoromethyl)phenyl]methyl]-5H-imidazo[4,5-c]pyridine (GPJN-46)
2-Phenyl-5-[[3-(trifluoromethyl)phenyl]methyl]-5H-imidazo[4,5-c]pyridine (GPJN-47)
5-[(4-Bromophenyl)methyl]-2-(3-fluorophenyl)-5H-imidazo[4,5-c]pyridine (GPJN-50)
5-[(4-Bromophenyl)methyl]-2-(3-fluorophenyl)-SH-imidazo[4,5-c]pyridine (GPJN-51)
5-[(4-Bromophenyl)methyl]-2-(2-methylphenyl)-5H-imidazo[4,5-c]pyridine (GPJN-59)
5-[(4-Bromophenyl)methyl]-2-(3-methylphenyl)-5H-imidazo[4,5-c]pyridine (GPJN-60)
5-[(4-Bromophenyl)methyl]-2-(4-methylphenyl)-5H-imidazo[4,5-c]pyridine (GPJN-61)
5-[(4-Bromophenyl)methyl]-2-(3-methoxyphenyl)-5H-imidazo[4,5-c]pyridine (GPJN-64)
2-(3-Bromophenyl)-5-[(4-bromophenyl)methyl]-5H-imidazo[4,5-c]pyridine (GPJN-65)
N,N-Dimethyl-3-[5-[(4-Bromophenyl)methyl]-5H-imidazo[4,5-c]pyridin-2-yl]-benzenamine (GPJN-66)
5-[(4-Iodophenyl)methyl]-2-phenyl-5H-imidazo[4,5-c]pyridine (GPJN-68)
5-[(4-Bromophenyl)methyl]-2-(3-iodophenyl)-5H-imidazo[4,5-c]pyridine (GPJN-69)
5-[(4-Bromophenyl)methyl]-2-(2-bromophenyl)-5H-imidazo[4,5-c]pyridine (GPJN-70)
5-(2-Ethylbutyl)-2-phenyl-5H-imidazo[4,5-c]pyridine (GPJN-72)
5-(2-Phenoxyethyl)-2-phenyl-5H-imidazo[4,5-c]pyridine (GPJN-73)
5-[(3,4-Dichlorophenyl)methyl]-2-phenyl-5H-imidazo[4,5-c]pyridine (GPJN-74)
2-Phenyl-5-(3-phenyl-2-propenyl)-5H-imidazo[4,5-c]pyridine (GPJN-75)
5-[(4-Bromophenyl)methyl]-2-(2-phenylethyl)-5H-imidazo[4,5-c]pyridine (GPJN-76)
5-[(4-Bromophenyl)methyl]-2-(3-phenylpropyl)-5H-imidazo[4,5-c]pyridine (GPJN-77)
5-[(4-Bromophenyl)methyl]-2-(3,5-dibromophenyl)-5H-imidazo[4,5-c]pyridine (GPJN-78)

2-(3-Bromophenyl)-5-[(4-iodophenyl)methyl]-5H-imidazo[4,5-c]pyridine (GPJN-79)
2-(3-Bromophenyl)-5-[(4-chlorophenyl)methyl]-5H-imidazo[4,5-c]pyridine (GPJN-80)
2-(3-Bromophenyl)-5-[(3,4-dichlorophenyl)methyl]-5H-imidazo[4,5-c]pyridine (GPJN-84)
5-[(4-Bromophenyl)methyl]-2-(4-phenylbutyl)-5H-imidazo[4,5-c]pyridine (GPJN-85)
5-[(4-Bromophenyl)methyl]-2-(5-bromo-2-thienyl)-5H-imidazo[4,5-c]pyridine (GPJN-86)
5-[(4-Bromophenyl)methyl]-2-[3-(trifluoromethyl)phenyl]-5H-imidazo[4,5-c]pyridine (GPJN-87)
2-Phenyl-5-[[4-(trifluoromethoxy)phenyl]methyl]-5H-imidazo[4,5-c]pyridine (GPJN-88)
5-[(4-Bromophenyl)methyl]-2-(2,3,6-trifluorophenyl)-5H-imidazo[4,5-c]pyridine (GPJN-89)
5-[(4-Bromophenyl)methyl]-2-(2,5-difluorophenyl)-5H-imidazo[4,5-c]pyridine (GPJN-90)
7-Bromo-5-[(4-bromophenyl)methyl]-2-phenyl-5H-imidazo[4,5-c]pyridine (GPJN-91)
4-[2-Phenyl-5H-imidazo[4,5-c]pyridin-5-yl]-benzoic acid (GPJN-94)
2-Benzyl-5-(2-phenylethyl)-5H-imidazo[4,5-c]pyridine (GPJN-98)
2-(3-Bromophenyl)-5-(3-phenylpropyl)-5H-imidazo[4,5-c]pyridine (GPJN-99)
2-(3-Bromophenyl)-5-(2-phenoxyethyl)-5H-imidazo[4,5-c]pyridine (GPJN-100)
5-[(4-Bromophenyl)methyl]-7-methyl-2-phenyl-5H-imidazo[4,5-c]pyridine (GPJN-104)
5-Benzyl-2-(2-fluorophenyl)-5H-imidazo[4,5-c]pyridine (GPJN-105)
2-(2-Fluorophenyl)-5-[(2-methylphenyl)methyl]-5H-imidazo[4,5-c]pyridine (GPJN-106)
2-(2-Fluorophenyl)-5-[(3-methylphenyl)methyl]-5H-imidazo[4,5-c]pyridine (GPJN-107)
2-(2-Fluorophenyl)-5-[(4-methylphenyl)methyl]-5H-imidazo[4,5-c]pyridine (GPJN-108)
5-([1,1'-Biphenyl]-4-ylmethyl)-2-[(phenylthio)methyl]-5H-imidazo[4,5-c]pyridine (GPJN-111)
5-[(3,4-Dichlorophenyl)methyl]-2-(2,6-difluorophenyl)-5H-imidazo[4,5-c]pyridine (GPC-10)
5-[(2,4-Difluorophenyl)methyl]-2-(3-fluorophenyl)-5H-imidazo[4,5-c]pyridine (GPC-11)
5-[(2,4-Difluorophenyl)methyl]-2-(2,3,6-trifluorophenyl)-5H-imidazo[4,5-c]pyridine (GPC-12)
2-(2,5-Difluorophenyl)-5-[(2,4-difluorophenyl)methyl]-5H-imidazo[4,5-c]pyridine (GPC-13)

Part B

Methodology for Determination of Antiviral and Cytostatic Activity

Cells and Viruses

Madin-Darbey Bovine Kidney (MDBK) cells were maintained in Dulbecco's modified Eagle medium (DMEM) supplemented with BVDV-free 5% fetal calf serum (DMEME-FCS) at 37° C. in a humidified, 5% $CO_2$ atmosphere. BVDV-1 (strain PE515) was used to assess the antiviral activity in MDBK cells. Vero cells were maintained in the same way as MDBK cells. Vero cells were infected with Coxsackie B3 virus (strain Nancy).

Determination of Cytostatic Effect on MDBK Cells

The effect of the drugs on exponentially growing MDBK cells was assessed as follows. Cells were seeded at a density of 5000 cell/well in 96 well plates in MEM medium (Gibco) supplemented with 10% fetal calf serum, 2 mM L-glutamine (Life Technologies) and bicarbonate (Life Technologies). Cells were cultured for 24 hr after which serial dilutions of the test compounds were added. Cultures were then again further incubated for 3 days after which the effect on cell growth was quantified by means of the MTS method (Promega). The concentration that results in 50% inhibition of cell growth is defined as the 50% cytostatic concentration ($CC_{50}$)

Anti-BVDV assay

Ninety-six-well cell culture plates were seeded with MDBK cells in DMEM-FCS so that cells reached 24 hr later confluency. Then medium was removed and serial 5-fold dilutions of the test compounds were added in a total volume of 100 ul, after which the virus inoculum (100 ul) was added to each well. The virus inoculum used resulted in a greater than 90% destruction of the cell monolayer after 5 days incubation at 37° C. Uninfected cells and cells receiving virus without compound were included in each assay plate. After 5 days, medium was removed and 90 µl of DMEM-FCS and 10 ul of MTS/PMS solution (Promega) was added to each well. Following a 2 hr incubation period at 37° C. the optical density of the wells was read at 498 nm in a microplate reader. The 50% effective concentration ($EC_{50}$) value was defined as the concentration of compound that protects 50% of the cell monolayer from virus-induced cytopathic effect.

Anti-HCV Assay/Replicon Assay

Huh-5-2 cells [a cell line with a persistent HCV replicon I389luc-ubi-neo/NS3-3'/5.1; replicon with firefly luciferase-ubiquitin-neomycin phosphotransferase fusion protein and EMCV-IRES driven NS3-5B HCV polyprotein] was cultured in RPMI medium (Gibco) supplemented with 10% fetal calf serum, 2 mM L-glutamine (Life Technologies), 1× non-essential amino acids (Life Technologies); 100 IU/ml penicillin and 100 ug/ml streptomycin and 250 ug/ml G418 (Geneticin, Life Technologies). Cells were seeded at a densitiy of 7000 cells per well in 96 well View Plate™ (Packard) in medium containing the same components as described above, except for G418. Cells were allowed to adhere and proliferate for 24 hr. At that time, culture medium was removed and serial dilutions of the test compounds were added in culture medium lacking G418. Interferon alfa 2a (500 IU) was included as a positive control. Plates were further incubated at 37° C. and 5% $CO_2$ for 72 hours. Replication of the HCV replicon in Huh-5 cells results in luciferase activity in the cells. Luciferase activity is measured by adding 50 µl of 1× Glo-lysis buffer (Promega) for 15 minutes followed by 50 ul of the Steady-Glo Luciferase assay reagent (Promega). Luciferase activity is measured with a luminometer and the signal in each individual well is expressed as a percentage of the untreated cultures. Parallel cultures of Huh-5-2 cells, seeded at a density of 7000 cells/well of classical 96-well cell culture plates (Becton-Dickinson) are treated in a similar fashion except that no Glo-lysis buffer or Steady-Glo Luciferase reagent is added. Instead the density of the culture is measured by means of the MTS method (Promega).

Quantitative Analysis of HCV RNA by Taqman Real-Time RT-PCR

Replicon cells were plated at $7.5 \times 10^3$ cells per well in a 96-well plate plates at 37° C. and 5% $CO_2$ in Dulbecco's modified essential medium containing 10% fetal calf serum, 1% nonessential amino acids and 1 mg/ml Geneticin. After allowing 24 h for cell attachment, different dilutions of compound were added to the cultures. Plates were incubated for 5 days, at which time RNA was extracted using the Qiamp Rneazyi Kit (Qiagen, Hilden, Germany). A 50 µL PCR reaction contained TaqMan EZ buffer (50 mmol/L Bicine, 115 mmol/L potassium acetate, 0.01 mmol/L EDTA, 60 nmol/L 6-carboxy-X-rhodamine, and 8% glycerol, pH 8.2; Perkin Elmer Corp./Applied Biosystems), 300 µmol/L deoxyadenosine triphosphate, 300 µmol/L deoxyguanosine triphosphate, 300 µmol/L deoxycytidine triphosphate, 600 µmol/L deoxyuridine triphosphate, 200 µmol/L forward primer [5'-ccg gcT Acc Tgc ccA TTc], 200 µmol/L reverse primer [ccA GaT cAT ccT gAT cgA cAA G], 100 µmol/L TaqMan probe [6-FAM-AcA Tcg cAT cgA gcg Agc Acg TAc-TAMRA], 3 mmol/L manganese acetate, 0.5 U AmpErase uracil-N-glycosylase, 7.5 U rTth DNA polymerase, and 10 µl of RNA elution. After initial activation of uracil-N-glycosylase at 50° C. for 2 minutes, RT was performed at 60° C. for 30 minutes, followed by inactivation of uracil-N-glycosylase at 95° C. for 5 minutes. Subsequent PCR amplification consisted of 40 cycles of denaturation at 94° C. for 20 seconds and annealing and extension at 62° C. for 1 minute in an ABI 7700 sequence detector. For each PCR run, negative template and positive template samples were used. The cycle threshold value (Ct-value) is defined as the number of PCR cycles for which the signal exceeds the baseline, which defines a positive value. The sample was considered to be positive if the Ct-value was <50. Results are expressed as genomic equivalents (GE).

Anti-Coxsackie Virus Assay

Ninety-six-well cell culture plates were seeded with Vero cells in DMEM medium containing 10 fetal calf serum (FCS) so that cells reached confluency 24-48 hr later. Medium was then removed and serial 5-fold dilutions of the test compounds were added in a total volume of 100 ul, after which the virus inoculum (100 µl) was added to each well. The virus inoculum used resulted in a 90-100% destruction of the cell monolayer after 5 days incubation at 37° C. Uninfected cells and cells receiving virus without compound were included in each assay plate. After 5 days, the medium was removed and 90 µl of DMEM-FCS and 10 µl of MTS/PMS solution (Promega) was added to each well. Following a 2 hr incubation period at 37° C., the optical density of the wells was read at 498 nm in a microplate reader. The 50% effective concentration (EC50) value was defined as the concentration of compound that protects 50% of the cell monolayer from virus-induced cytopathic effect Example 66

Determination of the Mechanism of Action of the Compounds

Generation of Drug-Resistant Virus and Determination of the Pheno- and Genotype of the Resistant Virus Wild type BVDV (strain NADL) was twice plaque purified on MDBK cells. The entire coding region of the genome of this virus was sequenced. This plaque purified and sequenced virus was then cultured in the presence of increasing drug concentrations of compound (GPJN22). Following 12 passages, the virus was at least 25 fold resistant to compound GPJN22. The resistant virus preparation was again plaque purified. The entire coding region of the genome of this virus was sequenced. A mutation F224S in the RNA dependent RNA polymerase gene of the virus was detected in 4 out of 4 clones of this virus; no other mutations were detected in the resistant viruses. The GPJN22-resistant virus was cross-resistant with VP32947 (see Table 8). VP32947 is an earlier reported selective inhibitor of BVDV replication [Baginski S G et al., Proc Natl Acad Sci U S A. 2000 Jul 5;97(14):7981-6]. In VP32947-resistant BVDV, a similar mutation was identified as being responsible for the drug-resistance. To confirm that the F224S mutation is indeed responsible for the resistant phenotype, the mutation was reintroduced by site-directed mutagenesis in an full-length infectious clone of the BVDV (strain NADL) [Vassilev et al., J Virol. 1997 Jan;71(1):471-8.]. The recombinant virus thus generated exhibited the same drug-resistance profile as the F224S mutant virus that was generated following culturing in increasing drug concentrations.

Example 67

Anti-BVDV (Strain PE515) Activity in MDBK Cells

The results of the testing of the compound of the invention in the anti-BVDV assay described above are provided in Table 9.

TABLE 9

| Compound | example | $EC_{50}$ (µg/ml) | $CC_{50}$ (µg/ml) | SI |
|---|---|---|---|---|
| GPJN-1 | 4 | 0.240 | >83.3 | >345 |
| GPJN-3 | 5 | 0.060 | 60 | 1003 |
| GPJN-4 | 6 | 0.040 | 46 | 1144 |
| GPJN-7 | 9 | 0.042 | 22 | 525 |
| GPJN-8 | 10 | 0.086 | 51 | 592 |
| GPJN-9 | 11 | 0.049 | | |
| GPJN-9 xHCl | 25 | 0.016 | | |
| GPJN-11 | 12 | 0.032 | 36 | 1135 |
| GPJN-12 | 13 | 0.059 | 56 | 949 |
| GPJN-13 | 14 | 0.043 | 45 | 1058 |
| GPJN-14 | 8 | 0.070 | 40 | 573 |
| GPJN-15 | 17 | 0.009 | 29 | 3079 |
| GPJN-16 | 21 | 0.246 | 8.1 | 33 |
| GPJN-17 | 18 | 0.097 | 50 | 517 |
| GPJN-18 | 19 | 0.019 | 55 | 2933 |
| GPJN-19 | 20 | 0.013 | 40 | 3012 |
| GPJN-20 | 15 | 0.165 | 28 | 169 |
| GPJN-21 | 16 | 0.022 | 22 | 1020 |
| GPJN-22 | 22 | 0.029 | 13 | 450 |
| GPJN-23 | 23 | 0.014 | 46 | 3230 |
| GPJN-24 | 24 | 0.040 | 21 | 519 |
| GPJN-25 | 26 | 0.009 | 36 | 4138 |
| GPJN-26 | 27 | 0.041 | >100 | >2439 |
| GPJN-27 | 28 | 0.945 | >46 | >48 |
| GPJN-28 | 29 | 0.325 | >75 | >230 |
| GPJN-31 | 32 | 0.455 | >100 | >222 |
| GPJN-32 | 35 | 0.027 | 20 | 741 |
| GPJN-33 | 36 | 0.200 | 70 | 350 |
| GPJN-34 | 33 | 0.865 | >100 | >116 |
| GPJN-35 | 34 | 0.365 | >100 | >273 |
| GPJN-36 | 37 | 0.019 | 24 | 1297 |
| GPJN-37 | 38 | 0.161 | 22 | 137 |
| GPJN-38 | 39 | 0.235 | 50 | 213 |
| GPJN-39 | 40 | 0.245 | >100 | >408 |
| GPJN-40 | 41 | 0.250 | >100 | >400 |
| GPJN-41 | 42 | 0.580 | >100 | >172 |
| GPJN-48 | 43 | 0.351 | >100 | >285 |
| GPJN-49 | 49 | 0.180 | 62 | 344 |
| GPJN-50 | | 0.021 | >100 | >4760 |
| GPJN-53 | 50 | 0.033 | 66 | 2028 |
| GPJN-54 | 44 | 0.100 | 35 | 349 |
| GPJN-55 | 45 | 0.060 | >100 | >1666 |
| GPJN-58 | 47 | 0.052 | 8.1 | 156 |
| GPJN-60 | | 0.015 | >77 | 5133 |
| GPJN-62 | 52 | 0.120 | 9.4 | 78 |
| GPJN-63 | 53 | 0.0042 | 4.3 | 1023 |
| GPJN-64 | | 0.026 | >100 | >3846 |
| GPJN-65 | | 0.01 | >100 | >10.000 |
| GPJN-68 | | 0.026 | 17 | 653 |
| GPJN-73 | | 0.017 | >100 | >5882 |
| GPJN-75 | | 0.018 | 31.7 | 1761 |
| GPJN-79 | | 0.083 | >100 | >1204 |
| GPJN-80 | | 0.18 | >100 | >555 |
| GPC-10 | | 0.064 | 4 | 62.5 |
| GPC-11 | | 0.56 | >100 | >178 |
| GPC-13 | | 0.067 | >100 | >1492 |

TABLE 9-continued

| Compound | example | $EC_{50}$ (μg/ml) | $CC_{50}$ (μg/ml) | SI |
|---|---|---|---|---|
| GPRTI-8 | 3 | 0.137 | >79 | >576 |
| VP32947** | | 0.003 | 47 | >16785 |

**Baginsky et al., Proc Natl Acad Sci U S A Jul 5, 2000; 97(14): 7981–6
$EC_{50}$: effective concentration required to reduce virus induced cytopathic effect in MDBK cells by 50%.
$IC_{50}$: inhibitory concentration required to reduce the growth of exponentially growing MDBK cells by 50%
SI: $IC_{50}/EC_{50}$.
Data are mean values for 2–5 independent determinations

Example 68

Anti-BVDV Activity of Compounds GPJN-100 to GPJN-115

TABLE 10

| Compound | example | $EC_{50}$ (μg/ml) | MTC (μg/ml) | SI |
|---|---|---|---|---|
| GPJN-100 | | 0.088 | 20 | 227 |
| GPJN-103 | 65 | 0.061 | 20 | 328 |
| GPJN-104 | | 0.27 | 20 | 74 |
| GPJN-105 | | 0.021 | 100 | 4762 |
| GPJN-107 | | 0.088 | 100 | 1136 |
| GPJN-108 | | 0.061 | 20 | 328 |
| GPJN-109 | | 0.27 | 20 | 74 |
| GPJN-110 | 57 | 0.021 | 4 | 190 |
| GPJN-112 | 58 | 0.0049 | 20 | 4082 |
| GPJN-113 | 59 | 0.0031 | 20 | 6452 |
| GPJN-114 | 60 | 0.021 | 20 | 952 |
| GPJN-115 | 61 | 0.24 | 4 | 17 |

$EC_{50}$: effective concentration required to reduce virus induced cytopathic effect in MDBK cells by 50%.
MTC: mean toxic concentration, concentration required to reduce the growth of exponentially growing MDBK cells by 50%
SI: $MTC/EC_{50}$.

Example 69

Effect of Compounds in HCV-Huh-5-2 Replicon Cells

TABLE 11

| Compound | EC50 | CC50 | SI |
|---|---|---|---|
| GPJN-16 | 1 | 3 | 3 |
| GPJN-52 | 0.2 | 24 | 118 |
| GPJN-58 | 0.13 | 2 | 15 |
| GPJN-62 | <0.62 | 6 | >10$^{10}$ |
| GPJN-83 | <0.62 | 8 | >12 |
| GPJN-87 | <0.62 | 20 | >32 |
| GPJN-96 | 1 | 4 | 3 |
| GPJN-110 | 0.21 | 5.9 | 28 |
| GPJN-112 | 0.29 | >17 | >58$^{15}$ |
| GPJN-113 | 0.17 | 14 | 82 |
| GPJN-114 | 0.12 | 6.15 | 50 |

EC50: concentration required to inhibit luciferase activity in the replicon system by 50%.
CC50: concentration required to inhibit the proliferation of exponentially growing Huh-5-2 cells by 50%.

Example 70

Effect of GPJN-52 and GPJN-58 on Replicon (RNA) Synthesis in Huh-5-2 Cells.

TABLE 12

| | CT | Delta CT |
|---|---|---|
| 5 ug/ml GPJN 52 | 31.14 | 2.28 |
| 1 ug/ml GPJN 52 | 30.23 | 1.37 |
| 0.2 ug/ml GPJN52 | 29.25 | 0.39 |
| 0.04 ug/ml GPJN52 | 29.11 | 0.25 |
| 0.01 ug/ml GPJN52 | 29.00 | 0.14 |
| 1 ug/ml GPJN-58 | 32.86 | 4 |
| 0.2 ug/ml GPJN-58 | 30.00 | 1.14 |
| 0.04 ug/ml GPJN-58 | 29.89 | 1.03 |
| 0.008 ug/ml GPJN-58 | 29.75 | 0.89 |
| 0.0016 u/ml GPJN-58 | 28.91 | 0.05 |
| untreated | 28.86 ± 0.04 | |

Effect of the antivirals on the synthesis of the HCV replicon as determined by means of real-time quantitative RT-PCR. A higher Delta CT value indicates a more profound inhibition of viral RNA synthesis.

Example 71

Antioxsackie B3 Activity in Vero Cells

TABLE 13

| Compound | example | $EC_{50}$ (μg/ml) | $TC_{50}$ (μg/ml) | SI |
|---|---|---|---|---|
| GPJN-5 | | 6.0 | >100 | 16.6 |
| GPJN-32 | 35 | 6.5 | 69 | 15.4 |
| GPJN-40 | 41 | 8.95 | >100 | 11.2 |
| GPJN-50 | | 8.47 | >100 | 11.8 |
| GPJN-60 | | 6.1 | >100 | 16.4 |
| GPJN-64 | | 12 | >42 | 3.5 |
| GPC-10 | | 1.81 | 59 | 32.59 |
| GPC-11 | | 4.76 | >100 | 21.0 |
| GPC-12 | | 3.6 | >100 | 27.7 |
| GPRTI-8 | 3 | 12.2 | >100 | 8.48 |

$EC_{50}$: effective concentration required to reduce virus (CBV-3 Nancy strain)-induced cytopathic effect in Vero cells by 50%.
$IC_{50}$: effective concentration required to reduce the metabolism of confluent Vera cells by 50% as determined by the MTS method.
SI: $IC_{50}/EC_{50}$.
Data are mean values for two or more independent determinations

The invention claimed is:
1. Method for treatment of a Flaviviridae or Picornaviridae viral infection comprising the step of administering an effective amount of an imidazo[4,5-c]pyridine derivative of formula (Z), or a pharmaceutically acceptable salt thereof,

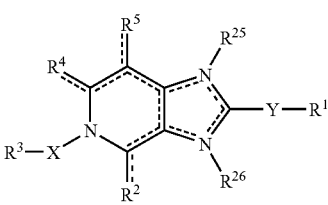

(Z)

wherein:
the dotted lines represent an optional double bond, provided that no two double bonds are adjacent to one another, and that the dotted lines represent at least 3, optionally 4, double bonds;

$R^1$ is aryl unsubstituted or substituted with one or more $R^6$;

Y is a single bond;

each $R^2$ and $R^4$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halo; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5- or 6-membered heterocyclic, oxyheterocyclic or thioheterocyclic ring; or, when one of $R^{25}$ or $R^{26}$ is different from hydrogen, either $R^2$ or $R^4$ is selected from (=O), (=S), and (=$NR^{27}$);

X is methylene;

$R^3$ is a 6-membered heterocyclic, oxyheterocyclic or thioheterocyclic ring optionally substituted with one or more $R^{17}$;

$R^5$ is selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halo; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocyclic, oxyheterocyclic or thioheterocyclic ring;

each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halo; OH; CN; $NO_2$; $NR^7R^8$; $OCF_3$; haloalkyl; $C(=O)R^{18}$; $C(=S)R^{18}$; SH; aryl; aryloxy; arylthio; arylalkyl; arylalkyloxy (optionally a oxybenzyl); arylalkylthio (optionally a benzylthio); 5- or 6-membered heterocyclic, oxyheterocyclic or thioheterocyclic ring; $C_{1-18}$ hydroxyalkyl; and each of said aryl, aryloxy, arylthio, arylalkyl, arylalkyloxy (optionally oxybenzyl), arylalkylthio (optionally benzylthio), 5- or 6-membered heterocyclic, oxyheterocyclic or thioheterocyclic ring, or $C_{1-18}$ hydroxyalkyl is optionally substituted with 1 or more $R^{19}$;

each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5- or 6-membered heterocyclic ring; $C(=O)R^{12}$; $C(=S)R^{12}$; and an amino acid residue linked through a carboxyl group thereof; alternatively, $R^7$ and $R^8$, together with the nitrogen to which they are attached, combine to form a 5- or 6-membered heterocyclic ring;

each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl; and an amino acid residue linked through an amino group thereof;

each $R^{10}$ and $R^{11}$ is independently selected from the group consisting of H; $C_{1-18}$ alkyl; $C_{2-18}$ alkenyl; $C_{3-10}$ cycloalkyl; $C_{4-10}$ cycloalkenyl; aryl; $C(=O)R^{12}$; 5- or 6-membered heterocyclic ring; and an amino acid residue linked though a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; and an amino acid residue linked through an amino group thereof;

each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; and an amino acid residue linked through a carboxyl group thereof;

$R^{19}$ is independently selected from the group consisting of H; $C_{1-18}$ alkyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halo; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; and arylalkyl; and each of said aryl, aryloxy, arylthio, arylalkyl may be substituted with one or more halo, particularly a phenyl substituted with 1-2 halo; hydroxyalkyl; 5- or 6-membered heterocyclic, oxyheterocyclic or thioheterocyclic ring each unsubstituted or substituted with 1 or more halogens;

each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R^{12}$; and $C(=S)R^{12}$;

$R^{22}$ is independently selected from H; OH; $C_{1-18}$ alkyl; $C_{2-18}$ alkenyl; $C_{1-18}$ alkoxy; $NR^{23}R^{24}$; aryl; $C_{3-10}$ cycloalkyl; and $C_{4-10}$ cycloalkenyl;

each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

each $R^{25}$ or $R^{26}$ is absent or is selected from the group consisting of H, $C_{1-18}$ alkyl, preferably $C_{1-4}$ alkyl; $C_{3-10}$ cycloalkyl (such as cyclopentyl, cyclohexyl, $C_{5-10}$ bicycloalkyl or adamantyl); $C_{3-10}$ cycloalkenyl; ($C_{3-8}$ cycloalkyl)-$C_{1-3}$ alkyl; aryl, such as phenyl; 5- or 6-membered heterocyclic ring, such as pyridyl; alkylaryl, such as benzyl; and each of said $C_{1-18}$ alkyl, preferably $C_{1-4}$ alkyl, $C_{3-10}$ cycloalkyl, $C_{3-10}$ cycloalkenyl, ($C_{3-8}$ cycloalkyl) -$C_{1-3}$ alkyl, $C_{5-10}$ bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocyclic ring having 3 to 7 carbon atoms, preferably a saturated heterocyclic ring wherein the heteroatoms are S, S(O), or $S(O)_2$ separated from the imidazopyridyl ring nitrogen atom by at least 2 heterocyclic ring carbon atoms, provided that either $R^{25}$ or $R^{26}$ is hydrogen, typically $R^{25}$ or $R^{26}$ is cyclopentyl or cyclohexyl; provided that if the compound is substituted at $R^{25}$ or $R^{26}$, either $R^2$ or $R^4$ is selected from (=O), (=S), and (=$NR^{27}$); and $R^{27}$ is selected from the group consisting of H, $C_{1-18}$ alkyl, $C_{3-10}$ cycloalkyl, ($C_{3-10}$ cycloalkyl)-$C_{1-6}$ alkyl; aryl; and arylalkyl, such as benzyl;

or an isomer thereof, or a pharmaceutically acceptable salt thereof.

2. The method according to claim 1, wherein said viral infection is an infection of a virus belonging to the family of the Flaviviridae.

3. The method according to claim 1, wherein said viral infection is an infection of a hepatitis-C virus.

4. The method according to claim 1, wherein said viral infection is an infection of a virus belonging to the family of the Picornaviridae.

5. The method according to claim 1, wherein said viral infection is an infection of a Coxsackie virus.

6. The method according to claim 1, wherein the effective amount of imidazo[4,5-c]pyridine derivative is suitable for separate, combined or sequential administration comprising the steps:

(a) the administration of an effective amount of one or more compound(s) of formula (Z), as defined in claim 1; and (b) the administration of an effective amount of one or more compound(s) effective in the treatment or prophylaxis of viral infections, including Flaviviral or Picornaviral enzyme inhibitors, in respective proportions such as to provide a synergistic effect against said viral infection.

7. The method according to claim 1, wherein the effective amount of imidazo[4,5-c]pyridine derivative is suitable for administration orally, intranasally, subcutaneously, intramuscularly, intradermally, intravenously, intra-arterially, parenterally or by catheterization.

8. The method according to claim 1, wherein the imidazo [4,5-c]pyridine derivative of formula (Z) is selected from the group consisting of:
   5-[(4-pyridinyl)methyl]-2-phenyl-5H-imidazo[4,5-c]pyridine;
   5-[(2-pyridinyl)methyl]-2-phenyl-5H-imidazo[4,5-c]pyridine; and
   5-[(3-pyridinyl)methyl]-2-phenyl-5H-imidazo[4,5-c]pyridine.

9. The method according to claim 1, wherein the imidazo [4,5-c]pyridine derivative of formula (Z) has the formula:

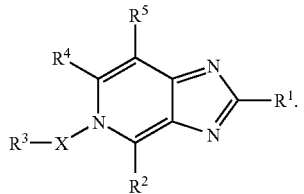

* * * * *